US008828953B2

(12) United States Patent
Baron et al.

(10) Patent No.: US 8,828,953 B2
(45) Date of Patent: Sep. 9, 2014

(54) CHEMOSENSORY RECEPTOR LIGAND-BASED THERAPIES

(75) Inventors: Alain Baron, San Diego, CA (US);
Martin R. Brown, Coronado, CA (US);
Christopher R. G. Jones, San Diego, CA (US)

(73) Assignee: NaZura BioHealth, Inc., San Diego, CA (US)

(*) Notice: Subject to any disclaimer, the term of this patent is extended or adjusted under 35 U.S.C. 154(b) by 0 days.

(21) Appl. No.: 12/907,909

(22) Filed: Oct. 19, 2010

(65) Prior Publication Data
US 2011/0065660 A1    Mar. 17, 2011

Related U.S. Application Data

(63) Continuation-in-part of application No. 12/763,926, filed on Apr. 20, 2010.

(60) Provisional application No. 61/170,657, filed on Apr. 20, 2009.

(51) Int. Cl.
*A61K 31/704* (2006.01)

(52) U.S. Cl.
USPC .............................. 514/26; 514/171

(58) Field of Classification Search
CPC ........... A61K 9/20; A61K 9/28; A61K 31/13; A61K 13/3132; A61K 31/35
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 4,036,948 A | 7/1977 | Kitamori et al. |
| 4,115,538 A | 9/1978 | Satoh et al. |
| 4,434,153 A | 2/1984 | Urquhart et al. |
| 4,844,905 A | 7/1989 | Ichikawa et al. |
| 4,915,952 A | 4/1990 | Ayer et al. |
| 5,007,790 A | 4/1991 | Shell |
| 5,059,595 A | 10/1991 | Le Grazie |
| 5,073,543 A | 12/1991 | Marshall et al. |
| 5,120,548 A | 6/1992 | McClelland et al. |
| 5,135,757 A | 8/1992 | Baichwal et al. |
| 5,322,697 A | 6/1994 | Meyer |
| 5,328,942 A | 7/1994 | Akhtar et al. |
| 5,354,556 A | 10/1994 | Sparks et al. |
| 5,424,286 A | 6/1995 | Eng |
| 5,436,128 A | 7/1995 | Harpold et al. |
| 5,451,409 A | 9/1995 | Rencher et al. |
| 5,582,837 A | 12/1996 | Shell |
| 5,589,194 A | 12/1996 | Tsuei et al. |
| 5,591,767 A | 1/1997 | Mohr et al. |
| 5,603,957 A | 2/1997 | Burguiere et al. |
| 5,639,476 A | 6/1997 | Oshlack et al. |
| 5,691,188 A | 11/1997 | Pausch et al. |
| 5,733,566 A | 3/1998 | Lewis |
| 5,753,253 A | 5/1998 | Meyer |
| 5,783,212 A | 7/1998 | Fassihi et al. |
| 5,846,566 A | 12/1998 | Burguiere et al. |
| 5,874,243 A | 2/1999 | Macina et al. |
| 5,945,125 A | 8/1999 | Kim |
| 5,952,021 A | 9/1999 | Santus et al. |
| 5,972,389 A | 10/1999 | Shell et al. |
| 6,022,562 A | 2/2000 | Autant et al. |
| 6,090,411 A | 7/2000 | Pillay et al. |
| 6,120,803 A | 9/2000 | Wong et al. |
| 6,210,710 B1 | 4/2001 | Skinner |
| 6,217,903 B1 | 4/2001 | Skinner |
| 6,245,356 B1 | 6/2001 | Baichwal |
| 6,267,988 B1 | 7/2001 | Meyer |
| 6,487,445 B1 | 11/2002 | Serita et al. |
| 6,530,886 B1 | 3/2003 | Ishida et al. |
| 6,558,708 B1 | 5/2003 | Lin |
| 6,685,962 B2 | 2/2004 | Friedman et al. |
| 6,815,436 B2 | 11/2004 | Hansson et al. |
| 6,850,797 B2 | 2/2005 | Kawanishi et al. |
| 6,864,415 B2 | 3/2005 | Koyanagi et al. |
| 7,105,650 B2 | 9/2006 | Adler |
| 7,812,004 B2 | 10/2010 | Frippiat et al. |
| 7,883,856 B2 | 2/2011 | Li et al. |
| 2002/0160424 A1 | 10/2002 | Adler et al. |
| 2003/0072822 A1 | 4/2003 | Ribnicky et al. |

(Continued)

FOREIGN PATENT DOCUMENTS

| | | |
|---|---|---|
| CN | 1 125 574 A | 7/1996 |
| CN | 100 490 789 C | 5/2009 |

(Continued)

OTHER PUBLICATIONS

Food and Drug Administration, "Food Additives Permitted for Direct Addition to Food for Human Consumption; Sucralose", Federal Register /vol. 63, No. 64 / Friday, Apr. 3, 1998 /Rules and Regulations, pp. 16417-16433.*
Grotz et al., Lack of effect of sucralose on glucose homeostasis in subjects with type 2 diabetes, Dec. 2003, Journal of the American Dietetic Association 103(12):1607-1612.*
Mezitis et. al., Glycemic Effect of a Single High Oral Dose of the Novel Sweetener Sucralose in Patients With Diabetes, Sep. 1996, Diabetes Care 19(9):1--4-1005.*
Ma et al., Effect of the artificial sweetener, sucralose, on gastric emptying and incretin hormone release in healthy subjects, Feb. 12, 2009, Am J Physiol Gastrointest Liver Physiol 296: G735-G739.*
Fujita et al., Incretin release from gut is acutely enhanced by sugar but not by sweeteners in vivo, Dec. 23, 2008, Am J Physiol Endocrinol Metab 296: E473-E479.*
Adler et al., "A Novel Family of Taste Receptors," *Cell*, 2000, 100:693-702.

(Continued)

*Primary Examiner* — John Ulm
(74) *Attorney, Agent, or Firm* — Todd Lorenz; Arnold & Porter LLP

(57) ABSTRACT

Provided herein are methods for treating diabetes, obesity, and other metabolic diseases, disorders or conditions comprising chemosensory receptor ligands. Also provided herein are chemosensory receptor ligand compositions and the preparation thereof for the methods of the present invention.

22 Claims, No Drawings

(56) References Cited

U.S. PATENT DOCUMENTS

| | | | |
|---|---|---|---|
| 2004/0109894 | A1 | 6/2004 | Shefer et al. |
| 2004/0258735 | A1 | 12/2004 | Van Benthum et al. |
| 2004/0258803 | A1 | 12/2004 | Van Benthum et al. |
| 2005/0038415 | A1 | 2/2005 | Rohr et al. |
| 2005/0238777 | A1 | 10/2005 | Klingeberg et al. |
| 2005/0244810 | A1 | 11/2005 | Egan et al. |
| 2007/0032420 | A1 | 2/2007 | Polidori et al. |
| 2008/0274215 | A1 | 11/2008 | Morrow |
| 2008/0305500 | A1 | 12/2008 | Servant et al. |
| 2008/0306053 | A1 | 12/2008 | Tachdjian |
| 2008/0306076 | A1 | 12/2008 | Li et al. |
| 2008/0306093 | A1 | 12/2008 | Servant et al. |
| 2008/0311192 | A1 | 12/2008 | West et al. |
| 2009/0062193 | A1 | 3/2009 | Weyer |
| 2009/0170948 | A1 | 7/2009 | Niddam-Hildesheim et al. |
| 2010/0093861 | A1 | 4/2010 | Hermansen et al. |
| 2011/0045069 | A1 | 2/2011 | Ley et al. |
| 2011/0268795 | A1 | 11/2011 | Fayad |
| 2013/0273154 | A1 | 10/2013 | Fayad et al. |

FOREIGN PATENT DOCUMENTS

| | | |
|---|---|---|
| EP | 0867508 A2 | 9/1998 |
| WO | WO 92/17585 A1 | 10/1992 |
| WO | WO 93/18755 A1 | 9/1993 |
| WO | WO 95/18140 A1 | 7/1995 |
| WO | WO 96/01623 A1 | 1/1996 |
| WO | WO 96/26718 A2 | 9/1996 |
| WO | WO 97/17444 A2 | 5/1997 |
| WO | WO 97/18814 A1 | 5/1997 |
| WO | WO 98/55107 A1 | 12/1998 |
| WO | WO 99/67282 A2 | 12/1999 |
| WO | WO 01/23341 | 4/2001 |
| WO | WO 2007/085593 | 5/2005 |
| WO | WO 2006/119389 A2 | 11/2006 |
| WO | WO 2005/046580 | 8/2007 |
| WO | WO 2008/008224 | 1/2008 |
| WO | WO 2008/057968 A2 | 5/2008 |
| WO | WO 2008/154221 A2 | 12/2008 |
| WO | WO 2009/026389 | 2/2009 |
| WO | WO 2009/049105 | 4/2009 |
| WO | WO 2010/027498 | 3/2010 |
| WO | WO 2010/027498 A2 | 3/2010 |
| WO | WO 2010/112256 | 10/2010 |
| WO | WO 2012/118712 A2 | 9/2012 |
| WO | WO 2013/063527 A1 | 5/2013 |

OTHER PUBLICATIONS

Adrian et al., "Deoxycholate is an Important Releaser of Peptide Yy and Enteroglucagon From the Human Colon," *Gut*, 1993, 34(9):1219-1224.

Adrian et al. "Human Distribution and Release of a Putative New Gut Hormone, Peptide YY." *Gastroenterology*, 1985, 89:1070-1077.

Altenhofen et al., "Control of ligand specificity in cyclic nucelotide-gated channels from rod photoreceptors and olfactory epithelium," *PNAS USA*, 1991, 88:9868-9872.

Anton et al. "Effects of Stevia, Aspartame and Sucrose on Food Intake, Satiety, and Postprandial Glucose and Insulin Levels." *Appetite* 2010, 55:37-43.

Bachmanov et al. "Taste Receptor Genes." *Annual Review of Nutrition*, 2007, 27:389-414.

Baricos et al., "Extracellular Matrix Degradation by Cultured Mesangial Cells: Mediators and Modulators," *Exp Biol Med*, 2003, 228:1018-1022.

Batterham et al. "Inhibition of Food Intake in Obese Subjects by Peptide Yy3-36." *The New England Journal of Medicine*, 2003, 349:941-948.

Berridge and Irvine. "Inositol Trisphosphate, a Novel Second Messenger in Cellular Signal Transduction." *Nature*, 1984, 312:315-321.

Bloomgarden, "American Diabetes Association Annual Meeting. 1999: Diabetes and Obesity," *Diabetes Care*, 2000, 23:118-124.

Bold et al. "Biomolecular Advances in Gastrointestinal Hormones." *Arch Surg.*, 1993, 128:1268-1273.

Bose et al. "Do Incretins Play a Role in the Remission of Type 2 Diabetes after Gastric Bypass Surgery: What are the Evidence?" *Obesity Surgery*, 2009, 19(2):217-229.

Bourne et al. "The GTPase Superfamily: Conserved Structure and Molecular Mechanism." *Nature*, 1991, 10:117-127.

Bourne et al. "The GTPase Superfamily: A Conservative Switch for Diverse Cell Functions." *Nature*, 1990, 348:125-132.

Brown et al., "Ingestion of Diet Soda before a Glucose Load Augments Glucagon-Like Peptide-1 Secretion," *Diabetes Care*, 2009, 32:2184-2186.

Brubaker and Drucker. "Structure-Function of the Glucagon Receptor Family of G Protein-Coupled Receptors: The Glucagon, GIP, GLP-1, and GLP-2 Receptors." *Receptors Channels*, 2002, 8:179-188.

Buck et al., "A Novel Multigene Family May Encode Odorant Receptors: A Molecular Basis for Odor Recognition," *Cell*, 1991, 65:175-187.

Burrin et al., "Glucagon-Like Peptide 2: a Nutrient-Responsive Gut Growth Factor," *J Nutrition*, 2001, 131(3):709.

Cani et al., "The Role of the Gut Microbiota in Energy Metabolism amd Metabolic Disease," *Current Pharmaceutical Design*, 2009, 15:1546-1558.

Carelli et al. "Silicone Microspheres for pH-Controlled Gastrointestinal Drug Delivery." *Int. J. Pharmaceutics*, 1999, 179:73-83.

Chan et al., "Peptide Yy Levels Are Elevated after Gastric Bypass Surgery," *Obesity*, 2006, 14(2): 194-198.

Chandrashekar et al., "T2Rs Function as Bitter Taste Receptors," *Cell*, 2000, 100:703-711.

Chandrashekar et al. "The cells and peripheral representation of sodium taste in mice." 2010 *Nature* 464(7286): 297-301.

Chanoine et al., "Glp-1 and Appetite Responses to a Meal in Lean and Overweight Adolescents Following Exercise," *Obesity*, 2008, 16:202-204.

Chatsudthipong et al. "Stevioside and Related Compounds: Therapeutic Benefits Beyond Sweetness." *Pharmacology & Therapeutics*, 2009, 121:41-54.

Chen et al. "Bitter Stimuli Induce Ca2+ Signaling and Cck Release in Enteroendocrine Stc-1 Cells: Role of L-Type Voltage-Sensitive Ca2+ Channels." *American Journal of Physiology, Cell Physiology*, 2006, 291:C726-C739.

Chen et al., "Gut Expression and Regulation of FAT-CD36:Possible Role in Fatty Acid Transport in Rat Enterocytes," *Am J Physiol Endocrinol Metab*, 2001, 281(5):E916-E923.

Christiansen et al., "Discovery of Potent and Selective Agonists for the Free Fatty Acid Receptor 1 (Ffa(1)-Gpr40), a Potential Target for the Treatment of Type II Diabetes," *Journal of Medicinal Chemistry*, 2008, 51:7061-7064.

Claustre et al., "Stimulatory effect of β-adrenergic agonists on ileal L cell secretion and modulation by α-adrenergic activation," *J Endocrin*, 1999, 162:271-278.

Cummings et al., "Gastrointestinal Regulation of Food Intake," *The Journal of Clinical Investigation*, 2007, 117:13-23.

Damholt et al., "Glucagon-Like-Peptide-1 Secretion from Canine L-Cells Is Increased by Glucose-Dependent-Insulinotropic Peptide but Unaffected by Glucose," *Endocrinology*, 1998, 139(4):2085-2091.

De Araujo et al., "Food Reward in the Absence of Taste Receptor Signaling,"*Neuron*, 2008, 57:930-941.

Deacon et al., "Preservation of Active Incretin Hormones by Inhibition of Dipeptidyl Peptidase IV Suppresses Meal-Induced Incretin Secretion in Dogs," *The Journal of Endocrinology*, 2002, 172:355-362.

Delmas et al. "Polycystins, Calcium Signaling, and Human Diseases." *Biochem Biophys Res Commun*, 2004, 322:1374-1383.

Delzenne et al., "Modulation of Glucagon-Like Peptide 1 and Energy Metabolism by Inulin and Oligofructose: Experimental Data," *J Nutr* 137:2547S-2551S (2007).

Dhallan et al. "Primary Structure and Functional Expression of a Cyclic Nucleotide-activated Channel from Olfactory Neurons." *Nature*, 1990, 347:184-187.

Dotson et al., "Bitter Taste Receptors Influence Glucose Homeostasis," *PloS one*, 2008, 3(12):1-10.

(56) References Cited

OTHER PUBLICATIONS

Drewnowski and Gomez-Carneros. "Bitter Taste, Phytonutrients, and the Consumer: A Review." *Am J Nutrition*, 2000, 72(6):1424.

Drucker, "The Role of Gut Hormones in Glucose Homeostasis," *The Journal of Clinical Investigation*, 2007, 117:24-32.

Dyer et al., "Intestinal Glucose Sensing and Regulation of Intestinal Glucose Absorption," *Biochemical Society Transactions*, 2007, 35(Part 5): 1191-1194.

Dyer et al. "Glucoase Sensing in the Intestinal Epithelium." *Eur. J. Biochem.*, 2003, 270:3377-3388.

Dyer et al. "Nutrient Regulation of Human Intestinal Sugar Transporter (SGLT1) Expression." *Gut*, 1997, 41:56-59.

Dynamics, "Gi Dynamics Announces Data Demonstrating Immediate and Susbtained Reduction in Hba1c in Patients with Type 2 Diabetes Using Endobarrier(Tm) Gastrointestinal Liner,", Sep. 2008, Press Release.

Elliott et al., "Glucagon-Like Peptide-1 (7-36)Amide and Glucose Dependent Insulinotropic Polypeptide Secretion in Response to Nutrient Ingestion in Man: Acute Post-Prandial and 24-H Secretion Patterns," *The Journal of Endrocrinology*, 1993, 138:159-166.

Engelstoft et al., "A Gut Feeling for Obesity: 7tm Sensors on Enteroendocrine Cells," *Cell Metabolism*, 2008, pp. 447-449.

Esler et al., "Small-Molecule Ghrelin Receptor Antagonists Improve Glucose Tolerance, Suppress Appetite, and Promote Weight Loss," *Endocrinology*, 2007, 148(11):5175-5185.

Felley-Bosco et al. "Constitutive Expression of Inducible Nitric Oxide Synthase in Human Bronchial Epithelial Cells Induces c-*fos* and Stimulates the cGMP Pathway." *Am J Resp Cell Mol Biol*, 1994, 11:159-164.

Feng et al., "Bear Bile: Dilemma of Traditional Medicinal Use and Animal Protection," *Journal of Ethnobiology and Ethnomedicine*, 2009, 5:1-9.

Ferrero et al., "Total and Active Ghrelin Levels in Women and Polycystic Ovary Syndrome," *Human Reproduction*, 2006, 21(2):565-572.

Flatt et al., "Bariatric Surgery to Treat Obesity," *British J Diab Vasc Disease*, 2009, 9:103-107.

Fowler et al., "Fueling the Obesity Epidemic? Artificially Sweetened Beverage Use and Long-Term Weight Gain," *Obesity*, 2008, 16:1894-1900.

Frank et al., "Sucrose Activates Human Taste Pathways Differently from Artificial Sweetener," *Neurolmage*, 2008, 39:1559-1569.

Fujita et al., "Incretin release From Gut Is Acutely Enhanced by Sugar but not by Sweeteners In Vivo," *Am J. Physiol Endcrinol Metab*, 2009, 296(3):E473-479 epub Dec. 23, 2008.

Galindo-Cuspinera et al., "The Liaison of Sweet and Savory," *Chemical Senses*, 2006, 31:221-225.

Geloneze et al., "Ghrelin: A Gut-Brain Hormone: Effect of Gastric Bypass Surgery," *Obesity Surgery*, 2003, 13:17-22.

Goto et al. "Effect of Combination Treatment with SK-0403, a Highly Selective DPP-IV Inhibitor, Miglitol on Incredtin Levels in Obese and Type 2 Diabetic Animals." *Poster P-470 ADA*, 2008.

Greenfield et al., "Oral Glutamine Increases Circulating Glucagon-Like Peptide 1, Glucagon, and Insulin Concentrations in Lean, Obese, and Type 2 Diabetic Subjects," *The American Journal of Clinical Nutrition*, 2009, 89:106-113.

Gregersen et al., "Antihyperglycemic Effects of Stevioside in Type 2 Diabetic Subjects," *Metabolism: Clinical and Experimental*, 2004, 53:73-76.

Grotz et al., "Lack of Effect of Sucralose on Glucose Homeostasis in Subjects with Type 2 Diabetes,"*Journal of the American Dietetic Association*, 2003, 103:1607-1612.

Grundy. "Obesity, Metabolic Syndrome, and Cardiovascular Disease." *J.Clin Endocrinol Metab*, 2004, 89(6):2595-2600.

Hevezi et al., "Genome-Wide Analysis of Gene Expression in Primate Taste Buds Reveals Links to Diverse Processes," *PloS one*, 2009, 4(7):1-13.

Hirasawa et al., "Free Fatty Acids Regulate Gut Incretin Glucagon-Like Peptide-1 Secretion Through Gpr120," *Nat Med*, 2005, 11:90-94.

Hofer et al., "Taste Receptor-Like Cells in the Rat Gut Identified by Expression of Alpha-Gustducin," *PNAS USA*, 1996, 93:6631-6634.

Holst, "The Physiology of Glucagon-Like Peptide 1," *Physiological Reviews*, 2007, 87:1409-1439.

Hoon et al., "Putative Mammalian Taste Receptors: A Class of Taste-Specific GPCRs with Distinct Topographic Selectivity," *Cell*, 1999, 96:541-551.

Huang et al., "The Cells and Logic for Mammalian Sour Taste Detection," *Nature*, 2006, 96:511-551.

Inouye et al. "Sustained Release Tablets Based on Chitosan and Carboxymethylcellulose Sodium." *Drug Design and Delivery*, 1987, 1:297-305.

Jang et al., "Gut-Expressed Gustducin and Taste Receptors Regulate Secretion of Glucagon-Like Peptide 1," *PNAS*, 2007, 104(38):15069-15074.

Jeon et al., "Srebp-2 Regulates Gut Peptide Secretion through Intestinal Bitter Taste Receptor Signaling in Mice," *The Journal of Clinical Investigation*, 2008, 118(11):3693-3700.

Jeon et al., "Changes in Plasma Ghrelin Concentration Immediately after Gastrectomy in Patients with Early Gastric Cancer," *The Journal of Clinical Endocrinology and Metabolism*, 2004, 89(11):5392-5396.

Jeppesen et al. "Stevioside Induces Antihyperglycaemic, Insulinotropic and Glucagonostatic Effects in Vivo: Studies in the Diabetic Goto-Kakizaki (Gk) Rats." *Phytomedicine: International Journal of Phytotherapy and Phytopharmacology*, 2002, 9:9-14.

Jeppesen et al., "Stevioside Acts Directly on Pancreatic Beta Cells to Secrete Insulin: Actions Independent of Cyclic Adenosine Monophosphate and Adenosine Triphosphate-Sensitive K+-Channel Activity," *Metabolism: Clinical and Experimental*, 2000, 49(2):208-214.

Jeppeson, "Clinical significance of GLP-2 in Short-Bowel Syndrome," *The Journal of Nutrition*, 2003, 133(11):3721-3724.

Jing et al., "Effect of the artificial sweetener, sucralose, on gastric emptying and incretin hormone release in healthy subjects," *Am J Physiuol Liver Physiol*, 2009, 296:G735-G739.

Jing et al., "Effect of the artificial sweetener, sucralose, on small intestinal glucose absorption in healthy human subjects," *Br J Nutr*, Apr. 2010, 27:1-4.

Kawamata et al., "A G protein-coupled receptor responsive to bile acids," *J Biol Chem*, 2003, 278:9435-9440.

Kim et al., "Highly sweet compounds of plant origin," *Arch Pharm Res*, 2002, 25(6):725=746.

Kinghorn et al., "Intensely sweet compounds of natural origin," *Med Res Reviews*, 1989, 9(1):91-115.

Kojima et al. "Ghrelin, An Orexigenic Signaling Molecule from the Gastrointestinal Tract." *Curr Op Pharmacol*, 2002, 2 :665-668.

Kokrashvili et al., "Taste Signaling Elements Expressed in Gut Enteroendocrine Cells Regulate Nutrient-Responsive Secretion of Gut Hormones," *The American Journal of Clinical Nutrition*, 2009, 90(supp):822S-825S.

Kondoh et al., "Activation of the Gut-Brain Axis by Dietary Glutamate and Physiologic Significance in Energy Homeostasis," *The American Journal of Clinical Nutrition*, 2009, 90(suppl):832S-837S.

Kondoh et al,, "Msg Intake Suppresses Weight Gain, Fat Deposition, and Plasma Leptin Levels in Male Sprague-Dawley Rats," *Physiol Behav*, 2008, 95:135-144.

Kuo et al., "Transient, Early Release of Glucagon-Like Peptide-1 During Low Rates of Intraduodenal Glucose Delivery," *Regul Pept*, 2008, 146:1-3.

Laferrere et al., "Incretin Levels and Effect are Markedly Enhanced 1 Month after Roux-en-Y Gastric Bypass Surgery in Obese Patients with Type 2 Diabetes," *Diabetes Care*, 2007, 30(7):1709-1716.

Laferrere et al., "Effect of Weight Loss by Gastric Bypass Surgery Versus Hypocaloric Diet of Glucose and Incretin Levels in Patients with Type 2 Diabetes," *The Journal of Clinical Endocrinology and Metabolism*, 2008, 93(7):2479-2485.

Laugerette et al., "CD36 involvement in orosensory detection of dietary lipids, spontaneous fat preference, and digestive secretions," *J Clin Investig*, 2005, 115(11):3177-3184.

(56) References Cited

OTHER PUBLICATIONS

Le Roux et al., "Gut Hormones as Mediators of Appetite and Weight Loss after Roux-En-Y Gastric Bypass," *Annals of Surgery*, 2007, 246(5):780-785.
Lee et al., "The Effects of Miglitol on Glucagon-Like Peptide-1 Secretion and Appetite Sensations in Obese Type 2 Diabetics," *Diabetes Obes Metab*, 2002, 4:329-335.
Lee et al., "Evidence for Gut Factor in K+ Homeostasis," *American Journal of Physiology, Renal Physiology*, 2007, 293:F541-F547.
Legakis et al., "Decreased Glucagon-Like Peptide 1 Fasting Levels in Type 2 Diabetes," *Diabetes Care*, 2003, 26:252.
Lenard et al., "Central and Peripheral Regulation of Food Intake and Physical Activity: Pathways and Genes," *Obesity*, 2008, 16 (suppl):S11-S22.
Li et al., "Human Receptors for Sweet and Umami Taste,"*Proceedings of the National Academy of Sciences of the United States of America*, 2002, 99(7):4692-4696.
Longer et al., "Bioadhesive Polymers as Platforms for Oral Controlled Drug Delivery III : Oral Delivery of Chlorothiazide Using a Bioadhesive Polymer." *J Pharm Sci*, 1985, 74 :406-411.
Ludwig, DS. "Artificially sweetened beverages: Cause for Concern," *JAMA*. Dec. 9, 2009:302(22):2477-2478.
Mace et al., "Sweet Taste Receptors in Rat Small Intestine Stimulate Glucose Absorption through Apical Glut2," *The Journal of Physiology*, 2007, 582:379-392.
Mainland et al., "Taste Perception: How Sweet It Is (to Be transcribed by You)," *Current Biology: CB*, 2009, 19(15):R655-R656.
Maki et al., "Chronic Consumption of Rebaudioside a, a Steviol Glycoside, in Men and Women with Type 2 Diabetes Mellitus," *Food and Chemical Toxicology: an International Journal Published for the British Industrial Biological Research Association*, 2008, 46:S47-S53.
Mannucci et al., "Effect of Metformin on Glucagon-Like Peptide 1 (Glp-1) and Leptin Levels in Obese Nondiabetic Subjects," *Diabetes Care*, 2001, 24(3): 489-494.
Margolskee et al., "TIR3 and gustducin in gut sense sugars to regulate expression of Na+-glucose cotransporter 1," *PNAS USA*, 2007, 104:15075-15080.
Maruyama et al., "Targeted disruption of G protein-coupled bile acid receptor 1(Gpbarl-M-bar) in mice," *J Endocrinol*, 2006, 191:197-205.
Matsumura et al., "Colocalization of GPR120 with phospholipase Cbeta2 and alpha-gustducin in the taste bud cells in mice." 2009, *Neurosci Lett* 450: 186-190.
Matsunami et al. "A Family of Candidate Taste Receptors in Human and Mouse." *Nature*, 2000, 404:601-604.
Mattes, "Effects of Aspartame and Sucrose on Hunger and Energy Intake in Humans," *Physiology & Behavior*, 1990, 47:1037-1044.
Mattes et al., "Nonnutritive Sweetener Consumption in Humans: Effects on Appetite and Food Intake and Their Putative Mechanisms," *The American Journal of Clinical Nutrition*, 2009, 89:1-14.
Melis et al., "Steviol Effect, a Glycoside of Stevia Rebaudiana, on Glucose Clearances in Rats," *Brazilian Journal of Biology = Revista brasleira de biologia*, 2009, 69(2):371-374.
Mingrone, "Role of the Incretin System in the Remission of Type 2 Diabetes Following Bariatric Surgery," *Nutrition, Metabolism, and Cardiovascular Diseases: NMCD*, 2008, 18:574-579.
Mezitis, et al. *Diabetes Care* 19(9):1004-5 (1996).
Mistili and Spector. "Applications of the Green Fluorescent Protein in Cell Biology and Biotechnology." *Nature Biotech*, 1997, 15:961-964.
Mithieux et al., "Portal Sensing of Intestinal Gluconeogenesis Is a Mechanistic Link in the Diminution of Food Intake Induced by Diet Protein," *Cell Metabolism*, 2005, 2:321-329.
Miyamoto et al. "Acid and Salt Responses in Mouse Taste Cells." *Prog. Neurobiol.*, 2000, 62:135-157.
Mombaerts et al. "Molecular Biology of Odorant Receptors in Vertebrates." *Annu. Rev. Neurosci.*, 1999, 22:487-550.
Moran et al., "Postprandial Ghrelin, Cholecystokinin Peptide Yy, and Appetite before and after Weight Loss in Overweight Women with and without Polycystic Ovary Syndrome," *The American Journal of Clinical Nutrition*, 2007, 86:1603-1610.
Moringo et al., "Glucagon-Like Peptide-1, Peptide Yy, Hunger, and Satiety after Gastric Bypass Surgery in Morbidly Obese Subjects," *The Journal of Clinical Endocrinology and Metabolism*, 2006, 91(5):1735-1740.
Nakagawa et al., "Sweet Taste Receptor Expressed in Pancreatic Beta-Cells Activates the Calcium and Cyclic Amp Signaling Systems and Stimulates Insulin Secretion," *PloS one*, 2009, 4(4):1-11.
Nauli and Zhou. "Polycycstins and MechanosenSation in Renal and Nodal Cilia." *Bioessays*, 2004, 26:844-856.
Neary et al., "Gut Hormones: Implications for the Treatment of Obesity," *Pharmacology & Therapeutics*, 2009, 124:44-56.
Nicolucci et al., "Incretin-based therapies: a new potential treatment approach to overcome clinical inertia in type 2 diabetes," *Acta Biomedica*, 2008, 79(3):184-191.
Niness etal, "Inulin and oligofructose: what are they?" *J Nutr*, 1999, 129:1402S-1406S.
Nofre et al., "Gustatory Responses of Pigs to Sixty Compounds Tasting Sweet to Humans," *Journal of Animal Physiology and Animal Nutrition*, 2002, 86:90-96, Blackwell Wissenschafts-Verlag, Berlin.
Nofre et al., "Evolution of the Sweetness Receptor in Primates. Ii. Gustatory Responses of Non-Human Primates to Nine Compounds Known to Be Sweet in Man," *Chemical Senses*, 1996, 21:747-762.
Oh et al., "GPR120 Is an Omega-3 Fatty Acid Receptor Mediating Potent Anti-inflammatory and Insulin-Sensitizing Effects," 2010, *Cell* 142(5): 687-698.
Olivan et al., "Effect of Weight Loss by Diet or Gastric Bypass Surgery on Peptide Yy3-36 Levels," *Annals of Surgery*, 2009, 249(6):948-953.
Parlevliet et al. "Oxyntomodulin Ameliorates Glucose Intolerance in Mice Fed a High-Fat Diet," *American Journal of Physiology, Endocrinology and Metabolism*, 2007, 294:E142-E147.
Pilpel et al. "The Variable and Conserved Interfaces of Modeled Olfactory Receptor Proteins." *Protein Science*, 1999, 8 :969-977.
Pitcher et al. "G Protein-coliplied Receptor Kinases." *Annu Rev Biochem*, 1998, 67:653-692.
Plaisancie et al., "Release of peptide YY by neurotransmitters and gut hormones in the isolated, vascularly perfused rat colon," *Scand. J. Gastroenterol.*, 1995, 30:568-574.
Plaisancie et al., "Regulation of glucogon-like peptide-1-(7-36)amide secretion by intestinal neurotransmitters and hormones in the isolated vascularly perfused rat colon," *Endocrin*, 1994, 135:2398-2403.
"Prescription Medications for the Treatment of Obesity," NIH Publication No. 07-4191, Dec. 2007.
Pronin et al., "Specific Alleles of Bitter Receptor Genes Influence Human Sensitivity to the Bitterness of Aloin and Saccharin." *Current Biology* 2007, 17(6): 1403-1408.
Ranganath et al., "Attenuated Glp-1 Secretion in Obesity: Cause or Consequence?" *Gut*, 1996, 38:916-919.
Reimann et al., "Glucose Sensing in L Cells: A Primary Cell Study," *Cell Metabolism*, 2008, 8:532-539.
Reimann, "Molecular mechanisms underlying nutrient detection by incretin-secreting cells." *Int Dairy J.* Apr. 2010; 20(4): 236-242.
Robertson et al., "Enhanced Metabolic Cycling in Subjects after Colonic Resection for Ulcerative Colitis," *The Journal of Clinical Endocrinology and Metabolism*, 2005, 90(5):2747-2754.
Rodriguez, et al., "Pilot Clinical Study of an Endoscopic, Removable Duodenal-Jejunal Bypass Liner for the Treatment of Type 2 Diabetes," *Diabetes Technology & Therapeutics*, 2009, 11(11):725-732.
Rogers et al., "Aspartame Ingested without Tasting Inhibits Hunger and Food Intake," *Physiology & Behavior*, 1990, 47(6):1239-1243.
Rogers et al., "Postingestive Inhibition of Food Intake by Aspartame: Importance of Interval Between Aspartame Administration and Subsequent Eating," *Physiology & Behavior*, Mar. 1995, 57(3):489-93.
Rozengurt et al., "Taste Receptor Signaling in the Mammalian Gut," *Current Opinion in Pharmacology*, 2007, 7:557-562.
Rucker et al., "Long Term Pharmacotherapy for Obesity and Overweight: Updated Meta-Analysis," *BMJ*, 2007, 335:1194-1199.
Saltiel, "Fishing Out a Sensor for Anti-inflammatory Oils," 2010, *Cell* 142(5): 672-674.

(56) References Cited

OTHER PUBLICATIONS

Shin et al., "Ghrelin is produced in taste cells and ghrelin receptor null mice show reduced taste responsivity to salty (NaCl) and sour (citric acid) taste," 2010, *PLoSONE* 5(9): e12729.
Simon. "G$\alpha_{15}$ and G$\alpha_{16}$ Couple a Wide Variety of Receptors to Phospholipase C*."*J Biol Chem*, 1994, 270:15175-15180.
Simpson et al., "The Sweetness Inhibitor 'Lactisole' Attenuates Postprandial Hyperglycaemia," *Proceedings of the Nutrition Society*, 2009, 68(OCE), E117.
Soren et al., "Antihiyperglycemic Effects of Stevioside in Type 2 Diabetic Subjects," *Metabolism*, vol. 53, No. 1 Jan. 2004, pp. 73-76.
Staniforth and Baichwal, "TIMERx: novel polysaccharide composites for controlled-programmed release of drugs in the gastrointestinal tract," *Exp Op Drug Del*, 2005, 2(3):587-589.
Steinert et al., "The functional involvement of gut-expressed sweet taste receptors in glucose-stimulated secretion of glucagon-like peptide-1 (GLP-1) and peptide YY (PYY)," *Clinical Nutrition*, 2011, 30:524-532.
Stellman et al., "Artificial Sweetner Use and One-Year Weight Change among Women," *Preventive Medicine*, 1986, 15(2):195-202.
Sternini et al., "Enteroendocrine Cells: A Site of 'Taste' in Gastrointestinal Chemosensing," *Current Opinion in Endocrinology, Diabetes, and Obesity*, 2008, 15:73-75.
Stevens et al. "Hyperpolarization-activated channels HCN1 and HCN4 Mediate Responses to Sour Stimuli." *Nature*, 2001, 413:631-635.
Stock et al., "Ghrelin, Peptide Yy, Glucose-Dependent Insulinotropic Polypeptide, and Hunger Responses to a Mixed Meal in Anorexic, Obese, and Control Female Adolescents," *The Journal of Clinical Endocrinology and Metabolism*, 2005, 90(4):2161-2168.
Strader et al., "Gastronintestinal hormones and food intake," *Gastroenterology*, 2005, 128:175-191.
Strader et al., "Weight Loss through Ileal Transposition is Accompanied by Increased Ileal Hormone Secretion and Synthesis in Rats," *American Journal of Physiology, Endocrinology and Metabolism*, 2005, 288:E447-E453.
Thaler et al., "Minireview: Hormonal and Metabolic Mechanisms of Diabetes Remission after Gastrointestinal Surgery," *Endocrinology*, 2009, 150(6):2518-2525.
The Encyclopedia of Pharmaceutical Technology, Swarbuck and Boylan, Informa Health Care, 1999, pp. 287-308.
Timmermans et al. "Factors'Controlling the Buoyancy and Gastric Retention Capabilities of Floating Matrix Capsules : New Data for Reconsidering the Controversy." *J. Pharm Sci*, 1994, 83:18-24.
Toft-Nielsen et al., "Determinants of the Impaired Secretion of Glucagon-Liek Peptide-1 in Type 2 Diabetes Patients," *J Clin End Met*, 2001, 86(8):3717-3723.
Ugawa et al. "Amiloride-Insensitive Currents of the Acid-Sensing Ion Channel-2a (ASIC2a)-ASIC2b Heteromeric Sour-Taste Reeceptor Channel." *J. Neurosci.*, 2003, 23:3616-3622.
Ugawa et al. "Receptor that Leaves a Sour Taste in the Mouth." *Nature*, 1998, 395:555-556.
Weickert et al., "Cereal fiber improves whole-body insulin sensitivity in overweight and obese women," *Diabetes Care*, 2006, 29:775-780.
Weickert et al., "Soy isoflavones increase preprandial peptide YY (PYY), but have no effect on ghrelin and body weight in healthy postmenopausal women," *J Negative Results in BioMedicine*, 2006, 5:11.
Weintraub et al. "A Double-blind Clinical Trial in Weight Control." *Arch Intern Med*, 1984, 144:1143-1148.
Wilkie et al., "Characterization of G-protein alpha subunits in the G$_Q$ class: Expression in murine tissues and in stromal and hematopoietic cell lines," *PNAS*, 1991, 88:10049-10053.
Xu et al., "Different functional roles of T1R subunits in the heteromeric taste receptors," *PNAS USA*, 2004, 101:14258-14263.
Yang, Q. "Gain weight by 'going diet?' Artificial sweeteners and the neurobiology of sugar cravings," *Neuroscience* 2010, Yale J Biol Med 83(2): 101-108.
Yin et al. "Traditional Chinese Medicine in Treatment of Metabolic Syndrome." *Endocrine, Metabolic & Immune Disorders Drug Targets*, 2008, 8:99-111.
Young et al., "Expression of Taste Molecules in the Upper Gastrointestinal Tract in Humans with and without Type 2 Diabetes," *Gut*, 2009, 58:337-346.
PCT/US10/31793 Search Report and Wiitten Opinion mailed Dec. 28, 2010.
PCT/US10/53257 Search Report and Written Opinion mailed Jul. 15, 2011.
PCT/US10/031793 International Preliminary Report on Patentability (IPRP) mailed Oct. 25, 2011.
Rasmussen, S. "Intestinal absorption of quinine from enteric coated tablets", Acta Pharmacologica et Toxicoligica, 1996, 24(4):331-345.
Reimann, et al. "Glutamine potently stimulates glucagon-like peptide-1 secretion from GLUTag cells", Diabetologia, Springer, Berlin, DE, Sep. 2004, 47(9):1592-1601.
Little, et al. "Sweetness and bitterness taste of meals per se does not mediate gastric emptying in humans", American Journal of Physiology. Regulatory, Intergrative and Comparative Physiology, Sep. 2009, 297(3):R632-R639.
U.S. Appl. No. 61/190,818, filed Sep. 3, 2008, Joseph Fayad.
U.S. Appl. No. 61/480,788, filed Apr. 29, 2011, Joseph Fayad.
U.S. Appl. No. 61/514,174, filed Aug. 2, 2011, Joseph Fayad.
U.S. Appl. No. 61/551,638, filed Oct. 26, 2001, Fayad at el.

* cited by examiner

CHEMOSENSORY RECEPTOR LIGAND-BASED THERAPIES

CROSS-REFERENCE

This application claims the benefit of U.S. Provisional Application No. 61/170,657, filed Apr. 20, 2009 and U.S. application Ser. No. 12/763,926, filed Apr. 20, 2010, all of which are incorporated herein by reference.

BACKGROUND OF THE INVENTION

Despite the longstanding, massive, effort to develop effective treatments for diabetes, metabolic syndrome, obesity, and related metabolic conditions, the number of people worldwide who suffer from them is rapidly growing. These conditions result in numerous medical complications, a lowered quality of life, shortened lifespan, lost work productivity, a strain on medical systems, and a burden on medical insurance providers that translates into increased costs for all.

Type II diabetes treatments in use or development are designed to lower blood glucose levels. They include mimetics of GLP-1 (glucagon-like peptide-1), a hormone that plays a key role in regulating insulin, glucose and hunger. Examples of mimetics are the GLP-1 receptor agonist, Exenatide (Byetta) and the GLP-1 analog Liraglutide. Other drugs inhibit DPP-IV, an enzyme that rapidly degrades endogenous GLP-1. Exenatide is a GLP-1 receptor agonist that is degraded more slowly by DPP-IV. Liraglutide, a GLP-1 analog, is attached to a fatty acid molecule that binds to albumin and slows the rate of GLP-1 release and its degradation. (See, e.g., Nicolucci, et al., 2008, "Incretin-based therapies: a new potential treatment approach to overcome clinical inertia in type 2 diabetes," Acta Biomedica 79(3):184-91 and U.S. Pat. No. 5,424,286 "Exendin-3 and exendin-4 polypeptides, and pharmaceutical compositions comprising same.")

Until very recently obesity treatments include two FDA-approved drugs. Orlistat (Xenical) reduces intestinal fat absorption by inhibiting pancreatic lipase. Sibutramine (Meridia), taken off the market in Europe and the USA, decreases appetite by inhibiting deactivation of the neurotransmitters norepinephrine, serotonin, and dopamine. Undesirable side-effects, including effects on cholesterol levels, have been reported with these drugs. Undesirable side-effects, including effects on cholesterol levels, have been reported with these drugs. (See, e.g., "Prescription Medications for the Treatment of Obesity," NIH Publication No. 07-4191, December 2007). Surgical treatments including gastric bypass surgery and gastric banding are available, but only in extreme cases. These procedures can be dangerous, and furthermore are not appropriate options for patients with more modest weight loss goals.

Certain intestinal cells, L cells, have been reported to produce GLP-1 in response to glucose, fat and amino acid stimulation. These and other such "enteroendocrine cells" also produce other hormones involved in processes relating to glucose and fuel metabolism, including oxyntomodulin, reported to ameliorate glucose intolerance and suppress appetite, PYY (peptide YY), also observed to suppress appetite, CCK (cholecystokinin), which reportedly stimulates the digestion of fat and protein and also reduces food intake, GLP-2, which reportedly induces gut cell proliferation, and GIP (gastric inhibitory polypeptide, also called glucose-dependent insulinotropic peptide), an incretin secreted from the intestinal K cells that has been observed to augment glucose-dependent insulin secretion. (See, e.g., Jang, et al., 2007, "Gut-expressed gustducin and taste receptors regulate secretion of glucagon-like peptide-1," PNAS 104(38):15069-74 and Parlevliet, et al., 2007, "Oxyntomodulin ameliorates glucose intolerance in mice fed a high-fat diet," Am J Physiol Endocrinol Metab 294(1):E142-7).

It has also been reported that there are taste receptor-like elements present on the L-cells and K-cells in the intestine (Hofer, et al., 1996, "Taste receptor-like cells in the rat gut identified by expression of alpha-gustducin" Proc Natl Acad Sci USA 93:6631-6634). For example, the sweet taste receptors are heterodimers of the T1R2 and T1R3 GPCRs and have been proposed to be identical to those sweet taste receptors found on taste buds. The umami receptors are reported to be T1R1 and T1R3 heterodimers (Xu, et al., 2004, "Different functional roles of T1R subunits in the heteromeric taste receptors," Proc Natl Acad Sci USA 101: 14258-14263 and Sternini, et al., 2008, "Enteroendocrine cells: a site of 'taste' in gastrointestinal chemosensing," Curr Opin Endocrinol Diabetes Obes 15: 73-78). Stimulation of taste or taste-like receptors by luminal nutrients has resulted in apical secretion of L-cell products such as GLP-1, PYY, oxyntomodulin and glycentin, and K-cell products such as GIP, and into the portal vein (Jang, et al., 2007, PNAS 104(38):15069-74). In a glucose-dependent manner, GLP-1 and GIP increase insulin release from beta cells (an effect known as the incretin effect). In addition, GLP-1 inhibits glucagon release and gastric emptying. GLP-1, oxyntomodulin and PYY 3-36 are considered to be satiety signals (Strader, et al., 2005, "Gastrointestinal hormones and food intake," Gastroenterology 128: 175-191). Receptors for fatty acids (e.g., GPR40 and/or GPR120) (Hirasawa, et al., 2005, Free fatty acids regulate gut incretin glucagon-like peptide-1 secretion through GPR120, Nat Med 11: 90-94) and bile acids (e.g., Gpbar1/M-Bar/TGR5) (Maruyama, et al., 2006, "Targeted disruption of G protein-coupled bile acid receptor 1 (Gpbar1/M-Bar) in mice." J Endocrinol 191: 197-205 and Kawamata, et al., 2003, "A G protein-coupled receptor responsive to bile acids," J Biol Chem 278: 9435-9440) are also present in enteroendocrine cell lines. There are also a large number of over 50 T2Rs along with a large number of haplotypes which comprise bitter receptors. The putative sour and salty receptors, which likely include ion channels, have not been completely characterized in humans. See, e.g., Chandrashekar et al., 2010, "The cells and peripheral representation of sodium taste in mice," Nature 464(7286): 297-301. Although it has been proposed that ablation of certain taste cells resulted in loss of behavior response to only sour stimuli, no specific taste behavior tests were performed. Thus, the status of identification of a sour receptor is unclear. See, e.g., Shin et al., "Ghrelin is produced in taste cells and ghrelin receptor null mice show reduced taste responsivity to salty (NaCl) and sour (citric acid) taste," 2010, PLoSONE 5(9): e12729. GP120, a GPCR corresponding to an fatty acid receptor, has also been identified in the taste buds of mice and, furthermore, ω3 fatty acids have been shown to mediate anti-inflammatory effects and reverse insulin resistance in obese mice via their actions on GP120 present in macrophages. See, e.g., Oh et al., "GPR120 Is an Omega-3 Fatty Acid Receptor Mediating Potent Anti-inflammatory and Insulin-Sensitizing Effects," 2010, Cell 142(5): 687-698; Satiel, "Fishing Out a Sensor for Anti-inflammatory Oils," 2010, Cell 142(5): 672-674; also see Matsumura et al., "Colocalization of GPR120 with phospholipase Cbeta2 and alpha-gustducin in the taste bud cells in mice," 2009, Neurosci Lett 450: 186-190.

SUMMARY OF THE INVENTION

Provided herein are compositions having at least one chemosensory receptor ligand and methods of treatment using the compositions. Diseases and conditions to be treated with the compositions described herein include metabolic syndrome, insulin resistance, diabetes type I, diabetes type II, diabetes-associated conditions, obesity, glucose intolerance, gestational diabetes mellitus (GDM), dyslipidemia, postprandial dyslipidemia, inflammatory bowel disease (IBD), including ulcerative colitis and Crohn's disease, irritable bowel syndrome (IBS), short bowel syndrome, polycystic ovary syndrome (PCOS), non-alcoholic fatty liver disease (NAFL), non-alcoholic steatohepatitis (NASH), anorexia, food addiction, food craving, binge eating, weight loss, depression, and mood disorders. Also provided herein are compositions of at least one chemosensory receptor ligand and an optional metabolite.

The compositions described herein can be delivered to the upper or small intestine, to the lower or large intestine, or both. Administration of the compositions into the intestine is via any known method including oral.

In one aspect, the compositions described herein are adapted to release a therapeutically effective amount of a chemosensory ligand to one or more regions of the intestine. In some embodiments, the compositions described herein further release at least some of the chemosensory receptor ligand in the stomach. In some embodiments, the compositions are adapted to release in the duodenum, jejunum, ileum, caecum, colon and/or rectum. In other embodiments, the compositions are adapted to release in the jejunum, ileum, caecum, colon and/or rectum. In some embodiments, the composition is formulated for release in the lower intestine. In further embodiments, the composition is formulated for release in the upper intestine. In still further embodiments, the composition is formulated for release in the upper intestine and lower intestine.

Also provided herein are compositions having at least one chemosensory receptor ligand wherein the composition has a sweetness potency of at least about 100 times the sweetness potency of sucrose, and wherein the composition is adapted to release the ligand to one or more regions of the intestine of a subject. In one embodiment, the composition has a sweetness potency of at least about 500 times the sweetness potency of sucrose. In one embodiment, the composition has a sweetness potency of at least about 1000 times the sweetness potency of sucrose.

Also provided herein are compositions having at least one chemosensory receptor ligand wherein the composition has a sweetness potency equivalent to at least about 500 grams of sucrose, and wherein the composition is adapted to release the ligand to one or more regions of the intestine of a subject. In one embodiment, the composition has a sweetness potency equivalent to at least about 5000 grams of sucrose. In one embodiment, the composition has a sweetness potency equivalent to at least about 10000 grams of sucrose.

In one embodiment, a composition releases a chemosensory receptor ligand at an onset of about 5 to about 45 minutes, about 105 to about 135 minutes, about 165 to about 195 minutes or about 225 to about 255 minutes, or a combination of times thereof following oral administration to a subject.

In other embodiments, a composition releases a chemosensory receptor ligand at an onset of about pH 5.0, about pH 5.5, about pH 6.0, about pH 6.5, about pH 7.0, or combination thereof following oral administration to a subject.

In certain embodiments, one or more chemosensory receptor ligands is selected from a sweet receptor ligand, a bitter receptor ligand, an umami receptor ligand, a fat receptor ligand, a bile acid receptor ligand, or any combination thereof. Sweet receptor ligands include glucose, sucralose, aspartame, Stevioside, Rebaudioside, Neotame, acesulfame-K, and saccharin. Bitter receptor ligands include flavanones, flavones, flavonols, flavans, phenolic flavonoids, isoflavones, limonoid aglycones, glucosinolates or hydrolysis product thereof, and organic isothiocyanates. Umami receptor ligands include glutamate salts, glutamines, acetyl glycines, or aspartame. Fat receptor ligands include linoleic acids, oleic acids, palmitates, oleoylethanolamides, mixed fatty acid emulsion, omega-3 fatty acids and N-acylphosphatidylethanolamine (NAPE). Bile acids include deoxycholic acids, taurocholic acids and chenodeoxycholic acids. In certain embodiments, the chemosensory receptor ligand is nonmetabolized. In certain embodiments, the chemosensory receptor ligand is an agonist. In certain embodiments, the chemosensory receptor ligand is an enhancer.

The compositions described herein can be formulated with an enteric coating. In some embodiments, the composition has an enteric coating. In another aspect, the compositions described herein can be formulated with a modified release system. In yet another aspect, the compositions described herein can be formulated with a timed release system. In a further aspect, the compositions described herein can be formulated with a modified release and enteric coating. In yet a further aspect, the compositions described herein can be formulated with a timed release and enteric coating.

Provided herein is a method of treating a condition associated with a chemosensory receptor in a subject comprising administering a composition described herein to the subject. In one aspect, the composition comprises at least one chemosensory receptor ligand to the subject. In another aspect, the composition is adapted to release a therapeutically effective amount of a chemosensory ligand to one or more regions of the intestine.

Provided herein is a method of treating a condition associated with a chemosensory receptor in a subject by administering a composition comprising at least two chemosensory receptor ligands to the subject.

Provided herein is a method of treating a condition associated with a chemosensory receptor in a subject by administering a composition comprising at least one chemosensory receptor ligand and a cognate metabolite. In some embodiments, the metabolite is administered after the administration of the chemosensory receptor ligand. In another embodiment, the metabolite is co-administered with the chemosensory receptor ligand. In further embodiments, the chemosensory receptor ligand is co-administered with the ingestion of food by the subject or the chemosensory ligand is administered before the subject ingests food. In certain instances, food itself may comprise one or more chemosensory receptor ligands. In certain instances, food itself may serve as a metabolite.

Provided herein is a method of treating a condition associated with a chemosensory receptor by administering a composition having at least one chemosensory receptor ligand to the lower intestine of a subject. In another embodiment, the composition comprising at least one chemosensory receptor ligand is administered to the upper intestine of a subject. In yet another embodiment, the composition comprising at least one chemosensory receptor ligand is administered to the upper intestine and lower intestine of a subject. In certain instances, chemosensory receptor ligand in the upper intestine and lower intestine is the same chemosensory receptor ligand. In certain instances, chemosensory receptor ligand in the upper intestine and lower intestine is different chemosensory receptor ligands.

Provided herein is a method of treating a condition associated with a chemosensory receptor by administering a composition having at least one chemosensory receptor ligand to the duodenum, jejunum, ileum, caecum, colon and/or rectum. In other embodiments, the composition comprising at least one chemosensory receptor ligand is administered to the duodenum of a subject. In another embodiment, the composition comprising at least one chemosensory receptor ligand is administered to the jejunum of a subject. In another embodiment, the composition comprising at least one chemosensory receptor ligand is administered to the ileum of a subject. In another embodiment, the composition comprising at least one chemosensory receptor ligand is administered to the caecum of a subject. In another embodiment, the composition comprising at least one chemosensory receptor ligand is administered to the colon of a subject. In another embodiment, the composition comprising at least one chemosensory receptor ligand is administered to the rectum of a subject. In another embodiment, the composition comprising at least one chemosensory receptor ligand is administered to the duodenum, jejunum, ileum, caecum, colon and/or rectum of a subject. In yet another embodiment, the composition releases at least some of the chemosensory receptor ligand into the stomach.

Provided herein is a method of treating a condition associated with a chemosensory receptor by administering one or more chemosensory receptor ligand compositions that release at an onset about 5 to about 45 minutes, about 105 to about 135 minutes, about 165 to about 195 minutes, about 225 to about 255 minutes or a combination of times thereof following oral administration to a subject.

Provided herein is a method of treating a condition associated with a chemosensory receptor by administering one or more chemosensory receptor ligand compositions that have an onset of release at about 10 minutes, about 30 minutes, about 120 minutes, about 180 minutes, about 240 minutes or a combination of times thereof following oral administration to a subject. In one embodiment, the composition releases at an onset of about 10 minutes following administration to a subject. In one embodiment, the composition releases at an onset of about 30 minutes following administration to a subject. In one embodiment, the composition releases at an onset of about 120 minutes following administration to a subject. In one embodiment, the composition releases at an onset of about 180 minutes following administration to a subject. In one embodiment, the composition releases at an onset of about 240 minutes following administration to a subject. In one embodiment, the composition releases at an onset of about 10 minutes, 30 minutes, about 120 minutes, about 180 minutes and about 240 minutes following oral administration to a subject.

Provided herein is a method of treating a condition associated with a chemosensory receptor by administering a one or more chemosensory receptor ligand compositions that has an onset of release at about pH 5.5, about pH 6.0, about pH 6.5, and/or about pH 7.0.

Provided herein is a method of treating a condition associated with a chemosensory receptor by administering one or more compositions having at least one chemosensory receptor ligand wherein the compositions release at an onset of two different pH ranges, wherein said two pH ranges are selected from about pH 5.0 to about pH 6.0, about pH 6.0 to about pH 7.0 and about pH 7.0 to about pH 8.0.

In certain embodiments of the methods described herein, one or more chemosensory receptor ligand is selected from a sweet receptor ligand, a bitter receptor ligand, an umami receptor ligand, a fat receptor ligand, a bile acid receptor ligand, or any combination thereof. Sweet receptor ligands include glucose, sucralose, aspartame, Stevioside, Rebaudioside, Neotame, acesulfame-K, and saccharin. Bitter receptor ligands include flavanones, flavones, flavonols, flavans, phenolic flavonoids, isoflavones, limonoid aglycones, glucosinolates or hydrolysis product thereof, and organic isothiocyanates. Umami receptor ligands include glutamate salts, glutamines, acetyl glycines, or aspartame. Fat receptor ligands include linoleic acids, oleic acids, palmitates, oleoylethanolamides, mixed fatty acid emulsion, omega-3 fatty acids and N-acylphosphatidylethanolamine (NAPE). Bile acids include deoxycholic acids, taurocholic acids and chenodeoxycholic acids. In certain embodiments, the chemosensory receptor ligand is nonmetabolized. In certain embodiments, the chemosensory receptor ligand is an agonist. In certain embodiments, the chemosensory receptor ligand is an enhancer.

Provided herein is a method of modulating the hormonal profile of lower intestine by administering a composition having at least one chemosensory receptor ligand to the lower intestine of a subject. In one embodiment, the hormonal profile is that of GLP-1, Oxyntomodulin, and Peptide YY.

Provided herein is a method of modulating the hormonal profile of upper intestine by administering a composition having at least one chemosensory receptor ligand to the upper intestine of a subject. In one embodiment, the hormonal profile is that of GLP-1, GLP-2, Oxyntomodulin, Peptide YY, GIP, Insulin C Peptide, glucagon, insulin, cholecystokinin (CCK), or any combination thereof.

Further provided herein is a method to sensitize lower intestinal chemosensory receptors by stimulating chemosensory receptors in the upper intestine.

Provided herein are methods of treating conditions associated with a chemosensory receptor with the compositions described herein. Conditions associated with a chemosensory receptor include metabolic syndrome, insulin resistance, diabetes type I, diabetes type II, obesity, binge eating, undesired food cravings, food addiction, a desire to reduce food intake or to lose weight or maintain weight loss, anorexia, glucose intolerance, gestational diabetes mellitus (GDM), dyslipidemia, post-prandial dyslipidemia, bone loss disorders, osteopenia, osteoporosis, muscle wasting disease, muscle degenerative disorders, polycystic ovary syndrome (PCOS), non-alcoholic fatty liver disease (NAFL), non-alcoholic steatohepatitis (NASH), depression, a mood disorder, immune disorders of the gut (e.g., celiac disease), bowel irregularity, irritable bowel syndrome (IBS) and inflammatory bowel disease (IBD) including ulcerative colitis, Crohn's disease, and short bowel syndrome. In some embodiments, the condition is obesity. In other embodiments, the condition is diabetes. In further embodiments, the subject is undergoing bariatric surgery. In yet other embodiments, methods provided herein further include administering a drug for diabetes or obesity.

Also provided herein are methods for treating a disease, disorder or defect in energy homeostasis in a subject comprising administering a composition described herein. In one aspect, the composition is adapted to release a therapeutically effective amount of a chemosensory ligand to one or more regions of the intestine.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

The present invention relates to methods and compositions for treating conditions associated with a chemosensory receptor, for example, metabolic conditions including obesity and diabetes, using a ligand or combination of ligands that stimulates chemosensory receptors present on cells lining the gut. Binding of ligand(s) to these chemosensory receptors modulates the production of hormone molecules, e.g., GLP-1, GLP-2, oxyntomodulin, PYY, GIP, insulin C peptide, glycentin, glucagon, and/or CCK that are key regulators of energy and metabolic processes such as glucose metabolism. The specific hormone(s) produced vary depending on the receptor(s) stimulated. Chemosensory receptor ligands include receptor ligands that are metabolizable or can be metabolized as an energy source, e.g. food or metabolites, as well as receptor ligands that are nonmetabolized, e.g. tastants. Nonmetabolized chemosensory receptor ligands, as used herein, include ligands that are not substantially metabolized, i.e., ligands having insignificant caloric value.

In some embodiments, one or more nonmetabolized chemosensory receptor ligands are used to modulate the secretion of hormone molecules and regulate metabolic processes. In other embodiments, a nonmetabolized chemosensory receptor ligand(s) is combined with a metabolized or metabolizable chemosensory receptor ligand(s). It is contemplated that the addition of one or more metabolized chemosensory receptor ligands along with activation of the enteroendocrine cell chemosensory receptors by a nonmetabolized chemosensory receptor ligand(s), may result in enhanced stimulation of hormone release.

The present embodiments described herein additionally contemplate targeting administration of chemosensory receptor ligands to specific sites throughout the gut. Enteroendocrine cells, e.g., L cells, K cells, and I cells, that each secrete a different set of metabolic hormones in response to chemosensory stimulation, occur throughout the length of the intestine. The concentrations and proportions of these enteroendocrine cell types are different in the various intestinal segments, and, as noted above, each cell type has a different metabolic hormone expression profile. Targeted administration of the compositions of the invention to specific intestinal segments, for example, through the use of formulations designed for release within one or more desired segments of the intestine, provides an additional level of control over the effect of such compositions, e.g., in the modulation of hormones involved in metabolism.

The present embodiments described herein thus include a novel approach to treating important chemosensory receptor-associated conditions by, for example, modulating the secretion of metabolic hormones through enteroendocrine chemosensory receptor activation. The embodiments further include the capability to select combination therapies tailored to the specific needs of individuals having varying hormone profiles.

Chemosensory Receptors

Mammalian chemosensory receptors and ligands are discussed, e.g., in U.S. Pat. App. Pub. Nos. 2008/0306053 and 2008/0306093, both titled "Modulation of Chemosensory Receptors and Ligands Associated Therewith," and U.S. Pat. No. 7,105,650, titled "T2R taste receptors and genes encoding same." Complete or partial sequences of numerous human and other eukaryotic chemosensory receptors are currently known (see, e.g., Pilpel, Y. et al., Protein Science, 8:969 77 (1999); Mombaerts, P., Annu Rev. Neurosci., 22:487 50 (1999); EP0867508A2; U.S. Pat. No. 5,874,243; WO 92/17585; WO 95/18140; WO 97/17444; WO 99/67282).

Sweet and Umami Receptors: In humans, different combinations of the T1Rs, a family of class C G-protein-coupled receptors, respond to sweet and umami taste stimuli. T1R2 and T1R3 reportedly recognize sweet taste stimuli. The T1R subunits that comprise the heteromeric sweet and umami taste receptors are described by, e.g., Xu, et al., 2004, Proc Natl Acad Sci USA 101: 14258-14263. Xu, et al., report that aspartame and neotame require the N-terminal extracellular domain of T1R2, G protein coupling requires the C-terminal half of T1R2, and that cyclamate and lactisole, a sweet receptor inhibitor, require the transmembrane domain of T1R3. Their results suggest the presence of multiple sweetener interaction sites on this receptor.

T1R1 and T1R3 recognize umami taste stimulus L-glutamate. This response is reportedly enhanced by 5' ribonucleotides (Xu, et al., 2004).

Bitter Receptors: Bitter chemicals are detected by around 50 T2R receptor (GPCR) family members (Adler et al., 2000, Cell 100:693-702; Chandrashekar et al., 2000, Cell 100:703-711; Matsunami et al., 2000, Nature 404:601-604). Certain T2Rs and methods for expressing them are described in, e.g., U.S. Pat. App. Pub. No. 2008/0306053 and U.S. Pat. No. 7,105,650. Haplotypes of many of the bitter receptor have also been identified which confer differences in the sensitivity of individuals to particular bitter tastant (Pronin et al., 2007, Current Biology 17(6): 1403-1408).

Bile Receptors: There are multiple bile acid receptors. The bile acid receptor having subunits Gpbar1 and M-Bar is reportedly involved in the influence of bile acids on fat solubilization, cholesterol maintenance, and bile acid homeostasis (Maruyama, et al., 2006, J. Endocrinol. 191, 197-205). Maruyama, et al., report a possible role for Gpbar in energy homeostasis. Kawamata, et al. ("A G protein-coupled receptor responsive to bile acids" J. Biol. Chem. 278, 9435-9440, 2003), report a possible role for bile acid receptor TGR5 in the supression of macrophage function.

Sour and Salty Taste Receptors: A number of candidate receptors and transduction mechanisms for sensing sour and salty taste have been proposed (Miyamoto et al., 2000, Prog. Neurobiol. 62:135-157). For example, acid-sensing ion channel-2 (ASIC2) is proposed to function as a sour receptor in the rat (Ugawa et al, 2003, J. Neurosci. 23:3616-3622; Ugawa et al., 1998, Nature 395:555-556). HCN1 and HCN4, members of hyperpolarization-activated cyclic nucleotide gated channels (HCNs) are also candidate sour receptor channels (Stevens et al., 2001, Nature 413:631-635). Among TRP channel families, members of the PKD family (polycystic kidney disease, also called TRPP or polycystins) have been reported to possess unique properties (Delmas et al., 2004, Biochem. Biophys. Res. Commun. 322:1374-1383; Nauli and Zhou, 2004, Bioessays 26:844-856). Two TRP channel members, PKD 1L3 (Genbank Accession Nos. AY164486, murine, nucleic acid, AAO32799 murine, amino acid, AY1 64485, human, nucleic acid, and AAO32798, human, amino acid), and PKD2L1 (Genbank Accession Nos. NM_181422, murine, nucleic acid, NP_852087, murine, amino acid, NM_016112, human, nucleic acid and NP_057196, human, amino acid, are reportedly specifically expressed in a subset of taste receptor cells that do not correspond to bitter, sweet or umami sensing cells. The proteins are localized at the apical tip of taste cells where tastants are detected. PKD and PKD2L1 heteromer formation is required for functional cell surface expression and whenever PKD1L3 and PKD2L1 are expressed in heterologous cells they are activated by sour solutions. Therefore, it is contemplated PKD 1L3 and PKD2L1 function together as sour taste receptors in mammals, although an understanding of the mechanism is not necessary to practice the present invention and the present invention is not limited to any particular mechanism of action.

Fat Receptors: Fat receptor or fatty acid receptor as used herein means any transporter receptor or other molecule that binds to fats and/or fatty acids that are ingested. Chemosensory receptors for fat have not been well characterized, though there is possible involvement of fatty acid transport proteins known to be present in the gastrointestinal tract. The mouse fatty acid transporter protein CD36 has been reported to be a potential fat taste receptor (Laugerette, et al., 2005, "CD36 involvement in orosensory detection of dietary lipids, spontaneous fat preference, and digestive secretions," Journal of Clinical Investigation 115(11): 3177-84). In rat, CD36 has been found to be expressed at higher levels in proximal than distal intestinal mucosa (Chen, et al., 2001, "Gut expression and regulation of FAT/CD36: possible role in fatty acid transport in rat enterocytes," Am J Physiol Endocrinol Metab. 281(5):E916-23). More recently, a number of GPCRs which were previously classified as orphan receptors have been shown to respond to lipid ligands, including fatty acids and several have been identified as candidates for fat receptors in taste.

When a ligand binds to a GPCR, the receptor presumably undergoes a conformational change leading to activation of the G Protein. G Proteins are comprised of three subunits: a guanyl nucleotide binding α subunit, a β subunit, and a γ subunit. G Proteins cycle between two forms, depending on whether GDP or GTP is bound to the α subunit. When GDP is bound, the G Protein exists as a heterotrimer: the Gαβγ complex. When GTP is bound, the α subunit dissociates from the heterotrimer, leaving a Gβγ complex. When a Gαβγ complex operatively associates with an activated G Protein-Coupled Receptor in a cell membrane, the rate of exchange of GTP for bound GDP is increased and the rate of dissociation of the bound Gα subunit from the Gαβγ complex increases. The free Gα subunit and Gβγ complex are thus capable of transmitting a signal to downstream elements of a variety of signal transduction pathways. These events form the basis for a multiplicity of different cell signaling phenomena, including for example the signaling phenomena that are identified as neurological sensory perceptions such as taste and/or smell. (See, e.g., U.S. Pat. No. 5,691,188.) GP120, a GPCR corresponding to an fatty acid receptor, has also been identified in the taste buds of mice and, furthermore, ω3 fatty acids have been shown to mediate anti-inflammatory effects and reverse insulin resistance in obese mice via their actions on GP120 present in macrophages (Oh et al., 2010, Cell 142(5): 687-698; Satiel, Cell 142(5): 672-674; also see Matsumura et al., 2009, Neurosci Lett 450: 186-190).

Hormones

The embodiments described herein include compositions and methods for modulating the levels of circulating enteroendocrine cell hormones, including, but not limited to, GLP-1, GLP-2, GIP, oxyntomodulin, PYY, cholecystokinin (CCK), glycentin, insulin, glucagon, insulin C peptide, ghrelin, etc., such compositions and methods comprising administering at least one chemosensory receptor ligand to a subject to treat a condition associated with a chemosensory receptor. Hormone modulation can be achieved by administering a composition comprising a chemosensory receptor ligand, including an agonist, antagonist, modifier, enhancer or combination thereof acting on a sweet-taste receptor, an umami receptor, a bitter receptor, a fatty acid receptor, and/or a bile acid receptor.

In particular embodiments, a combination of one or more agonists of the sweet, umami, bitter, free fatty acid, and bile acid receptors will simulate the synchronous release of important hormones and neural signals from the enteroendocrine cells and thus facilitate the assimilation and disposition of meal nutrients. In additional embodiments, a combination of one or more agonists of the sweet, umami, bitter, free fatty acid, and bile acid receptors suppresses ghrelin synthesis, activity or action, or its post-translational modification (Ghrelin Octonoyl Acyl Transferase activity or GOAT) and/or ghrelin secretion or release from oxyntic cells in the stomach. It is important to note that some of these hormones may not exhibit major effects when administered alone but may perform additively and/or synergistically when released together. For example, PYY 3-36 as a single therapy has disappointed in the clinic (Nastech Press Release). Therefore, in embodiments the invention provides coordinate and synchronous release of gut hormones in concert while not ascribing a specific activity to merely a single hormone. Enteroendocrine cell (e.g., L cells, K cells and I cells) stimulation by nutrients reportedly alters release of one or more of the following known hormones: GLP-1, GLP-2, GIP, oxyntomodulin, PYY, CCK, insulin, glucagon, insulin C peptide, glycentin, ghrelin. Nutrients may also alter release of yet-to-be-characterized hormones released from enteroendocrine cells. This modulation in hormone release can result in beneficial therapeutic effects, for example, better glucose control in the treatment of diabetes and related disorders (prediabetes, polycystic ovary disease), inflammatory bowel disorders, bowel damage and osteoporosis (e.g., through the release of GLP-2), lowering of circulating lipids in the treatment of hyperlipidemia, fatty liver disease, and reduced food intake and the regulation of energy homeostasis in the treatment of obesity (weight loss). Administering a combination of one or more agonists of the sweet, umami, bitter, free fatty acid, and bile acid receptors components along with a DPP-IV inhibitor can increase the therapeutic effect, since GLP-1, PYY, GLP-2 and GIP are rapidly eliminated by DPP-IV.

In vivo results consistent with the use of sweet, umami, free fatty acid, and bile acid receptors to increase GLP-1 levels include:

The release of GLP-1 was reported during intraduodenal glucose delivery in humans. (See, e.g., Kuo, et al., 2008, "Transient, early release of glucagon-like peptide-1 during low rates of intraduodenal glucose delivery," Regul Pept 146, 1-3.)

An increase in postprandial GLP-1 levels was observed after administration of the alpha-glucosidase inhibitor miglitol in humans. (See, e.g., Lee, et al., 2002, "The effects of miglitol on glucagon-like peptide-1 secretion and appetite sensations in obese type 2 diabetics," Diabetes Obes Metab 4, 329-335.)

In rats, the increase in GLP-1 after administration of miglitol was synergistic with administration of a DPP-IV inhibitor (Goto et al., 2008, Poster P-470 ADA).

Inulin-type fructans (non-digestible fructose polymers) reportedly stimulated GLP-1 secretion. (See, e.g., Delzenne, et al., 2007, "Modulation of glucagon-like peptide 1 and energy metabolism by inulin and oligofructose: experimental data," J Nutr 137, 2547S-2551S and Niness, et al., 1999, "Inulin and oligofructose: what are they?" J Nutr 129, 1402S-1406S.)

Administration of glutamate, an umami agonist, to rats resulted in decreased weight gain and reduced abdominal fat. (See, e.g., Kondoh, et al., 2008, "MSG intake suppresses weight gain, fat deposition, and plasma leptin levels in male Sprague-Dawley rats," Physiol Behav 95, 135-144.)

Oral administration of free fatty acids to mice resulted in increased portal and systemic GLP-1 concentrations. (See, e.g., Hirasawa, et al., 2005, "Free fatty acids regulate gut incretin glucagon-like peptide-1 secretion through GPR120," Nat Med 11, 90-94.)

G protein-coupled bile acid receptor 1 deficient mice showed significantly higher fat accumulation and weight gain relative to control mice. (See, e.g., Maruyama, et al., 2006, cited above.)

In vivo studies with rat jejunum perfused with sucralose and glutamate showed that sweet and umami receptors regulate glucose, peptide and glutamate absorption. (See, e.g., Mace, et al., 2008, "An energy supply network of nutrient absorption coordinated by calcium and T1R taste receptors in rat small intestine," J. Physiol.)

Bile acids provided to humans via rectal administration caused release of PYY. (See, e.g., Adrian, et al., 1993, "Deoxycholate is an important releaser of peptide YY and enteroglucagon from the human colon," Gut 34(9):1219-24.)

While there are reports of metabolized ligands to the various chemosensory receptors having effects to release gut hormones, it has been reported that nonmetabolized chemosensory receptor ligands may not effect gut hormone release. Frank Reimann. Molecular mechanisms underlying nutrient detection by incretin-secreting cells." Int Dairy J. 2010 April; 20(4): 236-242. doi: 10.1016/j.idairyj.2009.11.014.

For example, instillation of sucralose (a nonmetabolized sweetener) into the duodenum of humans reportedly had no effect on gut hormone release while instillation of metabolized sugars did. Ma J, et al., "Effect of the artificial sweetener, sucralose, on gastric emptying and incretin hormone release in healthy subjects," CK Am J Physiol Gastrointest Liver Physiol. 2009 April; 296(4):G735-9. Epub 2009 Feb. 12. Other studies in rats reportedly showed no effect of the nonmetabolized sweeteners, sucralose and stevia, to cause gut hormone release, while dextrose did have an effect. Fujita Y, et al., "Incretin Release from Gut is Acutely Enhanced by Sugar but Not by Sweeteners In Vivo," Am J Physiol Endocrinol Metab. 2008 Dec. 23. [Epub ahead of print]; Reimann F., et al., "Glucose sensing in L-cells: a primary cell study," Cell Metabolism. 2008; 8:532-539. Other reports in humans reported no alterations of gut hormones in the circulation after administration of stevia or rebaudioside A, which are both nonmetabolized sweeteners. Gregersen, S., et al., "Antihyperglycemic Effects of Stevioside in type 2 diabetic subjects," 73 Metabolism, Vol 53, No 1 (January), 2004: pp 73-76.

Additionally, reports in humans or animals have suggested that non-nutritive sweeteners may not cause weight loss. See e.g., Maki, K. C., et al., "Chronic consumption of rebaudioside A, a steviol glycoside, in men and women," Food Chem. Toxicol. 2008 July; 46 Suppl 7:S47-53. Epub 2008 May 16; Yang, Q. "Gain weight by 'going diet?'" Artificial sweeteners and the neurobiology of sugar cravings," Neuroscience 2010. Yale J Biol Med. 2010 June; 83(2):101-8; Ludwig, D S, "Artificially sweetened beverages: cause for concern," JAMA. 2009 Dec. 9; 302(22):2477-8). Other reports suggest that non-nutritive sweeteners may be instrumental in causing weight gain or effects on hunger or satiety. Richard Mattes. Effects of Aspartame and Sucrose on Hunger and Energy Intake in Humans. Physiology & Behavior, Vol. 47, pp. 1037-1044. Effects of Aspartame and Sucrose on Hunger and Energy Intake in Humans.

Chemosensory Receptor Ligands

Chemosensory receptor ligands include metabolized chemosensory receptor ligands that can be metabolized as an energy source, e.g. food or metabolites, as well as nonmetabolized chemosensory receptor ligands that are not metabolized as an energy source, e.g. tastants. The term nonmetabolized chemosensory receptor ligands, as used herein, includes chemosensory receptor ligands that are metabolized to a small degree but are not metabolized substantially. That is, nonmetabolized chemosensory receptor ligand includes ligands that have insignificant caloric value. Chemosensory receptor ligands include agonists, antagonists, modifiers, and enhancers as well as other compounds that modulate chemosensory receptors. Many chemosensory receptor ligands are known in the art and have been reported in the literature.

Non-limiting examples of umami receptor ligands include glutamate salts, glutamines, acetyl glycines, and aspartame. Many more umami receptor ligands other than those listed herein and in the cited manuscripts, are known to those of skill in the art, and still more can be identified using methods known in the art and described herein.

Non-limiting examples of fat receptor ligands include linoleic acids, oleic acids, palmitates, oleoylethanolamides, omega-3 fatty acids, mixed fatty acid emulsion, and N-acylphosphatidylethanolamine (NAPE), myristoleic acid, palmitoleic acid, alpha-linolinic acid, arachidonic acid, eicosapentaenoic acid, erucic acid, and docosahexaenoic acid. Many more fat receptor ligands other than those listed herein and in the cited manuscripts, are known to those of skill in the art, and still more can be identified using methods known in the art and described herein.

Bile acids include cholic acids, deoxycholic acids, taurocholic acids and chenodeoxycholic acids. Many more bile acid receptor ligands other than those listed herein and in the cited manuscripts, are known to those of skill in the art, and still more can be identified using methods known in the art and described herein.

Non-limiting bitter receptor ligands include flavanones, flavones, flavonols, flavans, phenolic flavonoids, isoflavones, limonoid aglycones, glucosinolates or hydrolysis product thereof, caffeine, quinine, extracts of *Momordica charantia* (bitter melon), and isothiocyanates. Certain bitter tastants are described, e.g., in Drewnowski and Gomez-Carneros, American Journal of Nutrition, 72 (6): 1424 (2000). Many more bitter receptor ligands other than those listed herein and in the cited manuscripts, are known to those of skill in the art, and still more can be identified using methods known in the art and described herein. Exemplary bitter phytonutrients in common plant foods that can be bitter receptor ligands are listed in the following table.

| Phytonutrient class | Typical component | Taste quality | Food source |
| --- | --- | --- | --- |
| Phenolic compounds | | | |
| Flavanones | Naringin | Bitter | Grapefruit, flavedo |
| | | | Grapefruit, albedo |
| | | | Grapefruit, pith |
| | | | Grapefruit, seeds |
| | | | Immature grapefruit |
| | | | Grapefruit juice |
| | | | Oroblanco juice |
| | | | Melogold juice |

-continued

| Phytonutrient class | Typical component | Taste quality | Food source |
|---|---|---|---|
| Flavones | Tangeretin | Bitter | Orange fruit |
| | | | Orange juice |
| | | | Juice from concentrate |
| | Nobiletin | Bitter | Orange fruit |
| | | | Orange juice |
| | | | Juice from concentrate |
| | Sinensetin | Bitter | Orange fruit |
| | | | Orange juice (fresh) |
| | | | Juice from concentrate (frozen) |
| | | | Juice from concentrate |
| | | | Pure juice |
| Flavonols | Quercetin | Bitter | Grapefruit juice |
| | | | Lemon juice |
| | | | Endive |
| | | | Fresh hops |
| | | | Wine |
| | | | Black tea infusion |
| | | | Oolong tea infusion |
| | | | Green tea infusion |
| Flavans | Catechin | Bitter | Red wine |
| | | | Green tea infusion |
| | | | Oolong tea infusion |
| | | | Black tea infusion |
| | Epicatechin | Bitter | Red wine |
| | | | Low-fat cocoa powder |
| | | | Instant cocoa powder |
| | | | Green tea infusion |
| | | | Oolong tea infusion |
| | | | Black tea infusion |
| | Epicatechin gallate | Bitter and astringent | Green tea infusion |
| | | | Oolong tea infusion |
| | | | Black tea infusion |
| | Epigallocatechin | Bitter with sweet aftertaste | Green tea infusion |
| | | | Oolong tea infusion |
| | | | Black tea infusion |
| | Epigallocatechin gallate | Bitter with sweet aftertaste | Green tea infusion |
| | | | Oolong tea infusion |
| | | | Black tea infusion |
| Phenolic flavonoids | Catechin mono- and polymers MW <500 | Bitter | Red wine |
| | | | Rosé wine |
| | Catechin polymers MW >500 (tannins) | Astringent | Red wine |
| | | | Apple cider |
| | Polyphenols | Astringent and bitter | Low-fat cocoa power |
| | | | Instant cocoa powder |
| Isoflavones | Genistein and daidzein | Bitter or astringent | Soybeans |
| | | | Toasted, defatted soy flakes |
| | | | Textured soy protein |
| | | | Breakfast patties |
| | | | Tofu |
| | Genistin | Astringent | Soy seeds |
| | Daidzin | | |
| Triterpenes | | | |
| Limonoid aglycones | Limonin | Bitter | Lemon juice |
| | | | Orange juice |
| | | | Grapefruit juice |
| | | | Tangerine juice |
| | | | Grapefruit, flavedo |
| | | | Grapefruit, albedo |
| | | | Grapefruit, pith |
| | | | Grapefruit, seeds |
| | Nomilin | Bitter | Grapefruit juice |
| | | | Oroblanco juice |
| | | | Melogold juice |
| | Limonin glucoside | Tasteless | Grapefruit juice |
| | | | Lemon juice |
| Organosulfur compounds | | | |
| Glucosinolates | Sinigrin | Bitter | Cabbage |
| | | | Brussels sprouts |
| | | | Cauliflower |
| | | | Turnip or swede |
| | | | Calabrese |
| | | | Broccoli |

-continued

| Phytonutrient class | Typical component | Taste quality | Food source |
|---|---|---|---|
| | Progoitrin | Bitter | Collards<br>Kale<br>Mustard greens<br>Brussels sprouts<br>Cabbage<br>Cauliflower<br>Turnip or swede<br>Calabrese |
| Hydrolysis product of glucosinolates | Glucobrassicin | Bitter | Brussels sprouts |
| | Goitrin 5-vinyl-2-oxazolidine thione | Bitter | Aqueous extract of Brussels sprouts<br>Cabbage, pith<br>Cabbage, cambial cortex<br>Cabbage, leaf |
| Isothiocyanates | Allyl-isothiocyanate | Acrid mustard oils; pungent or lachrymatory | Cabbage, pith<br>Cabbage, cambial cortex<br>Cabbage, leaf |
| | 3-Methyl-sulfinylpropyl isothiocyanate | Acrid mustard oils | Cabbage, pith<br>Cabbage, cambial cortex<br>Cabbage, leaf |
| | Benzyl isothiocyanate | Acrid mustard oils; garlic-like | Cabbage, cambial cortex<br>Cabbage, leaf |
| | 4-Methylsulfinyl butyl isothiocyanate | Acrid mustard oils | Cabbage, pith<br>Cabbage, cambial cortex<br>Cabbage, leaf |
| | Phenylethyl isothiocyanate | Acrid, irritant, or lachrymatory | Cabbage, pith<br>Cabbage, cambial cortex<br>Cabbage, leaf |

Non-limiting sweet receptor ligands include metabolized sugars (glucose, fructose, etc.) and nonmetabolized sweeteners (sucralose, aspartame, rebaudiosides, steviosides (natural sweeteners extracted from the stevia plant), neotame, acesulfame-K, saccharin and the like). Sweet receptor ligands can also affect other chemosensory receptors. For example, aspartame is contemplated to play a role in responses relating to both sweet receptor activation and amino acid metabolism. Further sweet receptor ligands are described, e.g., by Kim, et al., 2002, "Highly sweet compounds of plant origin," Arch Pharm Res. 25(6):725-46 and Kinghorn, et al., 1989, "Intensely sweet compounds of natural origin," Medicinal Research Reviews 9(1):91-115. Many more sweet receptor ligands other than those listed herein and in the cited manuscripts, are known to those of skill in the art, and still more can be identified using methods known in the art and described herein. Exemplary sweet receptor ligands of plant origin are listed in the following table adapted from Kim et al., 2002.

| Compound type/name | Plant name | Sweetness/potency[a] |
|---|---|---|
| MONOTERPENE | | |
| Perillartine (10)[b] | *Perilla frutescens* (L.) Britton (Labiatae) | 370 |
| SESQUITERPENES | | |
| Bisabolanes | | |
| (+)-Hernandulcin (11) | *Lippia dulcis* Trev. (Verbenaceae) | 1,500 |
| 4β-Hydroxyhernandulcin (12) | *L. dulcis* | N.S.[c] |
| Acyclic glycoside | | |
| Mukurozioside IIb (13) | *Sapindus rarak* DC. (Sapindaceae) | ca. 1 |
| DITERPENES | | |
| Diterpene acid | | |
| 4β,11α-Dimethyl-1,2,3,4,5,10-hexahydro-fluorene-4α,6α-dicarboxylic acid (14)[b] | Pine tree | 1,300-1,800[d] |
| ent-Kaurene glycosides | | |
| Dulcoside A (15) | *Stevia rebaudiana* (Bertoni) Bertoni (Compositae) | 30 |
| Rebaudioside A (4) | *S. rebaudiana* | 242 |
| Rebaudioside B (16) | *S. rebaudiana* | 150 |
| Rebaudioside C (17) | *S. rebaudiana* | 30 |
| Rebaudioside D (18) | *S. rebaudiana* | 221 |
| Rebaudioside E (19) | *S. rebaudiana* | 174 |
| Rebaudioside F (20) | *S. rebaudiana* | N.S.[c] |
| Rubusoside (21) | *Rubus suavissimus* S. Lee (Rosaceae) | 115 |
| Steviolbioside (22) | *S. rebaudiana* | 90 |
| Steviol 13-0-β-D-glucoside (23) | *R. suavissimus* | N.S.[c] |
| Stevioside (5) | *S. rebaudiana* | 210 |

-continued

| Compound type/name | Plant name | Sweetness/potency[a] |
|---|---|---|
| Suavioside A (24) | *R. suavissimus* | N.S.[c] |
| Suavioside B (25) | *R. suavissimus* | N.S.[c] |
| Suavioside G (26) | *R. suavissimus* | N.S.[c] |
| Suavioside H (27) | *R. suavissimus* | N.S.[c] |
| Suavioside I (28) | *R. suavissimus* | N.S.[c] |
| Suavioside J (29) | *R. suavissimus* | N.S.[c] |
| Labdane glycosides | | |
| Baiyunoside (30) | *Phlomis betonicoides* Diels (Labiatae) | 500 |
| Phlomisoside I (31) | *P. betonicoides* | N.S.[c] |
| Gaudichaudioside A (32) | *Baccharis gaudichaudiana* DC. (Compositae) | 55 |
| TRITERPENES | | |
| Cucurbitane glycosides | | |
| Bryodulcoside | *Bryonia dioica* Jacq. (Cucurbitaceae) | N.S.[c] |
| Bryoside (33) | *B. dioica* | N.S.[c] |
| Bryonoside (34) | *B. dioica* | N.S.[c] |
| Carnosifloside V (35) | *Hemsleya carnosiflora* C. Y. Wu et Z. L. Chen (Cucurbitaceae) | 51 |
| Carnosifloside VI (36) | *H. carnosiflora* | 77 |
| Mogroside IV (37) | *Siraitia grosvenorii* (Swingle) Lu & Zhang[e] (Cucurbitaceae) | 233–392[d] |
| Mogroside V (2) | *S. grosvenorii* | 250–425[d] |
| 11-OxomogrosideV(38) | *Siraitia siamensis* Craib (Cucurbitaceae) | N.S.[c] |
| Scandenoside R6 (39) | *Hemsleya panacis-scandens* C. Y. Wu et Z. L. Chen (Cucurbitaceae) | 54 |
| Scandenoside R11 (40) | *H. panacis-scandens* | N.S.[c] |
| Siamenoside I (41) | *Siraitia grosvenorii, S. siamensis* | 563 |
| Cycloartane glycosides | | |
| Abrusoside A (42) | *Abrus precatorius* L.; *A. fruticulosus* Wall et W.& A. (Leguminosae) | 30 |
| Abrusoside B (43) | *A. precatorius, A. fruticulosus* | 100 |
| Abrusoside C (44) | *A. precatorius; A. fruticulosus* | 50 |
| Abrusoside D (45) | *A. precatorius; A. fruticulosus* | 75 |
| Abrusoside E (46) | *A. precatorius* | N.S.[c] |
| Dammarane glycosides | | |
| Cyclocarioside A (47) | *Cyclocarya paliurus* (Batal.) Iljinsk (Juglandaceae) | 200 |
| Cyclocaryoside I (48) | *C. paliurus* | 250 |
| Gypenoside XX (49) | *Gynostemma pentaphyllum* Makino (Cucurbitaceae) | N.S.[c] |
| Oleanane glycosides | | |
| Albiziasaponin A (50) | *Albizia myriophylla* Benth. (Leguminosae) | 5 |
| Albiziasaponin B (51) | *A. myriophylla* | 600 |
| Albiziasaponin C (52) | *A. myriophylla* | N.S.[c] |
| Albiziasaponin D (53) | *A. myriophylla* | N.S.[c] |
| Albiziasaponin E (54) | *A. myriophylla* | N.S.[c] |
| Apioglycyrrhizin (55) | *Glycyrrhiza inflata* Batal. (Leguminosae) | 300 |
| Araboglycyrrhizin (56) | *G. inflata* | 150 |
| Glycyrrhizin (1) | *Glycyrrhiza glabra* L. (Leguminosae) | 93–170[d] |
| Periandrin I (57) | *Periandra dulcis* Mart.; *P. mediterranea* (Vell.) Taub. (Leguminosae) | 90 |
| Periandrin II (58) | *P. dulcis, P. mediterranea* | 95 |
| Periandrin III (59) | *P. dulcis, P. mediterranea* | 92 |
| Periandrin IV (60) | *P. dulcis, P. mediterranea* | 85 |
| Periandrin V (61) | *P. dulcis* | 220 |
| Secodammarane glycosides | | |
| Pterocaryoside A (62) | *Pterocarya paliurus* Batal. (Juglandaceae) | 50 |
| Pterocaryoside B (63) | *P. paliurus* | 100 |
| STEROIDAL SAPONINS | | |
| Osladin (64) | *Polypodium vulgare* L. (Polypodiaceae) | 500 |
| Polypodoside A (65) | *Polypodium glycyrrhiza* DC. Eaton (Polypodiaceae) | 600 |
| Polypodoside B (66) | *P. glycyrrhiza* | N.S.[c] |
| Telosmoside A$_8$ (67) | *Telosma procumbens* (Hence) Merr. (Asclepiadaceae) | N.S.[c] |
| Telosmoside A$_9$ (68) | *T. procumbens* | N.S.[c] |
| Telosmoside A$_{10}$ (69) | *T. procumbens* | N.S.[c] |
| Telosmoside A$_{11}$ (70) | *T. procumbens* | N.S.[c] |

-continued

| Compound type/name | Plant name | Sweetness/potency[a] |
|---|---|---|
| Telosmoside A$_{12}$ (71) | T. procumbens | N.S.[c] |
| Telosmoside A$_{13}$ (72) | T. procumbens | N.S.[c] |
| Telosmoside A$_{14}$ (73) | T. procumbens | N.S.[c] |
| Telosmoside A$_{15}$ (74) | T. procumbens | 1000 |
| Telosmoside A$_{16}$ (75) | T. procumbens | N.S.[c] |
| Telosmoside A$_{17}$ (76) | T. procumbens | N.S.[c] |
| Telosmoside A$_{18}$ (77) | T. procumbens | N.S.[c] |
| PHENYLPROPANOIDS | | |
| trans-Anethole(78)[f] | Foeniculum vulgare Mill. (Umbelliferae) | 13 |
| | Illicium verum Hook F. (Illiciaceae) | |
| | Myrrhis odorata Scop. (Umbelliferae) | |
| | Osmorhizalongistylis DC. (Umbelliferae) | |
| | Piper marginatum Jacq. (Piperaceae) | |
| | Tagetes filicifolia Lag. (Compositae) | |
| Trans-Cinnamaldehyde (79) | Cinnamomum osmophloeum Kanehira (Lauraceae) | 50 |
| DIHYDROISOCOUMARIN | | |
| Phyllodulcin[g] (3) | Hydrangea macrophylla Seringe var. thunbergii (Siebold) Makino (Saxifragaceae) | 400 |
| FLAVONOIDS | | |
| Dihydrochalcone glycosides | | |
| Glycyphyllin (80) | Smilax glycyphylla Sm. (Liliaceae) | N.S.[c] |
| Naringin dihydrochalcone[e] (81) | Citris paradisi Macfad. (Rutaceae) | 300 |
| Neohesperidin dihydrochalcone[e] (82) | Citrus aurantium L. | 1,000 |
| Phlorizin (83) | Symplocos lancifolia Sieb. Et Zucc. (Symplocaceae) | N.S.[c] |
| Trilobatin (84) | Symplocos microcalyx Hayata | N.S.[c] |
| Dihydroflavonols and Dihydroflavonols glycosides | | |
| 3-Acetoxy-5,7-dihydroxy-4'-methoxyflavanone (85) | Aframomum hanburyi K. Schum. (Zingiberaceae) | N.S.[c] |
| 2R,3R-(+)-3-Acetoxy-5-7-4'-trihydroxyflavanone (86) | A. hanburyi | N.S.[c] |
| Dihydroquercetin 3-O-acetate 4'-methyl ether[e] (87) | Tessaria dodoneifolia (Hook. & Arn.) Cabrera (Compositae) | 400 |
| (2R,3R)-Dihydroquercetin 3-O-acetate (88) | T. dodoneifolia; Hymenoxys turneri K. Parker (Compositae) | 80 |
| (2R,3R)-2,3-Dihydro-5,7,3',4'-tetrahydroxy-6-methoxy-3-O-acetylflavonol (89) | H. turneri | 25 |
| (2R,3R)-2,3-Dihydro-5,7,3',4'-tetrahydroxy-6-methoxyflavonol (90) | H. turneri | 15 |
| (2R,3R)-2,3-Dihydro-5,7,4'-trihydroxy-6-methoxy-3-O-acetylflavonol (91) | H. turneri | 20 |
| Huangqioside E. (92) | Engelhardtia chrysolepis Hance (Juglandaceae) | N.S.[c] |
| Neoastilbin (93) | E. chrysolepis | N.S.[c] |
| PROANTHOCYANIDINS | | |
| Cinnamtannin B-1 (94) | Cinnamomum sieboldii Meisner (Lauraceae) | N.S.[c] |
| Cinnamtannin D-1 (95) | C. sieboldii | N.S.[c] |
| Selligueain A (96) | Selliguea feei Bory (Polypodiaceae) | 35 |
| Unnamed (97) | Arachniodes sporadosora Nakaike; A. exilis Ching (Aspidiaceae) | N.S.[c] |
| Unnamed (98) | A. sporadosora; A. exilis | N.S.[c] |
| BENZO[b]INDENO[1,2-d]PYRAN | | |
| Hematoxylin (99) | Haematoxylon campechianum L. (Leguminosae) | 120 |
| AMINO ACID | | |
| Monatin (100) | Schlerochiton ilicifolius A. Meeuse (Acanthaceae) | 1,200-1,400[d] |
| PROTEINS | | |
| Brazzein | Pentadiplandra brazzeana Baillon (Pentadiplandraceae) | 2,000 |
| Curculin | Curculigo latifolia Dryand. (Hypoxidaceae) | 550 |
| Mabinlin | Capparis masaikai Levl. (Capparidaceae) | N.S.[c] |
| Monellin | Dioscoreophyllum cumminsii (Stapf) Diels. (Menispermaceae) | 3,000 |

-continued

| Compound type/name | Plant name | Sweetness/potency[a] |
|---|---|---|
| Pentadin | *Pentadiplandra brazzeana* Bailon (Pentadiplandraceae) | 500 |
| Thaumatin | *Thaumatococcus danielli* (Bennett) Benth. (Marantaceae) | 1,600 |

[a]Values of relative sweetness on a weight comparison basis to sucrose (= 1.0).
[b]Semisynthetic derivative of natural product.
[c]N.S. = Sweetness potency not given.
[d]Relative sweetness varied with the concentration of sucrose.
[e]Formerly named *Momordica grosvenorii* Swingle and *Thladiantha grosvenorii* (Swingle) C. Jeffrey (Kinghorn and Kennelly, 1995).
[f]Identified as a sweet-tasting constituent of these six species. However, this compound has a wider distribution in the plant kingdom.
[g]The plant of origin may be crushed or fermented in order to generate phyllodulcin Many more chemosensory receptor ligands in addition to those listed herein and the cited manuscripts are known to those of skill in the art, and still more can be identified using methods known in the art and described herein.

In some embodiments, a nonmetabolized chemosensory receptor ligand, e.g. a tastant, is administered alone. In certain instances, the administration of one or more nonmetabolized chemosensory ligands can result in modulation of a hormone described herein. For example, sucralose is administered by itself or in conjunction with saccharin.

In other embodiments, a nonmetabolized chemosensory receptor ligand(s) is co-administered with a metabolized chemosensory receptor ligand(s), e.g. a metabolite. For example, a combination of sweet receptor tastant and a cognate metabolite could be sucralose and glucose. Other metabolized sweet receptor ligands include, but are not limited to, fructose and galactose.

Combining a nonmetabolized chemosensory receptor ligand (e.g., a tastant) with a metabolized chemosensory receptor ligand (e.g., a metabolite) may in cases enhance the resulting modulation of a hormone. In related embodiments, combining a nonmetabolized ligand for one receptor with a metabolized ligand for a different receptor enhances the resulting modulation of hormone expression. In some embodiments, stimulating L cells with different combinations of nonmetabolized ligands and metabolized ligands results in different hormonal expression profiles. Certain profiles are more desirable depending on the condition to be treated or even the particular individual to be treated.

The desired effects on treatment of a condition or modulation of hormone levels can be tailored by the number of chemosensory receptor ligands administered to a subject. In some embodiments, two chemosensory receptor ligands are administered to a subject. In other embodiments, three chemosensory receptor ligands are administered to a subject. In yet other embodiments, four chemosensory receptor ligands are administered to a subject. In yet other embodiments, five chemosensory receptor ligands are administered to a subject. In further embodiments, six or more chemosensory receptor ligands are administered to a subject. When multiple ligands are administered to a subject, the ligands can be in the same or different compositions. Multiple chemosensory receptor ligands can each target different receptor types or many or all the ligands can target one receptor type. For example, in a five chemosensory receptor ligand composition, three ligands may target the sweet receptor, one ligand for the bitter receptor, and one ligand for the umami receptor. Any combination is contemplated in the embodiments herein.

In most endocrine cell systems (e.g., the beta cell of the islet of Langerhans), for an appropriate secretory level of a hormone to occur the cell needs to sense the stimulus (in case of the beta cell, glucose), and in the case of nutrient-driven hormonal release, metabolism of the sensed nutrient is required for full secretory activation. It is recognized that both sensing and metabolism can elicit secretory release of hormone. For example, in the case of calcium, which is not a nutrient, sensing is sufficient for parathyroid hormone release. Thus, for full enteroendocrine activation it may be important that a nutrient is both sensed by the appropriate taste receptor and metabolized.

In certain embodiments, sweet receptor agonism will be achieved by coadministration of a composition comprising a sweet receptor agonist (e.g. sucralose, aspartame or stevioside, etc.) and an amount of D-glucose, e.g., between 0.1 to 10 mg/kg/min. Depending on the hormone of interest, co-administration may produce a more pronounced effect on hormonal release than either the tastant or glucose alone.

In further embodiments, a chemosensory receptor modifier is administered with a chemosensory receptor ligand to alter or change the activity of a receptor toward the ligand. In yet further embodiments a chemosensory receptor enhancer is administered with a chemosensory receptor ligand to enhance, potentiate or multiply the effect of the ligand. For example, a sweet receptor enhancer can be administered with a sweet receptor ligand, e.g., saccharin, to increase the sweetness potency and/or enhance hormone modulation. In certain instances, modifiers and/or enhancers are administered prior to administration of a chemosensory receptor ligand enhance, potentiate or multiply the effect of the ligand. In other instances, modifiers and/or enhancers are administered with a chemosensory receptor ligand together to enhance, potentiate or multiply the effect of the ligand. In yet further embodiments, a chemosensory receptor enhancer is administered along with food or prior to food. The food serves as a source of chemosensory receptor ligands that can have their effects enhanced, potentiated or multiplied. For example, a sweet receptor enhancer can be administered prior to ingestion of a sweet food such as a candy bar. Modulation and enhancement of chemosensory receptors by modulators and enhancers may produce a more pronounced effect on hormonal release than by a chemosensory receptor or food alone.

Identification of Chemosensory Receptor Ligands

A number of assays known in the art and described in the literature can be used to assay for taste transduction. For example, U.S. Pat. No. 7,105,650, describes in vitro binding assays, fluorescence polarization assays, solid state and soluble high throughput assays, computer based assays, cell-based binding assays, and assays using transgenic animals that express taste receptors.

Human gastrointestinal cells or cell membranes can be used to test for compounds that interact with taste signaling proteins and/or gastrointestinal protein hormones, neurotransmitters, or soluble mediators involved in metabolism, digestion or appetite either directly or indirectly, e.g., tastants, activators, inhibitors, enhancers, stimulators, agonists, antagonists, modulators and mimics. Assays for taste modulation can be used wherein the taste signaling protein(s) and/or gastrointestinal protein hormone(s), neurotransmitter(s), or soluble mediator(s) involved in metabolism, digestion or appetite acts as a direct or indirect reporter molecule(s) for the effect of a compound on signal transduction. Human gastrointestinal cells or their membranes can be used for such assays, e.g., to measure or detect changes in levels of the one or more taste signaling proteins and/or the one or more gastrointestinal protein hormones, neurotransmitters or soluble mediators synthesized or secreted by the cell, or to detect or measure changes in membrane potential, current flow, ion flux, transcription, phosphorylation, dephosphorylation, signal transduction, receptor-ligand interactions, second messenger concentrations, etc.

A modulator of taste transduction can be identified by contacting a human gastrointestinal cell or its membrane with a test compound, wherein the cell or membrane comprises one or more taste signaling proteins, evaluating the compound's effect on taste transduction. The human gastrointestinal cells or their membranes can be used in an indirect reporter assay to detect whether a test compound affects taste transduction and/or signal transduction of one or more gastrointestinal protein hormones, neurotransmitters or soluble mediators involved in metabolism (see, e.g., Mistili & Spector, 1997, Nature Biotechnology, 15, 961-64).

Gastrointestinal cells or their membranes can be used to assay the binding of a test compound that affects signal transduction by studying, e.g., changes in spectroscopic characteristics (e.g., fluorescence, absorbance, refractive index) or hydrodynamic (e.g., shape), chromatographic or solubility properties. Human gastrointestinal cells or their membranes can be used to examine the effect of a compound on interactions between a receptor and a G protein. For example, binding of a G protein to a receptor or release of the G protein from the receptor can be examined. In the absence of GTP, an activator will lead to the formation of a tight complex of all three subunits of the G protein with the receptor. This complex can be detected in a variety of ways, as noted above. Such an assay can be modified to search for inhibitors of taste transduction or inhibitors of signal transduction of one or more gastrointestinal protein hormones, neurotransmitters or soluble mediators. For example, an activator could be added to the receptor and G protein in the absence of GTP such that a tight complex forms, which could then be screened for inhibitors by studying dissociation of the receptor-G protein complex. In the presence of GTP, release of the alpha subunit of the G protein from the other two G protein subunits serves as a criterion of activation.

An activated or inhibited G protein will in turn influence downstream steps of the signal transduction pathway, affecting, e.g., the properties of target enzymes, channels and other effectors. Examples of downstream steps include activation of cGMP phosphodiesterase by transducin in the visual system, adenylyl cyclase by the stimulatory G protein, phospholipase C by $G_q$ and other cognate G proteins, and modulation of diverse channels by $G_i$ and other G proteins. In some embodiments, the human gastrointestinal cells or their membranes can be used to examine the effect of a compound on intermediate steps of signal transduction, such as the generation of diacyl glycerol and $IP_3$ by phospholipase C and, in turn, calcium mobilization by $IP_3$. In some embodiments, the compound may act directly on, e.g., the G protein, affecting downstream events indirectly. In some embodiments, the compound may directly affect the downstream effector. For a general review and methods of assaying taste signal transduction and gastrointestinal protein hormone signal transduction, see, e.g., Methods in Enzymology, vols. 237 and 238 (1994) and volume 96 (1983); Bourne et al., Nature, 10, 117-27 (1991); Bourne et al., Nature, 348, 125-32 (1990); Pitcher et al., Annu Rev. Biochem., 67, 653-92 (1998); Brubaker et al., Receptors Channels, 8, 179-88 (2002); Kojima et al., Curr. Opin. Pharmacol., 2, 665-68 (2002); Bold et al., Arch Surg., 128, 1268-73 (1993).

The effects of compounds on taste signaling polypeptides and/or gastrointestinal protein hormones, neurotransmitters or soluble mediators can be examined by performing assays described herein and known in the art. Any suitable physiological change that affects these signaling pathways can be used to assess the influence of a compound on the cells of this invention.

The effects of compounds on signal transduction in any of the above assays may be detected or measured in a variety of ways. For example, one can detect or measure effects such as transmitter release, hormone release, transcriptional changes to both known and uncharacterized genetic markers (e.g., northern blots), changes in cell metabolism such as cell growth or pH changes, ion flux, phosphorylation, dephosphorylation, and changes in intracellular second messengers such as $Ca^{2+}$, $IP_3$, DAG, PDE, cGMP or cAMP. Changes in second messenger levels can be optionally measured using, e.g., fluorescent $Ca^{2+}$ indicator dyes and fluorometric imaging.

In some embodiments the effects of a compound on G-protein-coupled receptors can be measured by using cells that are loaded with ion- or voltage-sensitive dyes, which report receptor activity. Assays that examine the activity of such proteins can also use known agonists and antagonists for other G-protein-coupled receptors as negative or positive controls to assess the activity of a test compound. To identify modulatory compounds, changes in the level of ions in the cytoplasm or membrane voltage can be monitored using an ion-sensitive or membrane-voltage fluorescent indicator, respectively. Among the ion-sensitive indicators and voltage probes that may be employed are those sold by Molecular Probes or Invitrogen. For G-protein-coupled receptors, lax G-proteins such as Gal5 and Gal6 can be used in the assay of choice (Wilkie et al., 1991, PNAS 88, 10049-53). Such lax G-proteins allow coupling of a wide range of receptors.

The effects of a compound can be measured by calculating changes in cytoplasmic calcium ion levels. In some embodiments, levels of second messengers such as $IP_3$ can be measured to assess G-protein-coupled receptor function (Berridge & Irvine, 1984, Nature, 312, 315-21). Cells expressing such G-protein-coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

The effects of a compound can be measured by determining the activity of proteins which, when activated, result in a change in the level of intracellular cyclic nucleotides, e.g., cAMP or cGMP, by activating or inhibiting enzymes such as adenylyl cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., 1991, Proc. Natl. Acad. Sci. U.S.A., 88, 9868-72 and Dhallan et al., 1990, Nature, 347, 184-87). In cases where activation of the protein results in a decrease in cyclic nucleotide levels, it may be preferable to expose the cells to agents that increase intracellular cyclic nucleotide levels, e.g., forskolin, prior to adding a compound in the assay.

The effects of a compound can be measured by calculating changes in intracellular cAMP or cGMP levels using immunoassays or bioassays (Simon, 1995, J. Biol. Chem., 270, 15175-80; Felley-Bosco et al., 1994, Am. J. Resp. Cell and Mol. Biol., 11, 159-64; and U.S. Pat. No. 4,115,538), or by examining phosphatidyl inositol (PI) hydrolysis according to, e.g., U.S. Pat. No. 5,436,128.

Transcription levels can also be transcription calculated. The human cell or its membrane containing the protein of interest may be contacted with a compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots, or polypeptide products may be identified using immunoassays or bioassays. Alternatively, transcription-based assays using reporter gene(s) may be used as described in U.S. Pat. No. 5,436,128. The reporter gene(s) can be, e.g., chloramphenicol acetyltransferase, firefly luciferase, bacterial luciferase, betagalactosidase and alkaline phosphatase. Furthermore, the protein of interest can act as an indirect reporter via attachment to a second reporter such as green fluorescent protein (see, e.g., Mistili & Spector, 1997, Nature Biotechnology, 15, 961-64).

The amount of transcription is then compared to the amount of transcription in the same cell in the absence of a compound. Alternatively, the amount of transcription may be compared with the amount of transcription in a substantially identical cell that lacks the protein of interest. For example, a substantially identical cell may be derived from the same cells from which the recombinant cell was prepared but which had not been modified by introduction of heterologous DNA. Any difference in the amount of transcription indicates that a compound has in some manner altered the activity of the protein of interest. In some embodiments, a compound is administered in combination with a known agonist or antagonist of transcription, to determine whether a compound can alter the activity of the agonist or antagonist.

The compounds tested can be any small chemical compound, or a biological material or entity, such as a protein, amino acid, sugar, nucleic acid or lipid. Alternatively, the compounds tested can be variants of taste signaling proteins. Typically, compounds will be small chemical molecules and peptides. Essentially any chemical compound can be used as a potential chemosensory receptor ligand in the assays of the invention although most often compounds dissolved in aqueous or organic solutions are used. The assays can be used to screen large chemical libraries by automating the assay steps (e.g., in microtiter formats on microtiter plates in robotic assays).

Regional Hormone Concentrations

Gut hormones secreted by enteroendocrine cells are released from their basolateral aspect into the mesenteric venous circulation. Therefore, these hormones traverse the portal vein area which drains all mesenteric venous efflux. Gut hormones, typically peptides, are also neurotransmitters and as such can stimulate afferent nerve endings that emanate from the gut and the liver. It is well recognized that CCK causes afferent vagal activation and that its physiologic effects are due almost exclusively to this neural activation. Hormones such as GLP-1, oxyntomodulin, PYY and GIP, and their post DPP-IV degradation breakdown products can have physiologic effects at the level gut nerves and can activate portal receptor/signaling pathways to cause activation of hepatic afferents. The action of GLP-1 to cause glucose-dependent insulin secretion is thought to predominantly occur via neural activation as its degradation by DPP-IV upon release begins immediately causing its circulating half-life to be less than 2 minutes. Moreover, the portal:arterial gradient for GLP-1 is large (>2:1) thus making its endocrine function in the beta cell excessively inefficient. Given its portal to peripheral gradient and its action as a neurotransmitter to activate gut afferent nerves, and its role to cause portal activation of hepatic afferents it is plausible that GLP-1's physiologic and pharmacologic actions can be produced in the absence of large fluctuations (and even perhaps undetectable alterations) of circulating peripheral (arterial or post hepatic venous) concentrations of GLP-1. As such GLP-1 is akin to norepinephrine which is a neurotransmitter but spills over into the circulation; like GLP-1, norepinephrine can be infused peripherally to act as a hormone to reproduce many of its physiologic functions. Thus, in some embodiments, the compositions and methods provided herein produce salutary effects on blood glucose and weight loss by enhancing portal concentrations of gut hormones while minimally augmenting peripheral concentrations.

Combinations

The chemosensory receptor ligands can be administered alone or in combination with each other. In certain embodiments, nonmetabolized chemosensory receptor ligands or combinations thereof are administered with one or more metabolized chemosensory receptor ligands, e.g., metabolite(s). Dosages for each chemosensory receptor ligand (i.e. ligands which bind and/or modulate sweet, umami, bitter, fat, sour, and/or bile acid receptors) can be determined via methods disclosed herein and found in the examples. Maximal response doses and maximum tolerated doses can be determined via animal and human experimental protocols as described herein and found in the examples. Additional relative dosages, represented as a percent of maximal response or of maximum tolerated dose, are easily obtained via the protocols.

In an exemplary dose-response experiment, chemosensory receptor ligands corresponding to five of the chemosensory receptors (e.g., sucralose, MSG, quinine, fatty acid emulsion, and chenodeoxycholic acid) and glucose are individually administered in an animal model (e.g. diabetic or obese rat model) to determine the optimum doses for each chemosensory receptor ligand. Chemosensory receptor ligands are administered individually at increasing amounts (mg/kg/min), where each subject is administered a set mg/kg/min dose and the dose is maintained at this set level for a defined period. Blood samples are collected at frequent intervals (e.g., every 1, 2, or 5 minutes) throughout the period and assayed for hormone levels. Hormones assayed include CCK, GIP, GLP-1, Oxyntomodulin, Peptide YY, Insulin C-peptide, and GLP-2. 50% of maximal response dose and 50% of the maximum tolerated dose are determined for each chemosensory receptor ligand.

In some embodiments, at least one chemosensory receptor ligand is administered at a concentration that is 50% of the maximal response dose. In other embodiments, at least one chemosensory receptor ligand is administered at a concentration that is 50% of the maximum tolerated dose. Chemosensory receptor ligands can be administered as 5%, 10%, 20%, 25%, 30%, 35%, 40%, 45%, 50%, 55%, 60%, 65%, 70%, 75%, 80%, 85%, 90%, 95%, or 100%, of the maximum response or maximum tolerated dose, inclusive of all integers therein.

Alternatively, the chemosensory receptor ligands described herein can be administered by a set potency range or limit of the chemosensory receptor ligands to their respective receptors. For example, in the above-referenced table of exemplary sweet receptor ligands of plant origin, sweetness potency can be expressed as relative sweetness to an equivalent weight comparison basis to sucrose (=1.0). Thus, for example in some embodiments, a composition comprising a sweet receptor ligand can be administered at a dosage that is of at least about 100×, at least about 200×, at least about 300×, at least about 400×, at least about 500×, at least about 600×, at least about 700×, at least about 800×, at least about 900×, at least about 1000×, at least about 1500×, at least about 2000×, at least about 2500×, at least about 3000×, at least about 4000×, at least about 5000×, at least 7500×, or at least 10000× the equivalent to the sweetness potency of sucrose per day. In other embodiments, a composition comprising a sweet receptor ligand can be administered at a dosage that is of about 100× to 10000×, about 500× to 5000×, about 700× to about 4000× or about 1000× to about 3000× the equivalent to the sweetness potency of sucrose per day. Ligands for other chemosensory receptors such as bitterness, sour or salt ligands can be dosed in similar manner in accordance to a known bitterness, sour or salty potency reference. For example, the Labeled Magnitude Scale allows measurement of a perceived intensity or potency of a bitter or salty taste sensation. See, e.g., Green et al., 1996, Chemical Senses 2: 323-334. This measured intensity can then be compared with a reference standard such as NaCl salt or quinine Dose administration can be expressed in, for example, delivery of at least about 1000× sweetness potency of sucrose, of at least about 2× a bitterness potency of quinine, and the like. Also, multiple ligands for a certain receptor can be used to achieve a desired potency dose; e.g., two or more sweet ligands can be used to achieve about 1000× sweetness potency of sucrose.

Alternatively, chemosensory receptor ligands described herein can be administered by weight measurement. By way of example, sweet, umami, and bitter receptor ligands (e.g., sucralose, glucose, monosodium glutamate, quinine) can be administered in amounts ranging from about 0.01 to about 100 mg/kg, inclusive of all integers therein. Fat receptor ligands (e.g., Intralipid®) can be administered as an emulsion/solution having a range of concentrations from about 0.5—about 20% solution delivered at 0.5-10 ml/min. Similarly, bile acid receptor ligands (e.g., Chenodeoxycholic acid, or CDC) can be administered as a solution having a range of concentrations from about 1 to about 50 mMol at a delivery of 1-10 ml/min. Metabolites, including non-limiting examples such as glucose and glutamates, can be administered in amounts ranging from about 0.1 to about 10 mg/kg, inclusive of all integers therein.

Another dose administration by weight can be on the basis of a weight of a chemosensory receptor ligand to achieve a certain multiple of natural ligand such as sucrose (e.g., a dosage amount of at least as sweet as 100 grams of sucrose). For example, in some embodiments, a composition comprising a sweet receptor ligand can be administered at a dosage that is equivalent to a sweetness potency of at least 100 grams, at least 500 grams, at least 750 grams, at least 1000 grams, at least 1250 grams, at least 1500 grams, at least 1750 grams, at least 2000 grams, at least 2500 grams, at least 3000 grams, at least 4000 grams, at least 5000 grams, or at least 10000 grams of sucrose per day. In other embodiments, a composition comprising a sweet receptor ligand can be administered at a dosage that is equivalent to the sweetness potency of about 100 to 10000 grams, about 500 to 5000 grams, about 750 to about 4000 grams or about 1000 to about 3000 grams of sucrose per day. Ligands for other chemosensory receptors such as bitterness, sour or salt ligands can be dosed in similar manner in accordance to a known bitter, sour or salty potency reference. Dose administration can be expressed in, for example, delivery of a sweetness potency of at least about 1000 grams sucrose, a bitterness potency of at least about 2 grams of quinine, and the like. Also, multiple ligands for a certain receptor can be used to achieve a desired potency dose; e.g., two or more sweet ligands can be used to achieve a sweetness potency equivalent to about 1000 grams of sucrose.

The combinations of chemosensory receptor ligands can be administered in a single composition or in multiple compositions. Multiple compositions may be administered simultaneously or at different times. The compositions may be administered in different delivery forms (i.e., tablets, powders, capsules, gels, liquids, nutritional supplements, edible food preparations (e.g. medical foods, bars, gels, liquids, etc.) and in any combination of such forms.

In one non-limiting example, a tablet containing at least one chemosensory receptor ligand is administered simultaneously with another tablet containing at least one chemosensory receptor ligand to provide the desired dosage. In a further example, the two tablets are administered at different times. In another non-limiting example, a tablet containing the desired combination of chemosensory receptor ligand(s) is administered to provide the full dosage. Any combination of delivery forms, compositions, and delivery times are contemplated herein.

The constituents of the compositions provided by the invention can be varied both with respect to the individual constituents and relative proportions of the constituents. In embodiments, the relative proportion of the constituents is optimized to produce the desired synergistic activity from the drug combination. For example, in a composition comprising, or a method comprising administering, two constituents, e.g., two chemosensory receptor ligands, the constituents can be present in ratios of or about, e.g., 1:1, 1:2, 1:3, 1:4, 1:5, 1:6, 1:7, 1:8, 1:9, 1:10, 1:15, 1:20, 1:25, 1:30, 1:35, 1:40, 1:45, 1:50, 1:60, 1:70, 1:80, 1:90, 1:100, 1:200, 1:300, 1:400, 1:500, 1:1000, etc. In a composition comprising, or a method comprising administering, three constituents, for example, two nonmetabolized chemosensory receptor ligands, and a metabolized chemosensory receptor ligand, the constituents can be present in ratios of or about, e.g., 1:1:1, 2:1:1, 2:2:1, 3:1:1, 3:3:1, 3:2:2, 3:3:2, 3:2:1, 4:1:1, 4:4:1, 4:2:2, 4:4:2, 4:2:3, 4:3:3, 4:4:3, 4:2:1, 5:1:1, 5:5:1, 5:2:1, 5:3:1, 5:3:2, 5:3:4, 5:5:2, 5:5:3, 5:5:4, 10:1:1, 10:10:1, etc.

In some embodiments, the invention provides combination treatments chosen to mimic mixed meals. For example, one or more carbohydrates (sweet), and one or more proteins (umami) can be used in doublet and triplet combinations. The combinations can be evaluated using methods of the invention and described herein. For example, a combination produces a desired hormonal release, glucose lowering and appetite suppression for the condition to be treated. In embodiments, additional ligands (e.g., tastants) that are specific for other chemosensory receptors can be evaluated and included in the combinations as determined appropriate using the methods of the invention. If one considers 5 tastants T1-T5 (sweet, bitter, umami, fat and bile acids, respectively) there is 1 combination of all 5 tastants (T1T2T3T4T5); there are 5 possible combinations of quadruplet tastant combinations (T1T2T3T4, T1T2T3T5, T1T2T4T5, T1T3T4T5, T2T3T4T5); 10 potential triplet (T1T2T3, T1T2T4, T1T2T5, T1T3T4, T1T3T5, T1T4T5, T2T3T4, T2T3T5, T2T4T5, T3T4T5) and 10 potential doublet combinations (T1T2, T1T3, T1T4, T1T5, T2T3, T2T4, T2T5, T3T4, T3T5, T4T5).

In some embodiments, one or more nonmetabolized chemosensory receptor ligand is administered alone or in combination with other nonmetabolized chemosensory receptor ligands. In other embodiments, the one or more nonmetabolized chemosensory receptor ligand is provided in combination with one or more metabolized chemosensory receptor ligands. In some embodiments, a nonmetabolized chemosensory receptor ligand is administered prior to a metabolized chemosensory receptor ligand. In other embodiments, a nonmetabolized chemosensory receptor ligand is administered after a metabolized chemosensory receptor ligand. In yet other embodiments, a nonmetabolized chemosensory receptor ligand is administered at similar times to a metabolized chemosensory receptor ligand. In certain instances, one or more metabolized chemosensory receptor ligands are derived from food. In certain aspects, a desired combination enhances and amplifies hormone signalling and secretion resulting from food ingestion. A non-limiting example of a combination is a sucralose administration prior, after, or simultaneously with an administration of sugar. In some aspects, a nonmetabolized chemosensory receptor ligand is delivered to the lower intestine and a metabolized chemosensory receptor ligand is delivered to the upper intestine. The metabolized chemosensory receptor ligand may or may not also be in the lower intestine. In other aspects, a nonmetabolized chemosensory receptor ligand is delivered to the same gastrointestinal segment as a metabolized chemosensory receptor ligand.

When more than one chemosensory receptor ligand is used in combination with at least one other ligand or compound, it is understood that the combination treatment regimen encompasses treatment regimens in which administration of one compound is initiated prior to, during, or after treatment with a second or additional agent in the combination, and continues until any time during treatment with any other agent in the combination or after termination of treatment with any other agent. Treatment regimens also include those in which the agents being used in combination are administered simultaneously or at different times and/or at decreasing or increasing intervals during the treatment period. Combination treatment includes periodic treatments that start and stop at various times to assist with the clinical management of the patient.

Indications

The methods of the embodiments provided herein are indicated for treatment of conditions or disorders associated with a chemosensory receptor. Specifically, these conditions include those in which modulation of the metabolic hormones regulated by chemosensory receptor stimulation produces a desired effect. Among the conditions associated with a chemosensory receptor that are contemplated for treating using the compositions and methods of the embodiments herein are metabolic syndrome, diabetes type I, diabetes type II, obesity, binge eating, undesired food cravings, food addiction, a desire to reduce food intake or to lose weight or maintain weight loss, anorexia, glucose intolerance, gestational diabetes mellitus (GDM), impaired fasting glycemia (IFG), dyslipidemia, post-prandial dyslipidemia, hyperlipidemia, hypertriglyceridemia, post hypertriglyceridemia, insulin resistance, bone loss disorders, osteopenia, osteoporosis, muscle wasting disease, muscle degenerative disorders, polycystic ovary syndrome (PCOS), non-alcoholic fatty liver disease (NAFL), non-alcoholic steatohepatitis (NASH), depression, a mood disorder, immune disorders of the gut (e.g., celiac disease), bowel irregularity, irritable bowel syndrome (IBS), or inflammatory bowel disease (IBD), including, e.g., ulcerative colitis, Crohn's disease, and short bowel syndrome. For example, disorders such as frailty, anorexia, cachexia, loss of lean body mass, food associated or food-induced nausea and vomiting, food allergies, food associated aversive reactions may be treated with chemosensory receptor antagonists.

In some embodiments, the compositions and methods provided herein are indicated for treatment, prevention and or maintenance of a metabolic disorder, disease or defect. Metabolic disorders, diseases or defects can include disorders, diseases or defects in energy homeostasis and disorders, diseases or defects in fuel homeostasis.

In certain embodiments, the compositions and methods provided herein are indicated for treatment, prevention and or maintenance of disorders, diseases and defects associated with energy homeostasis. Energy homeostasis generally relates to the signally pathways, molecules and hormones associated with food intake and energy expenditure. Disorders, diseases and defects associated with energy homeostasis include but are not limited to diabetes type I, diabetes type II, prediabetes, impaired fasting glycemia (IFG), and gestational diabetes mellitus (GDM). In some instances the compositions and methods provided herein are indicated for treatment, prevention and or maintenance of diabetes type I or type II.

In certain embodiments, the compositions and methods provided herein are indicated for treatment, prevention and or maintenance of disorders, diseases and defects associated with fuel homeostasis. Disorders, diseases and defects associated with fuel homeostasis include but is not limited to non-alcoholic fatty liver disease (NAFL), non-alcoholic steatohepatitis (NASH), hyperlipidemia, post hypertriglyceridemia, hypertriglyceridemia, insulin resistance and polycystic ovary syndrome (PCOS).

The embodiments also provide compositions and methods useful for treating conditions in which an increase in insulin secretion or control of glucose levels resulting from modulation of enteroendocrine cell hormones (e.g., GLP-1 or GIP) would be beneficial. These conditions include, but are not limited to, metabolic syndrome, diabetes type 1, diabetes type II, gestational diabetes, glucose intolerance, and related conditions including those in which patients suffer from glucose intolerance.

The embodiments also provide compositions and methods for modulating growth (proliferation), and/or generation (neogenesis), and/or prevention of cell death (apoptosis) of insulin producing and secreting cells (Beta cells) through the release of neural and hormonal signals emanating from the gut in response to luminal chemosensory stimulation. Gut hormones such as GLP-1, PYY, GLP-2 and gastrin have all been implicated in the process of beta cell preservation or beta cell mass expansion. In one aspect, chemosensory stimulation provides a hormonal signal coupled to a neural signal. The hormonal signal can occur before, after or at similar timeframes as the neural signal.

The embodiments also provide compositions and methods for treating conditions in which appetite suppression resulting from modulation of, e.g., PYY, oxyntomodulin, and/or CCK, would be beneficial. These conditions include, but are not limited to, obesity, binge eating, undesired food cravings, a desire to reduce food intake or to lose weight or maintain weight loss, and related conditions.

Further provided are compositions and methods for treating conditions in which proliferation of gut cells resulting from modulation of, e.g., GLP-2, would be beneficial, such as, short bowel syndrome, Crohn's disease, inflammatory bowel disease, ulcerative colitis, and other conditions resulting in bowel damage, including osteoporosis.

Methods of Treatment

Disorders of Glucose Metabolism

The embodiments described herein provide compositions and methods for treating and preventing disorders of glucose metabolism and their associated conditions.

For example, provided herein are methods for treating mammalian subjects with diabetes, including primary essential diabetes such as Type I Diabetes or Type II Diabetes (NIDDM) and secondary nonessential diabetes, comprising administering to the subject at least one chemosensory receptor ligand as described herein. In accordance with the method of this invention a symptom of diabetes or the chance of developing a symptom of diabetes, such as atherosclerosis, obesity, hypertension, hyperlipidemia, fatty liver disease, nephropathy, neuropathy, retinopathy, foot ulceration and cataracts, each such symptom being associated with diabetes, can be reduced.

The methods and compositions provided by the invention are useful for preventing or ameliorating diseases and symptoms associated with hyperglycemia and insulin resistance or low insulin levels. While a cluster of signs and symptoms associated may coexist in an individual patient, it many cases only one symptom may dominate, due to individual differences in vulnerability of the many physiological systems affected by insulin resistance. Nonetheless, since hyperglycemia and insulin resistance are major contributors to many disease conditions, agents that address these cellular and molecular defects are useful for prevention or amelioration of virtually any symptom in any organ system that may be due to, or exacerbated by hyperglycemia and insulin resistance.

Metabolic syndrome is a cluster of metabolic abnormalities including abdominal obesity, insulin resistance, glucose intolerance, diabetes, hypertension and dyslipidemia. These abnormalities are known to be associated with an increased risk of vascular events.

In addition to the metabolic disorders related to insulin resistance indicated above, disease symptoms secondary to hyperglycemia also occur in patients with NIDDM. These include nephropathy, peripheral neuropathy, retinopathy, microvascular disease, ulceration of the extremities, and consequences of nonenzymatic glycosylation of proteins, e.g. damage to collagen and other connective tissues. Attenuation of hyperglycemia reduces the rate of onset and severity of these consequences of diabetes. Because compositions and methods of the invention help to reduce hyperglycemia in diabetes, they are useful for prevention and amelioration of complications of chronic hyperglycemia.

Elevated triglyceride and free fatty acid levels in blood affect a substantial fraction of the population and are an important risk factor for atherosclerosis and myocardial infarction. Provided herein are compositions and methods useful for reducing circulating triglycerides and free fatty acids in hyperlipidemic patients. Hyperlipidemic patients often also have elevated blood cholesterol levels, which also increase the risk of cardiovascular disease. Cholesterol-lowering drugs such as HMG-CoA reductase inhibitors ("statins") can be administered to hyperlipidemic patients in addition to chemosensory receptor ligand compositions of the invention, optionally incorporated into the same pharmaceutical composition.

A substantial fraction of the population is affected by fatty liver disease, also known as nonalcoholic steatohepatitis (NASH); NASH is often associated with obesity and diabetes. Hepatic steatosis, the presence of droplets of triglycerides with hepatocytes, predisposes the liver to chronic inflammation (detected in biopsy samples as infiltration of inflammatory leukocytes), which can lead to fibrosis and cirrhosis. Fatty liver disease is generally detected by observation of elevated serum levels of liver-specific enzymes such as the transaminases ALT and AST, which serve as indices of hepatocyte injury, as well as by presentation of symptoms which include fatigue and pain in the region of the liver, though definitive diagnosis often requires a biopsy. The anticipated benefit is a reduction in liver inflammation and fat content, resulting in attenuation, halting, or reversal of the progression of NASH toward fibrosis and cirrhosis.

Hypoinsulinemia is a condition wherein lower than normal amounts of insulin circulate throughout the body and wherein obesity is generally not involved. This condition includes Type I diabetes.

Type 2 Diabetes or abnormal glucose metabolism may be caused by a variety of factors and may manifest heterogeneous symptoms. Previously, Type 2 Diabetes was regarded as a relatively distinct disease entity, but current understanding has revealed that Type 2 Diabetes (and its associated hyperglycemia or dysglycemia) is often a manifestation of a much broader underlying disorder, which includes the metabolic syndrome as noted above. This syndrome is sometimes referred to as Syndrome X, and is a cluster of cardiovascular disease risk factors that, in addition to glucose intolerance, includes hyperinsulinaemia, dyslipidaemia, hypertension, visceral obesity, hypercoagulability, and microalbuminuria.

Also provided herein are compositions and methods for treating obesity, comprising administering to the subject at least one chemosensory receptor ligand as described herein in an amount effective to treat the condition. The agent can be administered orally, and alternatively, other routes of administration that can be used in accordance with this invention include rectally, and parenterally, by injection (e.g., by intraluminal intestinal injection).

Both human and non-human mammalian subjects can be treated in accordance with the methods of this invention. In embodiments, the present invention provides compositions and methods for preventing or treating diabetes in a wide range of subject mammals, in particular, a human patient that has, has had, is suspected of having, or who is pre-disposed to developing diabetes. Diabetes mellitus is selected from the group consisting of insulin-dependent diabetes mellitus (IDDM or type I diabetes) and non-insulin-dependent diabetes mellitus (NIDDM, or type II diabetes). Examples of disorders related to diabetes mellitus have been described and include, but are not limited to, impaired glucose tolerance (IGT); maturity-onset diabetes of youth (MODY); leprechaunism (insulin receptor mutation), tropical diabetes, diabetes secondary to a pancreatic disease or surgery; diabetes associated with a genetic syndrome (e.g., Prader-Willi syndrome); pancreatitis; diabetes secondary to endocrinopathies; adipositas; and metabolic syndrome (syndrome X).

Diabetic subjects appropriate for treating using the compositions and methods provided by the invention can be easily recognized by the physician, and are characterized by, e.g., fasting hyperglycemia, impaired glucose tolerance, glycosylated hemoglobin, and, in some instances, ketoacidosis associated with trauma or illness. Hyperglycemia or high blood sugar is a condition in which an excessive amount of glucose circulates in the blood plasma. This is generally a blood glucose level of 10+ mmol/L, but symptoms and effects may not start to become noticeable until later numbers such as 15-20+ mmol/L. NIDDM patients have an abnormally high blood glucose concentration when fasting and delayed cellular uptake of glucose following meals or after a diagnostic test known as the glucose tolerance test. NIDDM is diagnosed based on recognized criteria (American Diabetes Association, Physician's Guide to Insulin-Dependent (Type I) Diabetes, 1988; American Diabetes Association, Physician's Guide to Non-Insulin-Dependent (Type II) Diabetes, 1988). The optimal dose of a particular chemosensory receptor ligand composition for a particular subject can be determined in the clinical setting by a skilled clinician.

Chronic Kidney Disease, Diabetic Nephropathy, Macular Degeneration and Diabetes-Associated Conditions The compositions and methods provided herein can be used to prevent or treat kidney diseases. Diabetes is the most common cause of chronic kidney disease and kidney failure, accounting for nearly 44 percent of new cases. Even when diabetes is controlled, the disease can lead to chronic kidney disease and kidney failure. Most people with diabetes do not develop chronic kidney disease that is severe enough to progress to kidney failure. Nearly 24 million people in the United States have diabetes, and nearly 180,000 people are living with kidney failure as a result of diabetes. High blood pressure, or hypertension, is a major factor in the development of kidney problems in people with diabetes.

Accumulation of the glomerular mesangial extracellular matrix (ECM) leading to glomerulosclerosis is a common finding in diabetic nephropathy and other chronic kidney diseases. Several lines of evidence indicate that ECM accumulation in such chronic renal diseases results from both increased synthesis and decreased degradation of ECM components and it is widely accepted that ECM degradation in glomeruli and glomerular cells is mediated by a plasminogen activator-plasmin-matrix metalloproteinase-2 (MMP)-2 cascade. In addition, a variety of studies have reported decreased plasminogen activator (PA) activity, decreased plasmin activity, or increased levels of PA inhibitor 1 (PAI-1; the major PA inhibitor), in glomeruli obtained from animals with experimentally induced glomerular injuries known to result in mesangial matrix accumulation (Baricos, et al., "Extracellular Matrix Degradation by Cultured Mesangial Cells: Mediators and Modulators" (2003) Exp. Biol. Med. 228:1018-1022).

Macular degeneration (AMD) is the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD.

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy (DR) is an ocular disorder that develops in diabetes due to thickening of capillary basement membranes and lack of contact between pericytes and endothelial cells of the capillaries. Loss of pericytes increases leakage of the capillaries and leads to breakdown of the blood-retina barrier.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

Compositions of the embodiments described herein can be, as needed, administered in combination with one or more standard therapeutic treatments known in the art. For example, for treatment of diabetic nephropathy, compounds of the present invention can be administered in combination with, for example, ACE inhibitors, angiotensin II receptor blockers (ARBS) or any other conventional therapy such as, for example, glucose management.

Obesity and Eating Disorders

Further provided herein are compositions and methods that can be used to prevent or treat obesity. Central obesity, characterized by its high waist to hip ratio, is an important risk for metabolic syndrome. Metabolic syndrome, as described above, is a combination of medical disorders which often includes diabetes mellitus type 2, high blood pressure, high blood cholesterol, and triglyceride levels (Grundy S M (2004), J. Clin. Endocrinol. Metab. 89(6): 2595-600). Obesity and other eating disorders are described in, e.g., U.S. Pat. App. Pub. No. 2009/0062193, "Compositions and Methods for the Control, Prevention and Treatment of Obesity and Eating Disorders."

"Obesity" is generally defined as a state wherein the body mass index is over 30, but any subject, including those with a body mass index of less than 30, who needs or wishes to reduce body weight or prevent body weight gain can be considered to be obese or overweight. For example, subjects with a BMI of less than 30 and 25 and above or below 25 are also included among the subjects of the invention. Morbid obesity typically refers to a state wherein the BMI is 40 or greater. In embodiments, the subject may be suffering from or be susceptible to a condition associated with eating such as binge eating or food cravings.

A "subject' may include any mammal, including humans. A "subject" may also include other mammals kept as pets or livestock (e.g., dogs, cats, horses, cows, sheep, pigs, goats). Subjects who may benefit from the methods provided herein may be overweight or obese; however, they may also be lean. Subjects who may benefit from the methods provided herein may be desirous of losing weight or may have an eating disorder, such as binge eating, or an eating condition, such as food cravings. Subjects who may benefit from the methods provided herein may be desirous of modifying food preferences. They may have a metabolic disorder or condition in addition to these conditions. Exemplary metabolic disorders include diabetes, metabolic syndrome, insulin-resistance, and dyslipidemia. Subjects can be of any age. Accordingly, these disorders can be found in young adults and adults (e.g., those aged 65 or under) as well as infants, children, adolescents, and the elderly (e.g., those over the age of 65).

By "metabolic rate" is meant the amount of energy liberated/expended per unit of time. Metabolism per unit time can be estimated by food consumption, energy released as heat, or oxygen used in metabolic processes. It is generally desirable to have a higher metabolic rate when one wants to lose weight. For example, a person with a high metabolic rate may be able to expend more energy (and burn more calories) to perform an activity than a person with a low metabolic rate for that activity.

As used herein, "lean mass" or "lean body mass" refers to muscle and bone. Lean body mass does not necessarily indicate fat free mass. Lean body mass contains a small percentage of fat (roughly 3%) within the central nervous system (brain and spinal cord), marrow of bones, and internal organs. Lean body mass is measured in terms of density. Methods of measuring fat mass and lean mass include, but are not limited to, underwater weighing, air displacement plethysmograph, x-ray, dual-energy x-ray absorptiometry (DEXA) scans, MRIs and CT scans. In one embodiment, fat mass and lean mass is measured using underwater weighing.

By "fat distribution" is meant the location of fat deposits in the body. Such locations of fat deposition include subcutaneous, visceral and ectopic fat depots.

By "subcutaneous fat" is meant the deposit of lipids just below the skin's surface. The amount of subcutaneous fat in a subject can be measured using any method available for the measurement of subcutaneous fat. Methods of measuring subcutaneous fat are known in the art, for example, those described in U.S. Pat. No. 6,530,886.

By "visceral fat" is meant the deposit of fat as intra-abdominal adipose tissue. Visceral fat surrounds vital organs and can be metabolized by the liver to produce blood cholesterol. Visceral fat has been associated with increased risks of conditions such as polycystic ovary syndrome, metabolic syndrome and cardiovascular diseases.

By "ectopic fat storage" is meant lipid deposits within and around tissues and organs that constitute the lean body mass (e.g., skeletal muscle, heart, liver, pancreas, kidneys, blood vessels). Generally, ectopic fat storage is an accumulation of lipids outside classical adipose tissue depots in the body.

Fat mass can be expressed as a percentage of the total body mass. In some aspects, the fat mass is reduced by at least 1%, at least 5%, at least 10%, at least 15%, at least 20%, or at least 25% over the course of a treatment. In one aspect, the subject's lean mass is not decreased over the course of a treatment.

In another aspect, the subject's lean mass is maintained or increased over the course of a treatment. In another aspect, the subject is on a reduced calorie diet or restricted diet. By "reduced calorie diet" is meant that the subject is ingesting fewer calories per day than compared to the same subject's normal diet. In one instance, the subject is consuming at least 50 fewer calories per day. In other instances, the subject is consuming at least 100, 150 200, 250, 300, 400, 500, 600, 700, 800, 900, 1000 fewer calories per day. In some embodiments, the method involves the metabolism of visceral fat or ectopic fat or both at a rate of at least about 5%, 10%, 15%, 20%, 25%, 30%, 40%, or 50%, greater than for subcutaneous fat. In one aspect, the methods result in a favorable fat distribution. In one embodiment, favorable fat distribution is an increased ratio of subcutaneous fat to visceral fat, ectopic fat, or both. In one aspect, the method involves an increase in lean body mass, for example, as a result of an increase in muscle cell mass. In one embodiment, the amount of subcutaneous fat is reduced in a subject by at least about 5%. In other embodiments, the amount of subcutaneous fat is reduced by at least about 10%, 15%, 20%, 25%, 30% 40%, or 50% compared to the subject prior to administration of a chemosensory receptor ligand composition.

The methods described herein can be used to reduce the amount of visceral fat in a subject. In one instance, the visceral fat is reduced in a subject by at least about 5%. In other instances, the visceral fat is reduced in a subject by at least about 10%, 15%, 20%, 25%, 30% 40%, or 50% compared to the subject prior to administration of a chemosensory receptor ligand composition. Visceral fat can be measured through any means available to determine the amount of visceral fat in a subject. Such methods include, for example, abdominal tomography by means of CT scanning and MRI. Other methods for determining visceral fat are described, for example, in U.S. Pat. Nos. 6,864,415, 6,850,797, and 6,487,445.

In one embodiment, a method for preventing the accumulation of ectopic fat or reducing the amount of ectopic fat in a subject is provided, wherein the method comprises administering, to a subject in need thereof, a chemosensory receptor ligand composition effective to prevent accumulation of ectopic fat or to reduce the amount of ectopic fat in the subject. It is understood that a treatment can be a series of individual doses, or a treatment regimen, provided to the subject over a period of time. In one instance, the amount of ectopic fat is reduced in a subject by at least about 5% compared to the untreated subject. In other instances, the amount of ectopic fat is reduced by at least about 10%, 15%, 20%, 25%, 30% 40%, or 50%. Alternatively, the amount of ectopic fat is proportionally reduced 5%, 10%, 15%, 20%, 25%, 30%, 40%, 50%, 60%, 70%, 80%, 90%, or 100% in comparison to subcutaneous fat in a subject. Ectopic fat can be measured in a subject using any method available for measuring ectopic fat.

In another embodiment, methods for altering anthropometric parameters, e.g., waist circumference, hip circumference, and waist-to-hip ratio are provided. Waist circumference is a measure of abdominal obesity. In one embodiment, methods for reducing waist circumference of a subject are provided, wherein the method comprises administering, to a subject in need thereof, a chemosensory receptor ligand composition in an amount effective to reduce the waist circumference of the subject. In one embodiment, the waist circumference of the subject is reduced by at least about 1%. In other embodiments, the waist circumference of the subject is reduced by at least about 2%, 3%, 4%, 5%, 6%, 7%, 8%. 9% or 10% compared to the subject prior to administration of a chemosensory ligand receptor ligand composition provided herein. In one embodiment, the waist circumference of the subject is reduced by at least about 1 cm. In other embodiments, the waist circumference of the subject is reduced by at least about 2 cm, 3 cm, 4 cm, 5 cm, or 6 cm compared to the subject prior to administration of a chemosensory receptor ligand composition.

In another embodiment, methods for reducing hip circumference of a subject are provided, wherein the method comprises administering, to a subject in need thereof, a chemosensory receptor ligand composition provided herein in an amount effective to reduce the hip circumference of the subject. In one embodiment, the hip circumference of the subject is reduced by at least about 1%. In other embodiments, the waist circumference of the subject is reduced by at least about 2%, 3%, 4%, 5%, or 6% compared to the subject prior to administration of a chemosensory receptor ligand composition. In one embodiment, the waist circumference of the subject is reduced by at least about 1 cm. In other embodiments, the waist circumference of the subject is reduced by at least about 2 cm, 3 cm, 4 cm, 5 cm, or 6 cm compared to the subject prior to administration of a chemosensory receptor ligand composition.

Also provided are methods to reduce weight in a morbidly obese subject by first reducing the subject's weight to a level below that of being morbidly obese, then administering an effective amount of a chemosensory receptor ligand composition to further reduce the subject's weight. Methods for reducing a subject's weight to being below that of morbid obesity include reducing caloric intake, increasing physical activity, drug therapy, bariatric surgery, such as gastric bypass surgery, or any combinations of the preceding methods. In one aspect, administering the treatment results in reduced caloric intake, which further reduces the weight of the subject. In another embodiment, methods are provided for reducing the body mass index (BMI) in a subject having a BMI of 40 or less by administering a chemosensory receptor ligand composition in an amount and regimen effective to further reduce the subject's weight.

In embodiments, methods for reducing the risk of developing metabolic disorders are provided, where the method comprises administering to the subject a chemosensory receptor ligand composition in an amount effective to reduce the weight or control the blood glucose of a subject.

In another embodiment, methods for controlling or modifying eating behaviors are provided, wherein the methods comprise administering, to a subject in need thereof, a chemosensory receptor ligand composition effective to control or modify an eating behavior by the subject. In one embodiment, methods for controlling binge eating are provided, where the methods comprise administering, to a subject in need thereof, a chemosensory receptor ligand composition in an amount effect to control or curb binge eating by the subject. In one embodiment, a chemosensory receptor ligand composition is administered at times of the day when the subject is most likely to binge eat. In one aspect, binge eating is characterized by 1) eating, in a discrete period of time (e.g., within any 2-hour period), an amount of food that is definitely larger than most people would eat during a similar period of time and under similar circumstances and 2) a sense of lack of control over eating during the episode (e.g., a feeling that one cannot stop eating or control what or how much one is eating). The reduction of binge eating includes a reduction in the frequency of binge eating episodes, the duration of binge eating episodes, the total amount consumed during a binge eating episode, difficulty in resisting the onset of a binge eating episode, and any combination thereof, as compared to as compared to such frequency, duration, amount and resistance in the absence of the chemosensory receptor ligand composition. For example, in one embodiment, a method may comprise a reduction in the frequency of binge eating episodes. In another embodiment, a method may comprise a reduction in the duration of binge eating episodes. In yet another embodiment, a method may comprise a reduction in the total amount consumed during a binge-eating episode. In yet another embodiment, a method may comprise a reduction in difficulty resisting the onset of a binge-eating episode.

Some of the signs of binge eating include eating large amounts of food when not physically hungry, rapid eating, hiding of food because the person feels embarrassed about how much he or she is eating, eating until uncomfortably full, or any combination thereof. Many binge eaters are emotional eaters, i.e. their binge eating is triggered by their emotional state (e.g., some binge eaters eat when they are sad, some eat when they are happy, and some eat when they are under stress). A large number of binge eaters suffer from anxiety disorders, such as obsessive-compulsive disorder; impulse control problems; or personality disorders, such as borderline personality disorder or depression. In one embodiment, the binge eating is in response to stressed conditions. Other binge eaters are substance abusers, such as drug abusers or alcohol abusers. Not everyone who has a binge eating disorder is overweight, such as those binge eaters diagnosed with bulimia.

Subjects who binge eat often do so at particular times of the day, and thus treatment should be adjusted according to when the subject is most likely to binge eat. For example, if the subject binge eats mostly after 7 p.m. at night, the subject should be administered a chemosensory receptor ligand composition at or shortly before 7 p.m. In one embodiment, the subject is administered a chemosensory receptor ligand composition at the time they are susceptible to binge eating. In other embodiments, the subject is administered a chemosensory receptor ligand composition at least about 5 minutes, at least about 15 minutes, at least about 30 minutes, at least about 45 minutes, at least about 1 hour, at least about 1 hour and 30 minutes, or at least about 2 hours before they are susceptible to binge eating. An effective amount of a chemosensory receptor ligand composition in this embodiment is an amount effective to curb or control the subject's desire to binge eat. Therefore, the effective amount of a chemosensory receptor ligand composition will change dependent upon the subject and the level of their desire to binge eat. Furthermore, if a subject's desire to binge eat is less at one point in the day than at another, the dosage can be adjusted accordingly to provide a lower dose at the times of the day the subject has a lower desire to binge eat, and to provide a higher dose at the times of the day the subject has a higher desire to binge eat. In one embodiment, the subject is administered a peak dosage of a chemosensory receptor ligand composition at the time they have a high desire to binge eat. In other embodiments, the subject is administered a peak dosage of a chemosensory receptor ligand composition at least about 5 minutes, at least about 15 minutes, at least about 30 minutes, at least about 45 minutes, at least about 1 hour, at least about 1 hour and 30 minutes, or at least about 2 hours before they have a high desire to binge eat.

In another embodiment, methods for modifying food preferences in a subject are provided, wherein methods comprise administering, to a subject in need thereof, a chemosensory ligand receptor composition in an amount effective to modify food preferences in the subject. The chemosensory receptor targeted by a composition can influence the subject's desire to eat the corresponding food. For example, a composition comprising ligands for the sweet receptor can reduce the subject's desire for sweet foods. Therefore, in embodiments, the subject's food preferences that are influenced by the treatment can include preferences for sweet foods, savory foods, high fat foods, salty foods, sour foods, and any combination thereof.

The modifications in food preferences may include a decrease in a preference for such foods, a decrease in the amount of intake of such foods, an enhancement of a preference of one food type over another food type, changes in frequency of cravings for such foods, duration of cravings for such foods, intensity of cravings for such foods, difficulty in resisting cravings for such foods, frequency of eating in response to cravings for such foods, and any combination thereof, as compared to such frequency, duration, intensity, or resistance in the absence of treatment. In yet another embodiment, a method may comprise reducing a subject's preference for sweet foods, savory foods, high fat foods, salty foods, sour foods, and any combination thereof.

In one embodiment, a method may comprise reducing a subject's frequency of cravings for sweet foods, savory foods, high fat foods, salty foods, sour foods, and any combination thereof. In another embodiment, a method may comprise reducing a subject's duration of cravings for sweet foods savory foods, high fat foods, salty foods, sour foods, and any combination thereof, etc. In yet another embodiment, a method may comprise reducing a subject's intensity of cravings for sweet foods, savory foods, high fat foods, salty foods, sour foods, and any combination thereof. In yet another embodiment, a method may comprise reducing a subject's difficulty in resisting cravings for sweet foods, savory foods, high fat foods, salty foods, sour foods, and any combination thereof. In yet another embodiment, a method may comprise reducing a subject's frequency of eating in response to cravings for sweet foods, savory foods, high fat foods, salty foods, sour foods, and any combination thereof. In yet another embodiment, a method may comprise reducing a subject's intake of sweet foods, savory foods, high fat foods, salty foods, sour foods, and any combination thereof.

Treatment of Bowel Damage

The compositions and methods provided herein can be used for the treatment of short bowel syndrome and compromised intestinal function (e.g., small bowel resection, colitis, enteritis, inflammatory bowel syndrome, ischemic bowel, and chemotherapeutic injury to the intestine). Short bowel syndrome refers to the collection of symptoms caused by intestinal resection. Its symptoms include intractable diarrhea, dehydration, malabsorption of macronutrients, weight loss, malabsorption of vitamins and trace elements and malnutrition. GLP-2 is known to slow gastric emptying, increase intestinal transit time and inhibit sham feeding-induced gastric acid secretion. Patients with jejunostomy often have impaired meal-stimulated GLP-2 responses, and thus impaired absorption. Administration of GLP-2 in patients with jejunostomy has been shown to improve intestinal absorption of energy and intestinal wet weight absorption as well as prolong gastric emptying of solids and liquids. See Jeppesen, P. B., 2003, "Clinical significance of GLP-2 in short-bowel syndrome," Journal of Nutrition 133 (11): 3721-4. GLP-2 is also reported to stimulate intestinal growth in addition to inhibiting gastric secretion and gastric motility. Burrin et al., 2001, "Glucagon-like peptide 2: a nutrient-responsive gut growth factor," Journal of Nutrition 131 (3): 709. Modulation of GLP-2 secretion through the administration of the compositions described herein can provide for the treatment of short bowel syndrome and compromised intestinal function, including but not limited to, small bowel resection, colitis, enteritis, inflammatory bowel syndrome, ischemic bowel, and chemotherapeutic injury to the intestine.

Delivery to Specific Intestinal Locations

The density of L-cells increases along the length of the intestine with the lowest density at the level of the duodenum and greatest in the rectum. There is an approximately 80-fold increase in L-cell density from the duodenum to rectum as assessed by peptide YY content. See Adrian et al., *Gastroenterology* 1985; 89:1070-77. Given that nutrients or bile salts would not be expected to reach the colon much less the rectum, the mechanism of these L-cells in the regulation of metabolism is not completely clear. While speculative, it is possible that products produced by the colonic flora could inform the gut of the microbial mass and composition via L-cell sensors and in turn this information could be relayed to the CNS via hormonal and neural signals emanating from the colonic and rectal area which is innervated quite differently than the small intestine. Regardless of the role of neuroendocrine cells in the colon and rectum, the basis of this invention is to stimulate these cells wherever they may be (for example, different individuals, and patients with diabetes, might be expected to have different distributions and numbers of these cells) via the presentation of one or more stimuli of taste and/or nutrient receptors and other stimulants for the purpose of treating metabolic disorders.

The upper intestine has different EECs than the lower intestine. For example, CCK and GIP are released from the upper and not typically from the lower intestine, corresponding to I- and K-cells predominantly being located in the upper gut. Conversely, L-cells are located predominantly in the lower intestine. Therefore, hormonal release patterns are not only chemosensory receptor ligand- and combination-specific but also site-specific in the intestine.

In embodiments, it is contemplated that sensing and/or metabolism of nutrients in the upper intestine amplifies certain responses from the lower intestine. Moreover, L-cells located in the upper intestine can behave differently than those in the lower region providing another level control for targeting chemosensory receptor ligands. For example, in embodiments, certain chemosensory receptor ligand combinations delivered to the upper intestine may be more favorable to a hormonal release pattern for the treatment of one disorder, e.g., diabetes, whereas that same combination delivered to the lower intestine may be more appropriate for a different disorder, e.g., obesity. It is also contemplated that the same combination can produce a more favorable hormonal profile when presented to both the upper and lower intestine.

Thus, the embodiments described herein provide a treatment method comprising a combination of chemosensory receptor ligands that is engineered to deliver certain of the chemosensory receptor ligands to one or more locations of the intestine, for example, to optimize hormonal patterns achieved.

In some of the embodiments provided herein, the chemosensory receptor ligands are delivered to one or more regions of the intestine. In some of the embodiments provided herein, the chemosensory receptor ligands are delivered to one or more regions downstream or distal of the stomach. In certain embodiments, the chemosensory receptor ligands are delivered to one or more regions of the upper intestine. In other embodiments, the chemosensory receptor ligands are delivered to the duodenum, jejunum, ileum, or a combination thereof. In certain embodiments, the chemosensory receptor ligands are delivered to one or more regions of the lower intestine. In other embodiments, the chemosensory receptor ligands are delivered to the caecum, colon, rectum, or a combination thereof. In yet other embodiments, the chemosensory receptor ligands are delivered downstream or distal of the duodenum. In additional embodiments, the chemosensory receptor ligands are delivered downstream or distal of the jejunum.

In yet other embodiments, chemosensory receptor ligands are delivered to one or more regions of the upper intestine and one or more regions of the lower intestine. For example, chemosensory receptor ligands can be delivered to the duodenum and the colon. In another non-limiting example, chemosensory receptor ligands can be delivered to the duodenum, jujenum, ileum and colon. In further embodiments, chemosensory receptor ligands are delivered to both the stomach and one or more regions of the intestine. For example, an oral formulation can release some chemosensory receptor ligands in the stomach and later into the intestine. More embodiments are described under Formulations.

Administration of chemosensory receptor ligands to certain regions or locations of the intestine is achieved by any known method. In certain embodiments, enteral administration of chemosensory receptor ligands is performed, e.g., in rodents or man. Intubation cannulation is performed in lightly anaesthetized patients with silastic tubing. Tubing is placed in the post-pyloric region and in the rectum and advanced as deeply as possible. These locations are explored separately and together as foods sensed in the upper intestine can provide signals to the lower intestine and vice versa. In other embodiments, chemosensory receptor ligands are formulated in a modified release composition for oral delivery that delivers the chemosensory receptor ligands to targeted regions or locations of the intestine. In yet other embodiments, chemosensory receptor ligands are formulated for rectal delivery as a suppository, douche, wash, or the like for delivery to targeted regions or locations of the intestinal tract, e.g., rectum or colon. In some aspects, the delivery may start anywhere past the taste buds including partial, substantial, predominant release of chemosensory receptor ligands in the stomach so that the natural flow results in the delivery of the chemosensory receptor ligands to one or more regions of the intestine. This delivery method may be combined with targeted delivery to a specific region of the intestine.

When delivery of chemosensory receptor ligands is to two or more regions of the gastrointestinal tract, the ligands delivered may be in any proportion and manner. In some embodiments, certain chemosensory receptor ligands are be targeted and delivered to specific regions, such as for example, sweet receptor ligands to the ileum and umami receptor ligands to the colon or, in another example, bitter receptor compounds to the stomach, sweet receptor ligands to the duodenum and bile salts to the colon. In other embodiments, chemosensory receptor ligands are delivered in certain proportions in each region of the gut. In one non-limiting example, the quantity of one or more chemosensory receptor ligands can be delivered 20% to the stomach and 80% to intestine, equally in two or more regions of the intestine or any other contemplated proportions.

Administration
Combination Therapies

The compositions of the embodiments described herein may be co-administered with known therapies for the treatment of any of the conditions described herein. Co-administration can also provide for additive or synergistic effects, resulting in the need for lower dosages of a known therapy, the compositions described herein, or both. Additional benefits of co-administration include the reduction in toxicities associated with any of the known therapies.

Co-administration includes simultaneous administration in separate compositions, administration at different times in separate compositions, or administration in a composition in which both agents are present. Thus, in some embodiments, compositions described herein and a known therapy are administered in a single treatment. In some embodiments, the compositions described herein and a known therapy are admixed in a resulting composition. In some embodiments, compositions described herein and the known therapy are administered in separate compositions or administrations.

Administration of compositions described herein and known therapies described herein may be by any suitable means. Administration of a composition described herein and a second compound (e.g., diabetes drug or obesity drug) may be by any suitable means. If the compositions described herein and a second compound are administered as separate compositions, they may be administered by the same route or by different routes. If the compositions described herein and a second compound are administered in a single composition, they may be administered by any suitable route such as, for example, oral administration. In certain embodiments, compositions of chemosensory ligands and second compounds can be administered to the same region or different regions of the gastrointestinal tract. For example, chemosensory ligands can be administered in combination with an anti-diabetic drug to be delivered to the duodenum, jejunum, ileum, or colon.

Therapies, drugs and compounds useful for the treatment of diabetes, metabolic syndrome (including glucose intolerance, insulin resistance, and dyslipidemia), and/or diseases or conditions associated therewith may be administered with the chemosensory receptor ligands. Diabetic therapies drugs and compounds include, but are not limited to, those that decrease triglyceride levels, decrease glucose levels, and/or modulate insulin (e.g. stimulate insulin production, mimic insulin, enhance glucose-dependent insulin secretion, suppress glucagon secretion or action, improve insulin action or insulin sensitizers, or are exogenous forms of insulin).

Drugs that decrease triglyceride level include but are not limited to ascorbic acid, asparaginase, clofibrate, colestipol, fenofibrate mevastatin, pravastatin, simvastatin, fluvastatin, or omega-3 fatty acid. Drugs that decrease LDL cholesterol level include but are not limited to clofibrate, gemfibrozil, and fenofibrate, nicotinic acid, mevinolin, mevastatin, pravastatin, simvastatin, fluvastatin, lovastatin, cholestyrine, colestipol or probucol.

In another aspect, compositions of the embodiments described herein may be administered in combination with glucose-lowering compounds.

The medication classes of thiazolidinediones (also called glitazones), sulfonylureas, meglitinides, biguanides, alpha-glucosidase inhibitors, DPP-IV inhibitors, and incretin mimetics have been used as adjunctive therapies for hyperglycemia and diabetes mellitus (type 2) and related diseases.

Drugs that decrease glucose level include but are not limited to glipizides, glyburides, exenatide (Byetta®), incretins, sitagliptin (Januvia®), pioglitizone, glimepiride, rosiglitazone, metformin, vildagliptin, saxagliptin (Onglyza™), sulfonylureas, meglitinide (e.g., Prandin®) glucosidase inhibitor, biguanides (e.g., Glucophage®), repaglinide, acarbose, troglitazone, nateglinide, natural, synthetic or recombinant insulin and derivatives thereof, and amylin and amylin derivatives. In certain instances, chemosensory receptor ligand compositions provided herein are used in combination with biguanides. Biguanides include metformin, phenformin, buformin and related compounds. In certain instances, chemosensory receptor ligand compositions provided herein are used in combination with metformin.

When administered sequentially, the combination may be administered in two or more administrations. In an alternative embodiment, it is possible to administer one or more chemosensory receptor ligands and one or more additional active ingredients by different routes. The skilled artisan will also recognize that a variety of active ingredients may be administered in combination with one or more chemosensory receptor ligands that may act to augment or synergistically enhance the control prevention, amelioration, attenuation, or treatment of obesity or eating disorders or conditions.

According to the methods provided herein, when co-administered with at least one other obesity reducing (or anti-obesity) or weight reducing drug, a chemosensory receptor ligand(s) may be: (1) co-formulated and administered or delivered simultaneously in a combined formulation; (2) delivered by alternation or in parallel as separate formulations; or (3) by any other combination therapy regimen known in the art. When delivered in alternation therapy, the methods provided may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In certain embodiments, compositions provided herein may be used with other commercially available diet aids or other anti-obesity agents, such as, by way of example, PYY and PYY agonists, GLP-1 and GLP-1 agonists, a DPPIV inhibitor, CCK and CCK agonists, exendin and exendin agonists, GIP and GIP agonists, amylin and amylin agonists, ghrelin modulators (e.g., inhibitors) and leptin and leptin agonists. In certain instances, chemosensory receptor ligand compositions provided herein are used in combination with amylin, amylin agonists or mimetics. Exemplary amylin agonists or mimetics include pramlintide and related compounds. In certain instances, chemosensory receptor ligand compositions provided herein are used in combination with leptin, leptin agonists or mimetics. Additional leptin agonists or mimetics can be identified using the methods described by U.S. Pat. No. 7,247,427 which is incorporated by reference herein. In further instances, chemosensory receptor ligand compositions provided herein increase leptin sensitivity and increase effectiveness of leptin, leptin agonists or mimetics.

Additional anti-obesity agents for use in the methods provided that are in current development are also of interest in the methods of the present invention. Other anti-obesity agents include alone or any combination of phentermine, fenfluramine, sibutramine, rimonabant, topiramate, zonisamide buproprion, naltrexone, lorcaserin, and orlistat. Therapies, drugs and compounds useful for the treatment of weight loss, binge eating, food addictions and cravings may be administered with the compositions described herein. For example, the subject may further be administered at least one other drug which is known to suppress hunger or control appetite. Such therapies drugs and compounds include but are not limited to phenteramines such as Meridia® and Xenical®. Additional therapies, drugs and compounds are known in the art and contemplated herein.

As such, in one aspect, the chemosensory receptor ligands may be used as part of a combination therapy for the control, prevention or treatment of obesity or eating disorders or conditions. Compounds used as part of a combination therapy to treat obesity or reduce weight include, but are not limited to, central nervous system agents that affect neurotransmitters or neural ion channels, including antidepressants (bupropion), noradrenalin reuptake inhibitors (GW320659), selective serotonin 2c receptor agonists, selective 5HT 2c receptor agonists, antiseizure agents (topiramate, zonisamide), some dopamine antagonists, and cannabinoid-1 receptor antagonists (CB-1 receptor antagonists) (rimonabant); leptin/insulin/central nervous system pathway agents, including leptin analogues, leptin transport and/or leptin receptor promoters, ciliary neurotrophic factor (Axokine), neuropeptide Y and agouti-related peptide antagonists, pro-opiomelanocortin and cocaine and amphetamine regulated transcript promoters, .alpha.-melanocyte-stimulating hormone analogues, melanocoritin-4 receptor agonists, and agents that affect insulin metabolism/activity, which include protein-tyrosine phosphatase-1B inhibitors, peroxisome proliferator activated receptor-.gamma. receptor antagonists, short-acting bromocriptine (ergoset), somatostatin agonists (octreotide), and adiponectin/Acrp30 (Famoxin or Fatty Acid Metabolic Oxidation Inducer); gastrointestinal-neural pathway agents, including those that increase cholecystokinin activity (CCK), PYY activity, NPY activity, and PP activity, increase glucagon-like peptide-1 activity (exendin 4, liraglutide, dipeptidyl peptidase IV inhibitors), and those that decrease ghrelin activity, as well as amylin analogues (pramlintide); agents that may increase resting metabolic rate (selective β-3 stimulators/agonist, uncoupling protein homologues, and thyroid receptor agonists); other more diverse agents, including melanin concentrating hormone antagonists, phytostanol analogues, functional oils, P57, amylase inhibitors, growth hormone fragments, synthetic analogues of dehydroepiandrosterone sulfate, antagonists of adipocyte 11B-hydroxysteroid dehydrogenase type 1 activity, corticotropin-releasing hormone agonists, inhibitors of fatty acid synthesis (cerulenin and C75), carboxypeptidase inhibitors, indanone/indanols, aminosterols (trodusquemine/trodulamine), and other gastrointestinal lipase inhibitors (ATL962); amphetamines, such as dextroamphetamine; other sympathomimetic adrenergic agents, including phentermine, benzphetamine, phendimetrazine, mazindol, and diethylpropion.

Other compounds include ecopipam; oxyntomodulin (OM); inhibitors of glucose-dependent insulinotropic polypeptide (GIP); gastrin-releasing peptide; neuromedin B; enterostatin; amfebutamone, SR-58611; CP-045598; AOD-0604; QC-BT16; rGLP-1; 1426 (HMR-1426); N-5984; ISIS-113715; solabegron; SR-147778; Org-34517; melanotan-II; cetilistat; c-2735; c-5093; c-2624; APD-356; radafaxine; fluasterone; GP-389255; 856464; S-2367; AVE-1625; T-71; oleoyl-estrone; peptide YY [3-36] intranasal; androgen receptor agonists; PYY 3-36; DOV-102677; tagatose; SLV-319; 1954 (Aventis Pharma AG); oxyntomodulin, Thiakis; bromocriptine, PLIVA; diabetes/hyperlipidemia therapy, Yissum; CKD-502; thyroid receptor beta agonists; beta-3 adrenoceptor agonist; CDK-A agonists; galanin antagonist; dopamine D1/D2 agonists; melanocortin modulators; verongamine; neuropeptide Y antagonists; melanin-concentrating hormone receptor antagonists; dual PPAR alpha/gamma agonists; CGEN-P-4; kinase inhibitors; human MCH receptor antagonists; GHS-R antagonists; ghrelin receptor agonists; DG70 inhibitors; cotinine; CRF-BP inhibitors; urocortin agonists; UCL-2000; impentamine; .beta.-3 adrenergic receptor; pentapeptide MC4 agonists; trodusquemine; GT-2016; C-75; CPOP; MCH-1 receptor antagonists; RED-103004; aminosterols; orexin-1 antagonists; neuropeptide Y5 receptor antagonists; DRF-4158; PT-15; PTPase inhibitors; A37215; SA-0204; glycolipid metabolites; MC-4 agonist; produlestan; PTP-1B inhibitors; GT-2394; neuropeptide Y5 antagonists; melanocortin receptor modulators; MLN-4760; PPAR gamma/delta dual agonists; NPY5RA-972; 5-HT2C receptor agonist; neuropeptide Y5 receptor antagonists (phenyl urea analogs); AGRP/MC4 antagonists; neuropeptide Y5 antagonists (benzimidazole); glucocorticoid antagonists; MCHR1 antagonists; Acetyl-CoA carboxylase inhibitors; R-1496; HOB1 modulators; NOX-B11; peptide YY 3-36 (eligen); 5-HT 1 modulators; pancreatic lipase inhibitors; GRC-1087; CB-1 antagonists; MCH-1 antagonists; LY-448100; bombesin BRS3 agonists; ghrelin antagonists; MC4 antagonists; stearoyl-CoA desaturase modulators; H3 histamine antagonists; PPARpan agonists; EP-01492; hormone-sensitive lipase inhibitors; fatty acid-binding protein 4 inhibitors; thiolactone derivatives; protein tyrosine phosphatase 1B inhibitors; MCH-1 antagonist; P-64; PPAR gamma ligands; melanin concentrating hormone antagonists; thiazole gastroprokinetics; PA-452; T-226296; A-331440; immunodrug vaccines; diabetes/obesity therapeutics (Bioagency, Biofrontera Discovery GmbH); P-7 (Genfit); DT-011 M; PTP1B inhibitor; anti-diabetic peptide conjugates; KATP agonists; obesity therapeutics (Lexicon); 5-HT2 agonists; MCH-1 receptor antagonists; GMAD-1/GMAD-2; STG-a-MD; neuropeptide Y antagonist; angiogenesis inhibitors; G protein-coupled receptor agonists; nicotinic therapeutics (ChemGenex); anti-obesity agents (Abbott); neuropeptide Y modulators; melanin concentrating hormone; GW-594884A; MC-4R agonist; histamine H3 antagonists; orphan GPCR modulators; MITO-3108; NLC-002; HE-2300; IGF/IBP-2-13; 5-HT2C agonists; ML-22952; neuropeptide Y receptor antagonists; AZ-40140; anti-obesity therapy (Nisshin Flour); GNTI; melanocortin receptor modulators; alpha-amylase inhibitors; neuropeptide Y1 antagonist; beta-3 adrenoceptor agonists; ob gene products (Eli Lilly & Co.); SWR-0342-SA; beta-3 adrenoceptor agonist; SWR-0335; SP-18904; oral insulin mimetics; beta 3 adrenoceptor agonists; NPY-1 antagonists; .beta.-3 agonists; obesity therapeutics (7™ Pharma); 11beta-hydroxysteroid dehydrogenase (HSD)1 inhibitors; QRX-431; E-6776; RI-450; melanocortin-4 antagonists; melanocortin 4 receptor agonists; obesity therapeutics (CuraGen); leptin mimetics; A-74498; second-generation leptin; NBI-103; CL-314698; CP-114271; beta-3 adrenoceptor agonists; NMI-8739; UCL-1283; BMS-192548; CP-94253; PD-160170; nicotinic agonist; LG-100754; SB-226552; LY-355124; CKD-711; L-751250; PPAR inhibitors; G-protein therapeutics; obesity therapy (Amylin Pharmaceuticals Inc.); BW-1229; monoclonal antibody (ObeSys/CAT); L-742791; (S)-sibutramine; MBU-23; YM-268; BTS-78050; tubby-like protein genes; genomics (eating disorders; Allelix/Lilly); MS-706; GI-264879A; GW-409890; FR-79620 analogs; obesity therapy (Hybrigenics SA); ICI-198157; ESP-A; 5-HT2C agonists; PD-170292; AIT-202; LG-100641; GI-181771; anti-obesity therapeutics (Genzyme); leptin modulator; GHRH mimetics; obesity therapy (Yamanouchi Pharmaceutical Co. Ltd.); SB-251023; CP-331684; BIBO-3304; cholesten-3-ones; LY-362884; BRL-48962; NPY-1 antagonists; A-71378; .RTM.-didesmethylsibutramine; amide derivatives; obesity therapeutics (Bristol-Myers Squibb Co.); obesity therapeutics (Ligand Pharmaceuticals Inc.); LY-226936; NPY antagonists; CCK-A agonists; FPL-14294; PD-145942; ZA-7114; CL-316243; SR-58878; R-1065; BIBP-3226; HP-228; talibegron; FR-165914; AZM-008; AZM-016; AZM-120; AZM-090; vomeropherin; BMS-187257; D-3800; AZM-131; gene discovery (Axys/Glaxo); BRL-26830A; SX-013; ERR modulators; adipsin; AC-253; A-71623; A-68552; BMS-210285; TAK-677; MPV-1743; obesity therapeutics (Modex); GI-248573; AZM-134; AZM-127; AZM-083; AZM-132; AZM-115; exopipam; SSR-125180; obesity therapeutics (Melacure Therapeutics AB); BRL-35135; SR-146131; P-57; AZM-140; CGP-71583A; RF-1051; BMS-196085; manifaxine; beta-3 agonists; DMNJ (Korea Research Institute of Bioscience and Biotechnology); BVT-5182; LY-255582; SNX-024; galanin antagonists; neurokinin-3 antagonists; dexfenfluramine; mazindol; diethylpropion; phendimetrazine; benzphetamine; amfebutmone; sertraline; metformin; AOD-9604; ATL-062; BVT-933; GT389-255; SLV319; HE-2500; PEG-axokine; L-796568; and ABT-239.

In some embodiments, compounds for use in combination with a chemosensory receptor ligand composition provided herein include rimonabant, sibutramine, orlistat, PYY or an analog thereof, CB-1 antagonist, leptin, phentermine, and exendin analogs. Exemplary dosing ranges include phentermine resin (30 mg in the morning), fenfluramine hydrochloride (20 mg three times a day), and a combination of phentermine resin (15 mg in the morning) and fenfluramine hydrochloride (30 mg before the evening meal), and sibutramine (10-20 mg). Weintraub et al. (1984) Arch. Intern. Med. 144:1143-1148.

In some embodiments, a chemosensory receptor ligand composition provided herein is used as an adjunctive therapy to a bariatric surgical procedure. Bariatric surgery is a procedure for weight loss and relates to modifications with the gastrointestinal tract and includes such procedures as gastric banding, sleeve gastrectomy, GI bypass procedure (e.g., roux en Y, biliary duodenal bypass, loop gastric bypass), intragastric balloon, vertical banded, gastroplasty, endoluminal sleeve, biliopancreatic diversion, and the like. In certain instances, a chemosensory receptor ligand composition is adjunctive to gastric banding. In certain instances, a chemosensory receptor ligand composition is adjunctive to GI bypass procedures. In yet other instances, a chemosensory receptor ligand composition is adjunctive to sleeve gastrectomy. In certain embodiments, a chemosensory receptor ligand composition as an adjunctive therapy to bariatric surgery is administered prior to the bariatric procedure. In certain embodiments, a chemosensory receptor ligand composition as an adjunctive therapy to bariatric surgery is administered after the bariatric procedure. In certain instances, when used as adjunctive therapy, the dosage and amounts of a chemosensory receptor ligand composition may be adjusted as needed with respect to the bariatric procedure. For example, amounts of a chemosensory receptor ligand composition administered as an adjunct therapy to a bariatric procedure may be reduced by one-half of normal dosages or as directed by a medical professional.

Combination therapy can be exploited, for example, in modulating metabolic syndrome (or treating metabolic syndrome and its related symptoms, complications and disorders), wherein chemosensory receptor ligand compositions provided herein can be effectively used in combination with, for example, the active agents discussed above for modulating, preventing or treating diabetes, obesity, hyperlipidemia, atherosclerosis, and/or their respective related symptoms, complications and disorders.

Formulations

Formulations for the compositions provided herein include those suitable for oral or rectal administration, and administration although the most suitable route can depend upon for example the condition and disorder of the recipient. The formulations can conveniently be presented in unit dosage form and can be prepared by any of the methods well known in the art of pharmacy. All methods include the step of bringing into association the active ingredient with the carrier which constitutes one or more accessory ingredients.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion.

Composition preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

For buccal or sublingual administration, the compositions can take the form of tablets, lozenges, pastilles, or gels formulated in conventional manner. Such compositions can comprise the active ingredient in a flavored basis such as sucrose and acacia or tragacanth. Such compositions can be formulated to delivery chemosensory receptor ligands to a desired area in the gastrointestinal system.

It should be understood that in addition to the ingredients particularly mentioned above, the compounds and compositions described herein can include other agents conventional in the art having regard to the type of formulation in question, for example those suitable for oral administration can include flavoring agents.

The compositions described herein can also contain chemosensory receptor ligands in a form suitable for oral use, for example, as tablets, troches, lozenges, aqueous or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents selected from, by way of non-limiting example, sweetening agents, flavoring agents, coloring agents and preserving agents in order to provide pharmaceutically elegant and palatable preparations.

Tablets contain the active ingredient in admixture with pharmaceutically acceptable excipients which are suitable for the manufacture of tablets. These excipients can be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets can be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate can be employed as appropriate. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

In various embodiments, the chemosensory receptor ligand compositions provided herein are in liquid form. Liquid forms include, by way of non-limiting example, neat liquids, solutions, suspensions, dispersions, colloids, foams and the like. In certain instances, liquid forms contain also a nutritional component or base (e.g., derived from milk, yoghurt, shake, or juice). In some aspects, the chemosensory receptor ligands are micronized or as nanoparticles in the liquid form. In certain instances, the chemosensory receptor ligands are coated to mask the tastant properties. In other instances, the chemosensory receptor ligands are coated to modify delivery to the intestine and colon.

Aqueous solutions or suspensions contain the active ingredient(s) in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous solutions or suspensions can also contain one or more preservatives, for example ethyl, or n-propyl p-hydroxybenzoate, one or more coloring agents, one or more flavoring agents, and one or more sweetening agents, such as sucrose, saccharin or aspartame. In certain instances, the flavoring agents are chemosensory receptor ligands.

Oily suspensions can be formulated by suspending the active ingredient(s) in a vegetable oil, for example arachis oil, olive oil, sesame oil or coconut oil, or in mineral oil such as liquid paraffin. The oily suspensions can contain a thickening agent, for example beeswax, hard paraffin or cetyl alcohol. Sweetening agents such as those set forth above, and flavoring agents can be added to provide a palatable oral preparation. These compositions can be preserved by the addition of an anti-oxidant such as butylated hydroxyanisol or alpha-tocopherol.

Dispersible powders and granules suitable for preparation of an aqueous solutions or suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, can also be present. These compositions can be preserved by the addition of an anti-oxidant such as ascorbic acid.

Compositions can also be in the form of an oil-in-water emulsion. The oily phase can be a vegetable oil, for example olive oil or arachis oil, or a mineral oil, for example liquid paraffin or mixtures of these. Suitable emulsifying agents can be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions can also contain sweetening agents, flavoring agents, preservatives and antioxidants.

Syrups and elixirs can be formulated with sweetening agents, for example glycerol, propylene glycol, sorbitol or sucrose. Such formulations can also contain a demulcent, a preservative, flavoring and coloring agents and antioxidant.

Compositions can also be formulated in rectal compositions such as suppositories or retention enemas, e.g., containing conventional suppository bases such as cocoa butter, polyethylene glycol, or other glycerides. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

The composition can, for example, be in a form suitable for oral administration as a tablet, capsule, cachet, pill, lozenge, powder or granule, sustained release formulations, solution, liquid, or suspension. The pharmaceutical composition can be in unit dosage forms suitable for single administration of precise dosages. The pharmaceutical composition will include a conventional pharmaceutical carrier or excipient and the compound according to the invention as an active ingredient. In addition, it can include other medicinal or pharmaceutical agents, carriers, adjuvants, etc.

Suitable carriers include inert diluents or fillers, water and various organic solvents. The compositions can, if desired, contain additional ingredients such as flavorings, binders, excipients and the like. Thus for oral administration, tablets containing various excipients, such as citric acid can be employed together with various disintegrants such as starch or other cellulosic material, alginic acid and certain complex silicates and with binding agents such as sucrose, gelatin and acacia. Additionally, lubricating agents such as magnesium stearate, sodium lauryl sulfate and talc are often useful for tableting purposes. Other reagents such as an inhibitor, surfactant or solubilizer, plasticizer, stabilizer, viscosity increasing agent, or film forming agent can also be added. Solid compositions of a similar type can also be employed in soft and hard filled gelatin capsules. Materials include lactose or milk sugar and high molecular weight polyethylene glycols. When aqueous suspensions or elixirs are desired for oral administration the active compound therein can be combined with various sweetening or flavoring agents, coloring matters or dyes and, if desired, emulsifying agents or suspending agents, together with diluents such as water, ethanol, propylene glycol, glycerin, or combinations thereof.

Also contemplated within the invention are food compositions, including medical food compositions and formulations containing the compositions of the invention described herein, as well as nutritional or dietary supplements incorporating the compositions of the invention. Foods, such as medical foods, incorporating the compositions of the invention include edible forms such as bars, candies, powders, gels, and liquids. The medical food compositions can be formulated to control the amounts and types of chemosensory receptor ligands as well as the content of other edible additives and ingredients (e.g., carbohydrates, proteins, fats, fillers, excipients). Exemplary medical food compositions include, but are not limited to, bars with defined and/or limited metabolites and nonmetabolized chemosensory receptor ligands. Edible candies, gels, and liquids can also be formulated with defined ingredients as well as the compositions described herein.

Modified Release Formulations

In various embodiments, the methods and compositions directed to chemosensory receptor ligand(s) are provided in the form of controlled, sustained, or extended release formulations, known collectively as "modified release" formulations. Compositions can be administered by modified release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Such dosage forms can be used to provide modified release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable modified release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled- or sustained-release.

Many strategies can be pursued to obtain modified release in which the rate of release outweighs, if any, the rate of metabolism of the chemosensory receptor ligands and/or the location of the release is controlled. For example, modified release can be obtained by the appropriate selection of formulation parameters and ingredients (e.g., appropriate controlled release compositions and coatings). Examples include single or multiple unit tablet or capsule compositions, oil solutions, suspensions, emulsions, microcapsules, microspheres, nanoparticles, patches, and liposomes. The release mechanism can be controlled such that the compounds are released at period intervals, the release could be simultaneous, a delayed release of one of the agents of the combination can be affected, when the early release of one particular agent is preferred over the other, or the location of the release is controlled (e.g., release in the lower intestine tract, upper intestine tract, or both, depending upon the number and type of compositions to be administered, the desired effect of the compositions, and the desired location of release for each ligand). Different delivery systems described herein can also be combined to release at an onset of multiple period intervals (e.g., about 30 minutes, about 120 minutes, about 180 minutes and about 240 minutes after oral administration) or at different locations (e.g., release in the lower intestine tract, upper intestine tract, the duodenum, jejunum, ileum, caecum, colon, and/or rectum) or a combination thereof. For example, a pH dependent system can be combined with a timed release system or any other system described herein to achieve a desired release profile.

In some embodiments, the modified release systems are formulated to release a chemosensory receptor ligand(s) at a duration of about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to onset of the release. In embodiments with multiple releases, modified release systems are formulated to release at more than one durations of time at different time points.

In various embodiments, the chemosensory receptor ligand compositions(s) are provided in the form of modified release formulations coupled with an immediate release component in a unitary dosage form. The immediate release component can be a can be formulated by any known method such as a layer that envelops the modified release component or the like. Exemplary ratios of immediate release ("IR") of an active agent to a modified release ("MR") of an active agent are about 10% IR to about 90% MR, about 15% IR to about 85% MR, about 20% IR to about 80% MR, about 25% IR to about 75% MR, about 30% IR to about 70% MR, about 35% IR to about 65% MR, about 40% IR to about 60% MR, about 45% IR to about 55% MR, or about 50% IR to about 50% MR. In certain embodiments, the immediate release of an active agent to modified release of an active agent is about 25% IR to about 75% MR. In other embodiments, the immediate release of an active agent to modified release of an active agent is about 20% IR to about 80% MR. Unitary dosage forms with an IR and MR component include any known formulation including bilayer tablets, coated pellets, and the like.

Timed Release Systems

In one embodiment, the release mechanism is a "timed" or temporal release ("TR") system that releases an active agent, for example a chemosensory receptor ligand(s), at certain timepoints subsequent to administration. Timed release systems are well known in the art and suitable timed release system can include any known excipient and/or coating. For example, excipients in a matrix, layer or coating can delay release of an active agent by slowing diffusion of the active agent into an environment. Suitable timed release excipients, include but are not limited to, acacia (gum arabic), agar, aluminum magnesium silicate, alginates (sodium alginate), sodium stearate, bladderwrack, bentonite, carbomer, carrageenan, Carbopol, cellulose, microcrystalline cellulose, ceratonia, chondrus, dextrose, furcellaran, gelatin, Ghatti gum, guar gum, galactomannan, hectorite, lactose, sucrose, maltodextrin, mannitol, sorbitol, honey, maize starch, wheat starch, rice starch, potato starch, gelatin, sterculia gum, xanthum gum, Glyceryl behenate (e.g., Compritol 888 ato), Glyceryl distearate (e.g. Precirol ato 5), polyethylene glycol (e.g., PEG 200-4500), polyethylene oxide, adipic acid, gum tragacanth, ethyl cellulose (e.g., ethyl cellulose 100), ethylhydroxyethyl cellulose, ethylmethyl cellulose, methyl cellulose, hydroxyethyl cellulose, hydroxyethylmethyl cellulose (e.g., K100LV, K4M, K15M), hydroxypropyl cellulose, poly(hydroxyethyl methacrylate), cellulose acetate (e.g. cellulose acetate CA-398-10 NF), cellulose acetate phthalate, cellulose acetate propionate, cellulose acetate butyrate, hydroxypropyl methyl cellulose acetate succinate, hydroxypropyl methyl cellulose phthalate, cellulose butyrate, cellulose nitrate, oxypolygelatin, pectin, polygeline, povidone, propylene carbonate, polyandrides, methyl vinyl ether/maleic anhydride copolymer (PVM/MA), poly(methoxyethyl methacrylate), poly(methoxyethoxyethyl methacrylate), hydroxypropyl cellulose, hydroxypropylmethyl cellulose, sodium carboxymethyl-cellulose (CMC), silicon dioxide, vinyl polymers, e.g. polyvinyl pyrrolidones (PVP: povidone), polyvinyl acetates, or polyvinyl acetate phthalates and mixtures, Kollidon SR, acryl derivatives (e.g. polyacrylates, e.g. cross-linked polyacrylates, methycrylic acid copolymers), Splenda® (dextrose, maltodextrin and sucralose) or combinations thereof. The timed release excipient may be in a matrix with active agent, in another compartment or layer of the formulation, as part of the coating, or any combination thereof. Varying amounts of one or more timed release excipients may be used to achieve a designated release time.

In some embodiments, the timed release systems are formulated to release a chemosensory receptor ligand(s) at an onset of about 5 minutes, about 10 minutes, about 20 minutes, about 30 minutes, about 40 minutes, about 50 minutes, about 60 minutes, about 70 minutes, about 80 minutes, about 90 minutes, about 100 minutes, about 110 minutes, about 120 minutes, about 130 minutes, about 140 minutes, about 150 minutes, about 160 minutes, about 170 minutes, about 180 minutes, about 190 minutes, about 200 minutes, about 210 minutes, about 220 minutes, about 230 minutes, about 240 minutes, about 250 minutes, about 260 minutes, about 270 minutes, about 280 minutes, about 290 minutes, about 300 minutes, about 310 minutes, about 320 minutes, about 330 minutes, about 340 minutes, about 350 minutes, about 360 minutes, about 370 minutes, about 380 minutes, about 390 minutes, about 400, about 400, about 410, or about 420 minutes subsequent to administration. In embodiments with multiple releases, timed release systems are formulated to release at more than one time point. In certain embodiments, the timed release systems are formulated to release at an onset of about 10 minutes, about 30 minutes, about 120 minutes, about 180 minutes and about 240 minutes after administration. In other embodiments o the timed release systems are formulated to release at an onset of about 5 to about 45 minutes, about 105 to about 135 minutes, about 165 to about 195 minutes, about 225 to about 255 minutes or a combination of times thereof following administration to a subject.

In various embodiments, the methods and compositions directed to chemosensory receptor ligand(s) are provided in the form of timed release formulations coupled with an immediate release component in a unitary dosage form. The immediate release component can be a can be formulated by any known method such as a layer that envelops the timed release component or the like. The timed release component can be formulated to release at exemplary times previously described. Exemplary ratios of immediate release ("IR") of an active agent to a timed release ("TR") of an active agent are about 10% IR to about 90% TR, about 15% IR to about 85% TR, about 20% IR to about 80% TR, about 25% IR to about 75% TR, about 30% IR to about 70% TR, about 35% IR to about 65% TR, about 40% IR to about 60% TR, about 45% IR to about 55% TR, or about 50% IR to about 50% TR. In certain embodiments, the immediate release of an active agent to timed release of an active agent is about 25% IR to about 75% TR. In other embodiments, the immediate release of an active agent to timed release of an active agent is about 20% IR to about 80% TR.

Enteric Coatings and pH Dependent Systems

The formulation may also be coated with an enteric coating, which protects an active agent, for example a chemosensory receptor ligand(s), from degradation in an acidic environment, such as the stomach, and allows a delayed release into a target area, for example the duodenum, for uptake.

The enteric coating may be, as a non-limiting example, wax or wax like substance, such as carnauba wax, fatty alcohols, hydrogenated vegetable oils, zein, shellac, sucrose, Arabic gum, gelatin, dextrin, psyllium husk powder, polymethacrylates, anionic polymethacrylates, mixtures of poly (methacrylic acid, methyl methacrylate), polymers or copolymers derived from acrylic and/or methacrylic acid esters, cellulose acetate phthalate, cellulose acetate trimellitate, hydroxypropyl methylcellulose phthalate (HPMCP), cellulose propionate phthalate, cellulose acetate maleate, polyvinyl alcohol phthalate, hydroxypropyl methylcellulose acetate succinate (HPMCAS), hydroxypropyl methylcellulose hexahydrophthalate, polyvinyl acetate phthalate, mixtures of poly(methacrylic acid, ethyl acrylate), ethylcellulose, methylcellulose, propylcellulose, chitosan succinate, chitosan succinate, polyvinyl acetate phthalate (PVAP), polyvinyl acetate polymers carboxymethylethyl cellulose and compatible mixtures thereof. In addition, an inactive intermediate film may be provided between the active agent, for example, a chemosensory receptor ligand(s), and the enteric coating to prevent interaction of the active agent with the enteric coating.

The enteric coatings can be formulated to release the active agent, for example, a chemosensory receptor ligand(s), at a desired pH using combinations of enteric polymers. It is well-known that different locations of the gastrointestinal system have specific pHs. For example, the duodenum may correspond to a pH 5.5 environment and the jejunum may correspond to pH 6.0 environment. In some embodiments, the enteric coatings are formulated to release a chemosensory receptor ligand(s) at an onset of a pH including about pH 1, about pH 1.5, about pH 2, about pH 2.5, about pH 3, about pH 3.5, about pH 4, about pH 4.5, about pH 5, about pH 5.5, about pH 6, about pH 6.5, or about pH 7. In embodiments with multiple releases, the enteric coatings are formulated to release at an onset of two or more pH values. In certain embodiments, the enteric coatings are formulated to release at an onset of pH 5.5, 6.0, 6.5 and 7.0. In certain embodiments, the enteric coatings are formulated to release at an onset of pH 5.5, 6.0 and 6.5. In other embodiments, the enteric coatings are formulated to release at the duodenum, jejunum, ileum, and lower intestine. In yet other embodiments, the enteric coatings are used in combination with other release systems such as a timed release system.

In yet other embodiments, the enteric coatings are used in combination with an immediate release/modified release unitary dosage forms. For example, an unitary dosage form, such as a bilayer tablet with a 20% IR/80% MR component of chemosensory receptor ligand(s) can be coated with an enteric coating that releases at pH 6.5 so that the release is delayed until the dosage form reaches a pH of 6.5, thereby releasing the IR component immediately and the MR component according to its MR release properties. In certain instances, the enteric coatings are used in combination with an immediate release/timed release unitary dosage forms.

Gastro-Retentive Systems

Described herein are dosage forms exhibiting extended gastric residence, possessing some resistance to the pattern of waves of motility present in the gastrointestinal tract that serve to propel material through it. This is achieved, in some embodiments, by simultaneously providing the dosage form with a combination of gastric residence extending characteristics, including floatation in gastric fluid, adhesion to the mucosal surfaces of the gastrointestinal tract, and swelling to a size which delays passage through the pylorus. In some embodiments, formation of microgels occurs upon exposure to gastric fluid.

With the teachings described herein, those of skill in the art will be able to make and use the compositions encompassed by the methods of the present invention. In some embodiments, gastro-retentive (sustained-release) systems described herein are used in the methods of the present invention.

Floating Properties

The floating property of the dosage form is designed to have low density and thus float on gastric fluids until the dosage form either disintegrates (and the resultant particles empty from the stomach) or absorbs fluid to the point that it no longer floats and can pass more easily from the stomach with a wave of motility responsible for gastric emptying.

In some of the embodiments described herein, while the system is floating on the gastric contents, the active ingredient is released slowly at the desired rate from the system. After release of active ingredient, the residual system is emptied from the stomach. The system may require minimum gastric contents (at least about 200 mL) needed to achieve proper floating principle, which can be accomplished by taking the dosage form with a cup of water. Also a minimal level of floating force (F) is required to keep the dosage form reliably buoyant on the surface of the stomach contents/meal.

Depending on the desired properties of the composition, it may be useful to use one or more of the following systems single- and multiple-unit hydrodynamically balanced systems (HBS), single and multiple-unit gas generating systems, hollow microspheres, and raft-forming systems. Various factors such as gastrointestinal physiology, dosage form characteristics, and patient-related factors will influence the dosage form buoyancy. With the knowledge in the art and the teaching provided herein, skilled artisans will readily know how to implement these systems.

The floating dosage forms can be prepared where buoyancy is created via three possible mechanisms. The first mechanism is the incorporation of formulation components with sufficiently low density to enable floating on the stomach contents. Such systems need not disintegrate into small pieces to empty from the stomach, but rather slowly erode, gradually losing buoyancy and eventually being expelled from the stomach. This approach may be especially useful for active ingredients or other active ingredients administered in low doses (a few hundred milligrams per day or less) or having low water solubility. However, these properties have limited utility where higher doses are required or with highly water soluble active ingredients. In these instances, large amounts of polymer would be needed to retard drug or active ingredient release. Depending on the amount of polymer, a capsule dosage form may not be practicable due to size constraints. Furthermore, homogenous distribution of drugs or other active ingredients in a tablet of this form can be accompanied by an undesirable, rapid initial release of drug or active ingredient. Again, this is most often seen with very water soluble drugs or active ingredients.

The second mechanism is the formation of a bilayer dosage form where the buoyancy originates from a separate layer to the active layer. This approach can overcome some of the problems encountered with the system discussed above.

The third mechanism is the incorporation of one or more gas generating agents. Gas generating agents react with gastric fluid to generate gas. This gas is subsequently entrapped within the dosage form which results in floatation in the gastric fluid. This approach may offer improved control over degree, onset time and persistence of floatation. U.S. Pat. No. 4,844,905, describes a system with a active ingredient loaded core surrounded by a gas generating layer, which in turn was surrounded by a polymeric layer responsible for controlling active ingredient release from the system. In some embodiments, the gas generating component upon interaction with gastric fluid generates carbon dioxide or sulfur dioxide that becomes entrapped within the hydrated microgel matrix of the gelling agent.

The gas generating components useful in the compositions described herein include, but are not limited to, a combination of one or more of bicarbonate and carbonate salts of Group I and Group II metals, including sodium, potassium, and calcium water soluble carbonates, sulfites and bicarbonates such as sodium carbonate, sodium bicarbonate, sodium metabisulfite, calcium carbonate. The gas generating component can be present in an amount from about 2-50 wt-%.

Floating tablets can have a bulk density less than gastric fluid so that they remain buoyant in the stomach without affecting the gastric emptying rate for a prolonged period of time.

Limitations of floating dosage forms include required administration with a suitable amount of fluid (normal gastric contents could be as little as a few tens of milliliters) and their possible posture dependence. A patient sitting upright may ensure prolonged gastric residence of a buoyant dosage form, whereas a supine patient might allow ready presentation of the floating dosage form to the pylorus and thus allow rapid exit of the dosage form from the stomach (see Timmermans et al, J. Pharm. Sci. 1994, 83, 18-24).

Bioadhesive Properties

Bioadhesive delivery systems are designed to imbibe gastric fluid such that the outer layer becomes a viscous, tacky material that adheres to the gastric mucosa/mucus layer. This increases gastric retention until the adhesive forces are weakened for example by continuing hydration of the outer layer of the dosage form or by the persistent application of shear. Polycarbophil has been identified as a suitable polymer for adhesion of orally administered dosage forms to the gastric mucosa, (see Longer et al, J. Pharm. Sci., 1985, 74, 406-411). It should be noted that the success observed in animal models with such systems has been found to be unreliable in translating to humans due to differences in mucous amounts, consistency and turnover differences between animals and humans.

As described herein, the combination of bioadhesiveness with low density materials (i.e. less dense than gastric fluid) maintain floating while prolonging the gastric retention time (GRT) by allowing the composition to float in the upper region of the stomach. Because the dosage form also has bioadhesive characteristics, in some embodiments, the dosage form will also attach itself to gastric mucosa.

Swelling Properties

The compositions described herein should be of a size that allows the dosage form to be swallowed. After ingestion, the compositions described herein swell. In some embodiments, the compositions swell to a size that precludes passage through the pylorus until after active ingredient release has progressed to a required degree.

The dosage forms described herein can comprise hydrophilic erodible polymers. In these embodiments, upon imbibing gastric fluid the dosage form swells over a short period of time to a size that will encourage prolonged gastric retention. This allows for the sustained delivery of the active ingredient to the absorption site. In some embodiments, the absorption site of the active ingredient is in the upper gastrointestinal tract.

When the dosage forms are made of an erodible, hydrophilic polymer(s), they readily erode over a reasonable time period to allow passage from the stomach. The time period of expansion is such that this will not occur in the esophagus and if the dosage form passes into the intestine in a partially swollen state, the erodibility and elastic nature of the hydrated polymer will eliminate the chance of intestinal obstruction by the dosage form.

Various types of polymers are available to provide systems that will swell and then gradually release active ingredient from the swollen dosage forms. For example, active ingredient dissolution dosage forms can comprise linear hydrophilic polymers. Upon hydration, these linear hydrophilic polymers, which do not have a covalently cross-linked structure, can form a gelatinous layer on the surface of the dosage form. The thickness and durability of this gelatinous layer depends on a number of factors such as the concentration, molecular weight and viscosity of the polymer(s) comprising the dosage form. At higher concentrations the linear polymer chains entangle to a greater degree. This can result in virtual cross-linking and the formation of a stronger gel layer. As the swollen linear chains of the hydrophilic polymer dissolve, the gel layer erodes and the active ingredient is released. In these embodiments, the rate of dosage form erosion helps control the release rate of the active ingredient.

Cross-linked polymers such as polyacrylic acid polymer (PAA) may be used in the dosage form matrix. In the dry state, dosage forms formulated with cross-linked polyacrylic acid polymers contain the active ingredient trapped within a glassy core. As the external surface of the tablet is hydrated, it forms a gelatinous layer. It is believed that this layer is different than traditional matrices because the hydrogels are not entangled chains of polymer, but discrete microgels made up of many polymer particles. The crosslink network enables the entrapment of active ingredients in the hydrogel domains. Because these hydrogels are not water soluble, they do not dissolve or erode in the same manner as linear polymers. Instead, when the hydrogel is fully hydrated, osmotic pressure from within works to break up the structure by sloughing off discrete pieces of the hydrogel. The active ingredient is able to diffuse through the gel layer at a uniform rate.

Though not wishing to be bound by any particular theory, it is postulated that as the concentration of the active ingredient increases within the gel matrix and its thermodynamic activity or chemical potential increases, the gel layer around the active ingredient core acts as a rate controlling membrane, which results in a linear release of the active ingredient. With these systems, active ingredient dissolution rates are affected by subtle differences in rates of hydration and swelling of the individual polymer hydrogels. These properties of the polymer hydrogels are dependent on various factors such as the molecular structure of the polymers, including crosslink density, chain entanglement, and crystallinity of the polymer matrix. The extent and rate of swelling is also dependent on pH and the dissolution medium. The channels that form between the polymer hydrogels are also influenced by the concentration of the polymer and the degree of swelling. Increasing the amount of polymer or the swelling degree of the polymer decreases the size of the channels.

Cross-linked polyacrylic acid polymers provide rapid and efficient swelling characteristics in both simulated gastric fluid (SGF) and simulated intestinal fluid (SIF) and produce dosage forms of excellent hardness and low friability. Moreover, cross-linked polyacrylic acid polymers may also provide longer dissolution times at lower concentrations than other excipients.

Compound solubility is also important to active ingredient release from dosage forms comprising cross-linked polyacrylic acid polymers. Poorly soluble compounds tend to partition into the more hydrophobic domains of the system, such as the acrylic backbone of the polymer. Highly water soluble compounds undergo diffusion controlled-release due to the fast dissolution of the active ingredient through the water-filled interstitial spaces between the microgels.

With the combination of sufficient swelling, floatation and/or bioadhesion properties, the dosage forms described and useful in the present invention achieve gastric retention regardless of whether the subject is in the fed mode or the fasting mode.

One means of achieving a swellable particle is to disperse the active ingredient in a solid matrix formed of a substance that absorbs the gastric fluid and swells as a result of the absorbed fluid. (See., e.g., U.S. Pat. Nos. 5,007,790, 5,582, 837, and 5,972,389, and WO 98/55107.)

Polymer matrices are useful for achieving controlled release of the active ingredient over a prolonged period of time. Such sustained or controlled release is achieved either by limiting the rate by which the surrounding gastric fluid can diffuse through the matrix and reach the active ingredient, dissolve the active ingredient and diffuse out again with the dissolved active ingredient, or by using a matrix that slowly erodes. (See, e.g., U.S. Pat. Nos. 4,915,952, 5,328,942, 5,451,409, 5,783,212, 5,945,125, 6,090,411, 6,120,803, 6,210,710, 6,217,903, and WO 96/26718 and WO 97/18814).

U.S. Pat. No. 4,434,153, describes the use of a hydrogel matrix that imbibes fluid to swell to reach a size encouraging prolonged gastric retention. This matrix surrounds a plurality of tiny pills consisting of active ingredient with a release rate controlling wall of fatty acid and wax surrounding each of the pills.

U.S. Pat. Nos. 5,007,790 and 5,582,837, and WO 93/18755, describe a swelling hydrogel polymer with active ingredient particles embedded within it. These particles dissolve once the hydrogel matrix is hydrated. The swollen matrix is of a size to encourage gastric retention but only dissolved active ingredient reaches the mucosa and this can be delivered in a sustained manner. Such a system thus does not insult the mucosa with solid particles of irritant active ingredient and is suitable for delivering active ingredient to the upper gastrointestinal tract. These systems only apply in case of active ingredients of limited water solubility.

Layered Gastroretentive Systems

The layered gastroretentive active ingredient delivery systems described in, e.g., U.S. Pat. No. 6,685,962, can be used in the sustained release delivery methods described herein. In general, such delivery systems have an active agent or drug associated with a matrix that is affixed or attached to a membrane. The membrane prevents evacuation from the stomach thereby allowing the active agent/matrix to be retained in the stomach for 3-24 hours.

The matrix/membrane system can be a multilayer system, including but not limited to a bilayer system. In addition, the matrix/membrane may be administered as a folded configuration within a capsule, including but not limited to a gelatin capsule.

The matrix of such delivery systems can be a single- or multi-layered and have a two- or three-dimensional geometric configuration. The matrix can comprise a polymer selected from a degradable polymer, including but not limited to a hydrophilic polymer which is not instantly soluble in gastric fluids, an enteric polymer substantially insoluble at pH less than 5.5, a hydrophobic polymer; or any mixture thereof. In addition, the matrix can comprise a non-degradable; or a mixture of at least one degradable polymer and at least one non-degradable polymer.

The hydrophilic polymers of such delivery systems may be any hydrophilic polymer, including but not limited to, a protein, a polysaccharide, a polyacrylate, a hydrogel or any derivative thereof. By way of example only, such proteins are proteins derived from connective tissues, such as gelatin and collagen, or an albumin such as serum albumin, milk albumin or soy albumin. By way of example only, such polysaccharides are sodium alginate or carboxymethylcellulose. By way of example only, other hydrophilic polymers may be polyvinyl alcohol, polyvinyl pyrrolidone or polyacrylates, such as polyhydroxyethylmethacrylate. In addition, the hydrophilic polymer may be cross-linked with a suitable cross-linking agent. Such cross-linking agents are well known in the art, and include, but are not limited to, aldehydes (e.g. formaldehyde and glutaraldehyde), alcohols, di-, tri- or tetravalent ions (e.g. aluminum, chromium, titanium or zirconium ions), acyl chlorides (e.g. sebacoyl chloride, tetraphthaloyl chloride) or any other suitable cross-linking agent, such as urea, bis-diazobenzidine, phenol-2,4-disulfonyl chloride, 1,5-difluoro-2,4-dinitrobenzene, 3,6-bis-(mercuromethyl)-dioxane urea, dimethyl adipimidate, N,N'-ethylene-bis-(iodoacetamide) or N-acetyl homocysteine thiolactone. Other suitable hydrogels and their suitable cross-linking agents are listed, for example, in the Handbook of Biodegradable Polymers [A. J. Domb, J. Kost & D. M. Weisman, Eds. (1997) Harwood Academic Publishers].

The enteric polymer used in such layered delivery systems is a polymer that is substantially insoluble in a pH of less than 5.5. By way of example only, such enteric polymers include shellac, cellulose acetate phthalate, hydroxypropyl methylcellulose phthalate, hydroxypropyl methylcellulose acetate succinate or methylmethacrylate-methacrylic acid copolymers.

The non-degradable hydrophobic polymers used in such layered delivery systems include, but are not limited to, ethylcellulose, acrylic acid-methacrylic acid esters copolymer, polyethylene, polyamide, polyvinylchloride, polyvinyl acetate and mixtures thereof.

The degradable hydrophobic polymers used in such layered delivery systems include, but are not limited to, poly (alpha-hydroxyacids), such as poly(lactic acid), poly(glycolic acid), copolymers and mixtures thereof.

The membranes used in such layered delivery systems have substantial mechanical strength and may be continuous or non-continuous. Such membranes may comprise, by way of example only, cellulose ethers and other cellulose derivatives such as cellulose nitrate, cellulose acetate, cellulose acetate butyrate or cellulose acetate propionate; polyesters, such as polyethylene terephthalate, polystyrene, including copolymers and blends of the same; polylactides, including copolymers thereof with p-dioxanone, polyglycolides, polylactidglycolides; polyolefins, including polyethylene, and polypropylene; fluoroplastics, such as polyvinylidene fluoride and polytetrafluoroethylene, including copolymers of the same with hexafluoropropylene or ethylene; polyvinylchloride, polyvinylidene chloride copolymers, ethylene vinyl alcohol copolymers, polyvinyl alcohols, ammonium-methacrylate copolymers and other polyacrylates and polymethacrylates; polyacrylonitriles; polyurethanes; polyphthalamides; polyamides; polyimides; polyamide-imides; polysulfones; polyether sulfones; polyethylene sulfides; polybutadiene; polymethyl pentene; polyphenylene oxide (which may be modified); polyetherimides; polyhydroxyalkanoates; tyrosine derived polyarylates and polycarbonates including polyester carbonates, polyanhydrides, polyphenylene ethers, polyalkenamers, acetal polymers, polyallyls, phenolic polymers, polymelamine formaldehydes, epoxy polymers, polyketones, polyvinyl acetates and polyvinyl carbazoles.

The active agent or compound associated with the matrix may be in a particulate form or may be in the form of raw powder, or soluted, dispersed or embedded in a suitable liquid, semisolid, micro- or nanoparticles, micro- or nanospheres, tablet, or capsule. The compound, or mixtures of compounds, in any of such forms, may be embedded in at least one layer of the matrix of the delivery system. Alternatively, in a multi-layered matrix, including but not limited to a bi-layered matrix, the active ingredient may be entrapped between any two layers, whether in free form or contained within a compound-containing means such as, by way of example only, in a tablet or a capsule.

Microcapsule Gastroretentive Systems

The microcapsules gastroretentive systems described in U.S. Pat. Nos. 6,022,562, 5,846,566 and 5,603,957, can be used in the sustained release delivery methods described herein. Microparticles of an active agent or drug are coated by spraying with a material consisting of a mixture of a film-forming polymer derivative, a hydrophobic plasticizer, a functional agent and a nitrogen-containing polymer. The resulting microcapsules are less than or equal to 1000 microns (μm) in size, and in certain cases such microcapsules are between 100 and 500 microns. These microcapsules remain in the small intestine for at least 5 hours.

Film-forming polymer derivatives used in such microcapsules include, but are not limited to, ethylcellulose, cellulose acetate, and non-hydrosoluble cellulose derivates. The nitrogen-containing polymers include, but are not limited to, polyacrylamide, poly-N-vinylamide, poly-N-vinyl-lactam and polyvinylpyrrolidone. The plasticizer used in such microcapsule include, but are not limited to, glycerol esters, phthalates, citrates, sebacates, cetylalcohol esters, castor oil and cutin. The surface-active and/or lubricating agent used in such microcapsule include, but are not limited to, anionic surfactants, such as by way of example the alkali metal or alkaline-earth metal salts of fatty acids, stearic acid and/or oleic acid, nonionic surfactants, such as by way of example, polyoxyethylenated esters of sorbitan and/or polyoxyethylenated esters of sorbitan and/or polyoxyethylenated derivatives of castor oil; and/or lubricants such as stearates, such as by way of example, calcium, magnesium, aluminum stearate, zinc stearate, stearylfumarate, sodium stearylfimarate, and glyceryl behenate.

In one non-limiting example, Chitosan and mixtures of chitosan with carboxymethylcellulose sodium (CMC—Na) have been used as vehicles for the sustained release of active ingredients, as described by Inouye et al., Drug Design and Delivery 1: 297-305, 1987. Mixtures of these compounds and agents of the combinations of the invention, when compressed under 200 kg/cm2, form a tablet from which the active agent is slowly released upon administration to a subject. The release profile can be changed by varying the ratios of chitosan, CMC—Na, and active agent(s). The tablets can also contain other additives, including lactose, CaHPO4 dihydrate, sucrose, crystalline cellulose, or croscarmellose sodium.

In another non-limiting example, Baichwal, in U.S. Pat. No. 6,245,356, describes sustained release oral, solid dosage forms that includes agglomerated particles of a therapeutically active medicament in amorphous form, a gelling agent, an ionizable gel strength enhancing agent and an inert diluent. The gelling agent can be a mixture of a xanthan gum and a locust bean gum capable of cross-linking with the xanthan gum when the gums are exposed to an environmental fluid. Preferably, the ionizable gel enhancing agent acts to enhance the strength of cross-linking between the xanthan gum and the locust bean gum and thereby prolonging the release of the medicament component of the formulation. In addition to xanthan gum and locust bean gum, acceptable gelling agents that may also be used include those gelling agents well known in the art. Examples include naturally occurring or modified naturally occurring gums such as alginates, carrageenan, pectin, guar gum, modified starch, hydroxypropylmethylcellulose, methylcellulose, and other cellulosic materials or polymers, such as, for example, sodium carboxymethylcellulose and hydroxypropyl cellulose, and mixtures of the foregoing.

In another non-limiting formulation useful for the combinations of the invention, Baichwal and Staniforth in U.S. Pat. No. 5,135,757 describe a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical-filler (such as, for example, lactose, dextrose, sucrose, sorbitol, xylitol, fructose or mixtures thereof). After mixing the excipient with a tricyclic compound/corticosteroid combination, or combination agent, of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

In another non-limiting example, Shell, in U.S. Pat. No. 5,007,790, describes sustained-release oral drug-dosage forms that release a active ingredient in solution at a rate controlled by the solubility of the active ingredient. The dosage form comprises a tablet or capsule that includes a plurality of particles of a dispersion of a limited solubility active ingredient in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve active ingredient and leach it from the particles, assuring that active ingredient reaches the stomach in the solution state which is less injurious to the stomach than solid-state active ingredient. The programmed eventual dissolution of the polymer depends upon the nature of the polymer and the degree of crosslinking The polymer is nonfibrillar and substantially water soluble in its uncrosslinked state, and the degree of crosslinking is sufficient to enable the polymer to remain insoluble for the desired time period, normally at least from about 4 hours to 8 hours up to 12 hours, with the choice depending upon the active ingredient incorporated and the medical treatment involved. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

In an additional non-limiting example, Silicone microspheres for pH-controlled gastrointestinal drug delivery have been described by Carelli et al., Int. J. Pharmaceutics 179: 73-83, 1999. The microspheres are pH-sensitive semi-interpenetrating polymer hydrogels made of varying proportions of poly(methacrylic acid-co-methylmethacrylate) (Eudragit L100 or Eudragit S100) and crosslinked polyethylene glycol 8000 that are encapsulated into silicone microspheres. Slow-release formulations can include a coating which is not readily water-soluble but which is slowly attacked and removed by water, or through which water can slowly permeate. Thus, for example, the combinations of the invention can be spray-coated with a solution of a binder under continuously fluidizing conditions, such as describe by Kitamori et al., U.S. Pat. No. 4,036,948. Examples of water-soluble binders include pregelatinized starch (e.g., pregelatinized corn starch, pregelatinized white potato starch), pregelatinized modified starch, water-soluble celluloses (e.g. hydroxypropyl-cellulose, hydroxymethyl-cellulose, hydroxypropylmethyl-cellulose, carboxymethyl-cellulose), polyvinylpyrrolidone, polyvinyl alcohol, dextrin, gum arabicum and gelatin, organic solvent-soluble binders, such as cellulose derivatives (e.g., cellulose acetate phthalate, hydroxypropylmethyl-cellulose phthalate, ethylcellulose).

Combinations of the invention, or a component thereof, with sustained release properties can also be formulated by spray drying techniques. Yet another form of sustained release combinations can be prepared by microencapsulation of combination agent particles in membranes which act as microdialysis cells. In such a formulation, gastric fluid permeates the microcapsule walls and swells the microcapsule, allowing the active agent(s) to dialyze out (see, for example, Tsuei et al., U.S. Pat. No. 5,589,194). One commercially available sustained-release system of this kind consists of microcapsules having membranes of acacia gum/gelatine/ethyl alcohol. This product is available from Eurand Limited (France) under the trade name Diffucaps™. Microcapsules so formulated can be carried in a conventional gelatine capsule or tabletted. A bilayer tablet can be formulated for a combination of the invention in which different custom granulations are made for each agent of the combination and the two agents are compressed on a bi-layer press to form a single tablet.

When desired, formulations can be prepared with enteric coatings adapted for sustained or controlled release administration of the active ingredient. A common type of controlled-release formulation that may be used for the purposes of the present invention comprises an inert core, such as a sugar sphere, coated with an inner active ingredient-containing layer and an outer membrane layer controlling active ingredient release from the inner layer. Other formulations for targeted release of compounds in the gastrointestinal tract are also known in the art and contemplated for use with the invention described herein. Exemplary systems for targeting delivery of a substance to the upper and/or lower gastrointestinal tract include the formulations of the TIMERx® system. This controlled release formulation system provides for altered temporal release (SyncroDose™) as well as biphasic release (Geminex®). (See, for example, Staniforth & Baichwal, TIMERx®: novel polysaccharide composites for controlled/programmed release of active ingredients in the gastrointestinal tract, Expert Opin. Drug Deliv., 2(3): 587-89 (2005)). Using formulations such as these for the invention described herein, compositions can be created which target the upper gastrointestinal tract, the lower gastrointestinal tract, or both, in addition to temporally controlling the release of such compounds in any of these locations.

One non-limiting example of a lower GI delivery formulation comprises a tablet for lower GI delivery. The inner composition of the tablet comprises about 0.01% weight to about 10.0% by weight of a suitable active ingredient; about 50% by weight to about 98% by weight of a hydrocolloid gum obtainable from higher plants; and about 2% by weight to about 50% by weight of a pharmaceutically acceptable excipient such as a binder. Other optional materials may be present that will assist in establishing the desired characteristics of the pharmaceutical composition. These include materials that may enhance absorption of the active ingredient in the lower GI, may protect the active ingredient against degradation, may prevent dissolution, and the like. Optionally surrounding the inner composition of the tablet is a coating that is preferably of enteric polymeric material.

The formulation is designed to take advantage of (1) the protective characteristics of the hydrocolloid obtainable from higher plants in the upper GI and (2) the disintegrative characteristics of the hydrocolloid in the lower GI. Thus, the inner composition of the tablet may be one of several designs: (a) it may be a matrix of a therapeutically effective amount of the active ingredient uniformly dispersed throughout in combination with a high percentage of the hydrocolloid and a generally lesser amount of other excipients; (b) it may have a core, in which the active ingredient is concentrated, surrounded by a layer of material that is free of the active ingredient and that has a high percentage of the hydrocolloid and a generally lesser amount of other excipients; (c) it may have a concentration gradient of the active ingredient such that there is a greater amount in the core of the tablet with lesser amounts in multiple layers surrounding the core and very little or no active ingredient in the outer layer. Whether the design of the tablet is that of (a), (b) or (c) above, the specificity for regional delivery to the lower GI is enhanced by enterically coating the tablet with an appropriate enteric coating material.

Hydrocolloids are obtainable from higher plants. By "higher plant" is meant an organism of the vegetable kingdom that lacks the power of locomotion, has cellulose cell walls, grows by synthesis of inorganic substances and includes the vascular plants (or tracheophytes) of the division Spermatophyta, particularly those of the class Angiospermae. The gums may be extracted from the roots, legumes, pods, berries, bark, etc. Representative hydrocolloid gums obtainable from higher plants include guar gum, gum tragacanth, karaya gum (also referred to as kadaya gum) and locust bean gum (also referred to as carob). Others may be readily apparent to one of skill in the art. See, for example, "The Chemistry of Plant Gums and Mucilages" by Smith and Montgomery from ACS Monograph Series, No. 141, 1959, Reinhold Publishing Company and the 18th edition of the Merck Index. A particularly convenient and useful hydrocolloid is guar gum which is a neutral polysaccharide and consists of long galactomannan molecules with some side chain attachments. The hydrocolloids used in the subject invention generally have high viscosity exhibited upon hydration, are normally linear (at least about 50% by weight of the compound is the backbone chain), and will normally have high molecular weight, usually about $3 \times 10^5$ daltons, more usually greater than about $1 \times 10^6$ daltons. Generally, the hydrocolloid comes as a powdered hydrocolloid gum and exhibits a viscosity at a 1% concentration in a neutral aqueous solution of at least about 75 centipoise per second (cps) at 25° C. after 24 hours, using a Brookfield viscometer (model LDF) with a number 3 spindle at 90 rpms, preferably at least $1 \times 10^3$ cps and most preferably at least about $2 \times 10^3$ cps. Generally, the viscosity increases with increasing molecular weight. See Meer Corporation, "An Introduction to Polyhydrocolloids." Hydrocolloid gums most useful are those where the hydrocolloid is a polysaccharide hydrocolloid which is chemically designated as galactomannan. Galactomannans are polysaccharides consisting of long chains of $(1 \rightarrow 4)$-$\beta$-D-mannopyranosyl units to which single unit side chains of $\alpha$-D-galactopyranosyl are joined by $(1 \rightarrow 6)$ linkages. Galactomannans are found in a variety of plants but differ in molecular size and the number of D-galactosyl side chains. The galactomannans useful in this invention are commonly found in the endosperms of the leguminosae.

Galactomannan can be obtained, for example, from the cyamopsis tetragonolobus, commonly referred to as guar. This exhibits a percentage mannose residue of about 64% with a percent galactose residue of about 36%. Commercially available guar gum is about 66-82% galactomannan polysaccharide with impurities making up the remainder of the composition. According to the National Formulary (NF) standards the guar gum may contain up to 15% w water, up to 10% w protein, up to 7% w acid insoluble material and up to about 1.5% ash. Sources of commercially available guar gum are Aqualon Company, Wilmington, Del.; Meer Corporation, Cincinnati, Ohio; Stein Hall & Company and TIC Gums, Inc., Belcamp, Md.

Other hydrocolloids are known in the art. See for example "The Chemistry of Plant Gums and Mucilages" by Smith and Montgomery from the A.C.S. Monograph series, #141, 1959, Reinhold Publishing Co. and the Eighteenth Edition of The Merck Index. In general, the amount of the hydrocolloid that will be used is an amount that allows the composition to traverse the upper GI tract without significant disintegration and without releasing significant amounts of active ingredient in the upper GI tract, i.e. to provide a delayed-release profile. Generally, that amount of hydrocolloid will be more than about 50% but less than about 98%. Depending on individual variability, whether a subject has eaten or has fasted, and other factors, a tablet will traverse the stomach and upper intestinal tract in about 3 to 6 hours. During this time, little active ingredient (less than 20%, preferably less than 10%) is released from the tablet of this invention. Once the tablet reaches the lower GI, the release of the active ingredient is triggered by enzymatic degradation of the galactomannan gum.

One non-limiting example of a formulation for upper gastrointestinal delivery comprises a free-flowing slow release granulation for use as a pharmaceutical excipient that includes from about 20 to about 70 percent or more by weight of a hydrophilic material that includes a heteropolysaccharide (such as, for example, xanthan gum or a derivative thereof) and a polysaccharide material capable of cross-linking the heteropolysaccharide (such as, for example, galactomannans, and most preferably locust bean gum) in the presence of aqueous solutions, and from about 30 to about 80 percent by weight of an inert pharmaceutical-filler (such as, for example, lactose, dextrose, sucrose, sorbitol, xylitol, fructose or mixtures thereof). After mixing the excipient with the compounds of the invention, the mixture is directly compressed into solid dosage forms such as tablets. The tablets thus formed slowly release the medicament when ingested and exposed to gastric fluids. By varying the amount of excipient relative to the medicament, a slow release profile can be attained.

One non-limiting example of a sustained gastrointestinal delivery formulation comprises a plurality of particles of a dispersion of a limited solubility active ingredient in a hydrophilic, water-swellable, crosslinked polymer that maintains its physical integrity over the dosing lifetime but thereafter rapidly dissolves. Once ingested, the particles swell to promote gastric retention and permit the gastric fluid to penetrate the particles, dissolve active ingredient and leach it from the particles, assuring that active ingredient reaches the stomach in the solution state which is less injurious to the stomach than solid-state active ingredient. The programmed eventual dissolution of the polymer depends upon the nature of the polymer and the degree of crosslinking. The polymer is nonfibrillar and substantially water soluble in its uncrosslinked state, and the degree of crosslinking is sufficient to enable the polymer to remain insoluble for the desired time period. Examples of suitable crosslinked polymers that may be used in the invention are gelatin, albumin, sodium alginate, carboxymethyl cellulose, polyvinyl alcohol, and chitin. Depending upon the polymer, crosslinking may be achieved by thermal or radiation treatment or through the use of crosslinking agents such as aldehydes, polyamino acids, metal ions and the like.

Formulations for upper intestinal delivery, lower intestinal delivery or both are known in the art. Targeting of active ingredients to various regions of the gut is described, e.g., in *The Encyclopedia of Pharmaceutical Technology*, by James Swarbrick and James Boylan, Informa Health Care, 1999, at pp. 287-308. Any suitable formulation for gastrointestinal delivery for site-specific delivery and/or specific temporal delivery (i.e. delayed, controlled, extended, or sustained release) can be used with the invention and is contemplated herein. In one non-limiting example, a single composition comprises a first formulation for delivery of at least one chemosensory receptor ligand to the upper gastrointestinal tract and a second formulation for delivery of at least one chemosensory receptor ligand to the lower gastrointestinal tract. Thus, a single composition can provide for delivery of chemosensory receptor ligands to the upper and lower gastrointestinal tract. Additional non-limiting examples include compositions having formulations for delivery of at least one chemosensory receptor ligand to the upper gastrointestinal tract and compositions having formulations for delivery of at least one chemosensory receptor ligand to the lower gastrointestinal tract. As described herein, different combinations of chemosensory receptor ligands can be formulated for treatment of specific conditions and for delivery to specific locations in the intestinal tract.

Any of the delivery systems described herein may be used in combination with others to achieve multiple releases and/or specific release profiles. In some embodiments, the active agent(s) is in a formulation that achieves multiple releases in the gastrointestinal locations following administration. In certain embodiments, the active agent(s) is in a multiple release formulation that releases at an onset of about 10 minutes, about 30 minutes, about 120 minutes, about 180 minutes, about 240 minutes, or combinations thereof following administration. In certain embodiments, the active agent(s) is in a multiple release formulation that releases at an onset of about 5 to about 45 minutes, about 105 to about 135 minutes, about 165 to about 195 minutes, about 225 to about 255 minutes, or combinations thereof following administration. In other embodiments, the active agent(s) is in a multiple release formulation that releases in the duodenum, jejunum, ileum, lower intestine or combinations thereof following administration. In yet other embodiments, the active agent(s) is in a multiple release formulation that releases at an onset of about pH 5.5, about pH 6.0, at about pH 6.5, about pH 7.0, or combinations thereof following administration. In yet other embodiments, the active agent(s) is in a multiple release formulation that releases in ranges at about pH 5.0 to about pH 6.0, about pH 6.0 to about pH 7.0, about pH 7.0 to about pH 8.0, or combinations thereof following administration. In yet other embodiments, the active agent(s) is in a multiple release formulation that releases a fraction or portion of the active agent(s) as an immediate release with the rest of the active agent(s) released by a modified manner described herein.

Excipients

Any of the compositions or formulations described herein include any commonly used excipients in pharmaceutics and are selected on the basis of compatibility with the active agent(s) and release profile properties of the desired dosage form. Excipients include, but are not limited to, binders, fillers, flow aids/glidents, disintegrants, lubricants, stabilizers, surfactants, and the like. A summary of excipients described herein, may be found, for example in *Remington: The Science and Practice of Pharmacy*, Nineteeth Ed (Easton, Pa.: Mack Publishing Company, 1995); Hoover, John E., *Remington's Pharmaceutical Sciences*, (Easton, Pa.: Mack Publishing Co 1975); Liberman, H. A. and Lachman, L., Eds., *Pharmaceutical Dosage Forms* (New York, N.Y.: Marcel Decker 1980); and *Pharmaceutical Dosage Forms and Drug Delivery Systems*, Seventh Ed (Lippincott Williams & Wilkins 1999), herein incorporated by reference in their entirety.

Binders impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®);

microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

Disintegrants facilitate breakup or disintegration of oral solid dosage forms after administration. Examples of disintegrants include a starch, e.g., a natural starch such as corn starch or potato starch, a pregelatinized starch such as National 1551 or Amijel®, or sodium starch glycolate such as Promogel® or Explotab®; a cellulose such as a wood product, methylcrystalline cellulose, e.g., Avice10, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a resin such as a cation-exchange resin; citrus pulp; sodium lauryl sulfate; sodium lauryl sulfate in combination starch; and the like.

Lubricants are compounds which prevent, reduce or inhibit adhesion or friction of materials. Exemplary lubricants include, e.g., stearic acid; calcium hydroxide; talc; sodium stearyl fumerate; a hydrocarbon such as mineral oil, hydrogenated castor oil or hydrogenated vegetable oil such as hydrogenated soybean oil (Sterotex®); higher fatty acids and their alkali-metal and alkaline earth metal salts, such as aluminum, calcium, magnesium, zinc; stearic acid, sodium stearates, magnesium stearates, glycerol, talc, waxes, Stearowet® boric acid, sodium benzoate, sodium acetate, sodium chloride, leucine, a polyethylene glycol or a methoxypolyethylene glycol such as Carbowax™, ethylene oxide polymers, sodium oleate, glyceryl behenate (E.g. Compritol 888 Ato), glyceryl disterate (Precirol Ato 5), polyethylene glycol, magnesium or sodium lauryl sulfate, colloidal silica such as Syloid™, Carb-O-Sil®, DL-leucine, a starch such as corn starch, silicone oil, a surfactant, and the like.

Flow-aids or glidants improve the flow characteristics of powder mixtures. Such compounds include, e.g., colloidal silicon dioxide such as Cab-o-Sil®; tribasic calcium phosphate, talc, corn starch, DL-leucine, sodium lauryl sulfate, magnesium stearate, calcium stearate, sodium stearate, kaolin, and micronized amorphous silicon dioxide (Syloid®) and the like.

Plasticizers aid in coating of oral solid dosage forms. Exemplary plasticizers include, but are not limited to, triethyl citrate, triacetin (glyceryl triacetate), acetyl triethyl citrate, polyethylene glycols (PEG 4000, PEG 6000, PEG 8000), Carbowax 400 (polyethylene glycol 400), diethyl phthalate, diethyl sebacate, acetyltriethylcitrate, oleic acid, glyceralmonosterate, tributyl citrate, acetylated monoglycerides, glycerol, fatty acid esters, propylene glycol, and dibutyl phthalate and the like.

The aforementioned excipients are given as examples only and are not meant to include all possible choices. Other suitable excipient classes include coloring agents, granulating agents, preservatives, anti-foaming agents, solubulizers and the like. Additionally, many excipients can have more than one role or function, or can be classified in more than one group; the classifications are descriptive only, and are not intended to limit any use of a particular excipient.

Methods for Evaluating Treatment
Hormonal Profiles

Administration of chemosensory receptor ligand compositions provided herein modulate hormone levels and/or concentrations including, but not limited to, GLP-1, GLP-2, GIP, oxyntomodulin, PYY, cholecystokinin (CCK), glycentin, insulin, glucagon, ghrelin, amylin, insulin and insulin C peptide. Sampling of hormones can be performed frequently during the administration of ligands. Test animals and subjects can be studied with and without systemic inhibition of dipeptidyl-peptidase IV (DPP-IV) to augment the circulating half-life of the relevant hormones that can be degraded by DPP-IV.

For glucose lowering, hormonal profiles suited for treating elevated blood glucose are composed of, e.g., 1) GLP-1 with circulating concentrations over 1.5-fold or over 3-fold basal concentrations; 3) GIP with circulating concentrations over 1.5-fold basal concentrations and 3) PYY 3-36 circulating concentrations over 1.5-fold or over 2-fold basal concentrations.

For weight loss, hormonal profiles suited for treating elevated blood glucose are composed of, e.g., 1) PYY with circulating concentrations over 3-fold basal concentrations; 2) Oxyntomodulin with circulating concentrations over 2-fold basal concentrations; 3) GPL-1 with circulating concentrations over 3-fold basal concentrations; and 4) CCK with circulating concentrations over 2-fold basal concentrations.

In some embodiments, administration of chemosensory receptor ligand compositions as provided herein modulate circulating concentrations of at least one, at least two, at least three, at least four, at least five, at least six, at least seven and at least eight hormones. In certain embodiments, administration of chemosensory receptor ligand compositions as provided herein increase circulating concentrations of at least one, at least two, at least three, at least four, at least five, at least six, at least seven and at least eight hormones. In other embodiments, administration of chemosensory receptor ligand compositions as provided herein decrease circulating concentrations of at least one, at least two, at least three, at least four, at least five, at least six, at least seven and at least eight hormones. In some embodiments, administration of chemosensory receptor ligand compositions modulates GLP-1. In some embodiments, administration of chemosensory receptor ligand compositions modulates GLP-2. In some embodiments, administration of chemosensory receptor ligand compositions modulates GIP. In some embodiments, administration of chemosensory receptor ligand compositions modulates oxyntomodulin. In some embodiments, administration of chemosensory receptor ligand compositions modulates PYY. In some embodiments, administration of chemosensory receptor ligand compositions modulates CCK. In some embodiments, administration of chemosensory receptor ligand compositions modulates glycentin. In some embodiments, administration of chemosensory receptor ligand compositions modulates insulin. In some embodiments, administration of chemosensory receptor ligand compositions modulates glucagon. In some embodiments, administration of chemosensory receptor ligand compositions modulates, ghrelin. In some embodiments, administration of chemosensory receptor ligand compositions modulates amylin. In some embodiments, administration of chemosensory receptor ligand compositions modulates insulin. In some embodiments, administration of chemosensory receptor ligand compositions modulates insulin C peptide.

Hormone Assays

In embodiments, the levels of hormones assayed in association with the methods of the invention, including, but not limited to, GLP-1, GLP-2, GIP, oxyntomodulin, PYY, CCK, glycentin, insulin, glucagon, ghrelin, amylin, insulin, insulin C peptide and/or combinations thereof are detected according to standard methods described in the literature. For example, proteins can be measured by immunological assays, and transcription products by nucleic acid amplification techniques. Functional assays described in the art can also be used as appropriate. In embodiments, samples assayed comprise cultured cells, patient cell or tissue samples, patient body fluids, e.g., blood or plasma, etc.

For example, immunofluorescence can be used to assay for GLP-1. Cells can be grown on matrigel-coated cover slips to confluent monolayers in 12-well plates at 37° C., fixed in 4% paraformaldehyde in phosphate-buffered saline (PBS) and incubated with primary antiserum (e.g., rabbit anti-alpha gustducin, 1:150; Santa Cruz Biotechnology, and rabbit anti-GLP-1, Phoenix) overnight at 4° C. following permeabilization with 0.4% Triton-X in PBS for 10 minutes and blocking for 1 hour at room temperature. Following three washing steps with blocking buffer, the appropriate secondary antibody is applied (AlexaFluor 488 anti-rabbit immunoglobulin, 1:1000; Molecular Probes) for 1 hour at room temperature. After three washing steps, the cells can be fixed in Vectashield medium and the immunofluorescence visualized.

GLP-1 RNA isolated from cells can be assayed using RT-PCR. RT-PCR RNA isolation from cells can be performed using standard methodology. The RT-PCR reaction can be performed in a volume of 50 µl in a Peltier thermal cycler (PTC-225 DNA Engine Tetrad Cycler; MJ Research), using published primer sequences (Integrated DNA Technologies). Reverse transcription can be performed at 50° C. for 30 minutes; after an initial activation step at 95° C. for 15 minutes. PCR can be performed by denaturing at 94° C. for 1 minute, annealing at 55° C. for 1 minute and extension at 72° C. for 1 minute for 40 cycles, followed by a final extension step at 72° C. for 10 minutes. Negative controls can be included as appropriate, for example, by substituting water for the omitted reverse transcriptase or template. The control can be RNA isolated from, e.g., rat lingual epithelium. PCR products can be separated in 2% agarose gel with ethidium bromide, and visualized under UV light.

Radioimmunoassay (RIA) for total GLP-1 in patient blood samples can be performed as described in the art, e.g., by Laferrere, et al., 2007, "Incretin Levels and Effect are Markedly Enhanced 1 Month after Roux-en-Y Gastric Bypass Surgery in Obese Patients with Type 2 Diabetes, Diabetes Care 30(7):1709-1716 (using commercially available materials obtained from Phoenix Pharmaceutical, Belmont, Calif.). The authors describe measuring the effect of GIP and GLP-1 on secretion of insulin by measuring the difference in insulin secretion (area under the curve, or AUC) in response to an oral glucose tolerance test and to an isoglycemic intravenous glucose test.

Measurement of plasma concentrations of GLP-1, GIP, glucagon, insulin, C peptide, pancreatic peptide, nonesterified fatty acids, glutamic acid decarboxylase antibodies, and islet antigen antibodies, is described, e.g., by Toft-Nielsen, et al., 2001, "Determinants of the Impaired Secretion of Glucagon-Like Peptide-1 in Type 2 Diabetic Patients," J. Clin. End. Met. 86(8):3717-3723. The authors describe the use of radio-immunoassay for GLP-1 to measure plasma concentrations of amidated GLP-1-(7-36), using antibody code no. 89390. This assay measures the sum of GLP-1-(7-36) and its metabolite GLP-1-(9-36). The authors describe measurement of GIP using C-terminally directed antibody code no. R65 (RIA), that reacts 100% with a human GIP but not with 8-kDA GIP.

GLP-1 and PYY can be directly assayed in the supernatant from venous effluents as described by, e.g., Claustre, et al. (1999, "Stimulatory effect of β-adrenergic agonists on ileal L cell secretion and modulation by α-adrenergic activation, J. Endocrin. 162:271-8). (See also Plaisancié et al., 1994, "Regulation of glucagon-like peptide-1-(7-36) amide secretion by intestinal neurotransmitters and hormones in the isolated vascularly perfused rat colon," Endocrinology 135: 2398-2403 and Plaisancié et al., 1995, "Release of peptide YY by neurotransmitters and gut hormones in the isolated, vascularly perfused rat colon," Scandinavian Journal of Gastroenterology 30:568-574.) In this method, the 199D anti-GLP-1 antibody is used at a 1:250 000 dilution. This antibody reacts 100% with GLP-1-(7-36) amide, 84% with GLP-1-(1-36) amide, and less than 0.1% with GLP-1-(1-37), GLP-1-(7-37), GLP-2, and glucagon. PYY is assayed with the A4D anti-porcine PYY antiserum at a 1:800 000 dilution.

Methods for assaying GLP-1 and GIP are also described elsewhere in the art, e.g., by Jang, et al., PNAS, 2007.

PYY can also be assayed in blood using a radioimmunoassay as described by, e.g., Weickert, et al., 2006, "Soy isoflavones increase preprandial peptide YY (PYY), but have no effect on ghrelin and body weight in healthy postmenopausal women" Journal of Negative Results in BioMedicine, 5:11. Blood is collected in ice-chilled EDTA tubes for the analysis of glucose, ghrelin, and PYY. Following centrifugation at 1600 g for 10 minutes at 4° C., aliquots were immediately frozen at −20° C. until assayed. All samples from individual subjects were measured in the same assay. The authors described measuring immunoreactive total ghrelin was measured by a commercially available radioimmunoassay (Phoenix Pharmaceuticals, Mountain View, Calif., USA). (See also Weickert, et al., 2006, "Cereal fiber improves whole-body insulin sensitivity in overweight and obese women," Diabetes Care 29:775-780). Immunoreactive total human PYY is measured by a commercially available radioimmunoassay (LINCO Research, Missouri, USA), using $^{125}$I-labeled bioactive PYY as tracer and a PYY antiserum to determine the level of active PYY by the double antibody/PEG technique. The PYY antibody is raised in guinea pigs and recognizes both the PYY 1-36 and PYY 3-36 (active) forms of human PYY.

SGLT-1, the intestinal sodium-dependent glucose transporter 1, is a protein involved in providing glucose to the body. It has been reported to be expressed in response to sugar in the lumen of the gut, through a pathway involving T1R3 (Margolskee, et al., 2007 "T1R3 and gustducin in gut sense sugars to regulate expression of Na+-glucose cotransporter 1," Proc Natl Acad Sci USA 104, 15075-15080"). Expression of SGLT-1 can be detected as described, e.g., by Margolskee, et al., for example, using quantitative PCR and Western Blotting methods known in the art. Measurement of glucose transport has been described in the literature, e.g., by Dyer, et al., 1997, Gut 41:56-9 and Dyer, et al., 2003, Eur. J. Biochem 270:3377-88. Measurement of glucose transport in brush border membrane vesicles can be made, e.g., by initiating D-glucose uptake by the addition of 100 µl of incubation medium containing 100 mM NaSCN (or KSCN), 100 mM mannitol, 20 mM Hepes/Tris (pH 7.4), 0.1 mM MgSO4, 0.02% (wt/vol) NaN3, and 0.1 mM D-[U$^{14}$C]glucose to BBMV (100 µg of protein). The reaction is stopped after 3 sec by addition of 1 ml of ice-cold stop buffer, containing 150 mM KSCN, 20 mM Hepes/Tris (pH 7.4), 0.1 mM MgSO4, 0.02% (wt/vol) NaN3, and 0.1 mM phlorizin. A 0.9-ml portion of the reaction mixture is removed and filtered under vacuum through a 0.22-μm pore cellulose acetate/nitrate filter (GSTF02500; Millipore, Bedford, Mass.). The filter is washed five times with 1 ml of stop buffer, and the radioactivity retained on the filter is measured by liquid scintillation counting.

Evaluation of Treatment of Diabetes

The effect of a chemosensory receptor ligand treatment of the invention on aspects of diabetic disease can be evaluated according to methods known in the art and common practiced by physicians treating diabetic subjects.

Efficacy of treatment of diabetes/metabolic syndrome and diabetes-associated conditions with the compositions and methods described herein can be assessed using assays and methodologies known in the art. By way of example, quantitative assessment of renal function and parameters of renal dysfunction are well known in the art. Examples of assays for the determination of renal function/dysfunction include serum creatinine level; creatinine clearance rate; cystatin C clearance rate, 24-hour urinary creatinine clearance, 24-hour urinary protein secretion; Glomerular filtration rate (GFR); urinary albumin creatinine ratio (ACR); albumin excretion rate (AER); and renal biopsy.

Quantitative assessment of pancreatic function and parameters of pancreatic dysfunction or insufficiency are also well known in the art. Examples of assays for the determination of pancreas function/dysfunction include evaluating pancreatic functions using biological and/or physiological parameters such as assessment of islets of Langerhans size, growth and/or secreting activity, beta-cells size, growth and/or secreting activity, insulin secretion and circulating blood levels, glucose blood levels, imaging of the pancreas, and pancreas biopsy, glucose uptake studies by oral glucose challenge, assessment of cytokine profiles, blood-gas analysis, extent of blood-perfusion of tissues, and angiogenesis within tissues.

Additional assays for treatment of diabetes and diabetes-associated conditions are known in the art and are contemplated herein.

Evaluation of Treatment of Obesity and Eating Disorders

In treatment of obesity it is desired that weight and/or fat is reduced in a subject. By reducing weight it is meant that the subject loses a portion of his/her total body weight over the course of treatment (whether the course of treatment be days, weeks, months or years). Alternatively, reducing weight can be defined as a decrease in proportion of fat mass to lean mass (in other words, the subject has lost fat mass, but maintained or gained lean mass, without necessarily a corresponding loss in total body weight). An effective amount of a chemosensory receptor ligand treatment administered in this embodiment is an amount effective to reduce a subject's body weight over the course of the treatment, or alternatively an amount effective to reduce the subject's percentage of fat mass over the course of the treatment. In certain embodiments, the subject's body weight is reduced, over the course of treatment, by at least about 1%, by at least about 5%, by at least about 10%, by at least about 15%, or by at least about 20%. Alternatively, the subject's percentage of fat mass is reduced, over the course of treatment, by at least 1%, at least 5%, at least 10%, at least 15%, at least 20%, or at least 25%.

Total body weight and fat content can be measured at the end of the dietary period. In rats, a frequently used method to determine total body fat is to surgically remove and weigh the retroperitoneal fat pad, a body of fat located in the retroperitoneum, the area between the posterior abdominal wall and the posterior parietal peritoneum. The pad weight is considered to be directly related to percent body fat of the animal. Since the relationship between body weight and body fat in rats is linear, obese animals have a correspondingly higher percent of body fat and retroperitoneal fat pad weight.

In embodiments wherein methods of treating, reducing, or preventing food cravings in a subject are provided, food cravings can be measured by using a questionnaire, whether known in the art or created by the person studying the food cravings. Such a questionnaire would preferably rank the level of food cravings on a numerical scale, with the subject marking 0 if they have no food cravings, and marking (if on a scale of 1-10) 10 if the subject has severe food cravings. The questionnaire would preferably also include questions as to what types of food the subject is craving. Binge eating can be determined or measured using a questionnaire and a Binge Eating Scale (BES). Binge eating severity can be divided into three categories (mild, moderate, and severe) based on the total BES score (calculated by summing the scores for each individual item). Accordingly, methods are provided for reducing the BES score of a subject comprising administering to a subject in need thereof a chemosensory receptor ligand treatment in an amount effective to reduce the BES score of the subject. In some embodiments, administration of a chemosensory receptor ligand treatment changes the BES category of the subject, for example, from severe to moderate, from severe to mild, or from moderate to mild.

Pre-treatment Evaluation of Patient Hormonal Profile

In some embodiments, patients are pre-evaluated for expression of metabolic hormones using methods described herein. The therapy provided to the individual can thus be targeted to his or her specific needs. In embodiments, a patient's hormonal profile is pre-evaluated and depending on the changes that the physician desires to affect, a certain chemosensory receptor ligand/metabolite combination is administered. The evaluation process can be repeated and the treatment adjusted accordingly at any time during or following treatment.

Definitions

"Chemosensory receptor" as used herein includes, e.g., the G-protein coupled receptors (GPCRs) that are expressed in the gastrointestinal tract of a subject. Chemosensory receptors include the taste receptor family and are further categorized according to their taste characteristics. They include sweet receptors, umami receptors (also known as savory receptors), bitter receptors, fat receptors, bile acid receptors, salty receptors, and sour receptors. A chemosensory receptor can be any receptor associated with chemosensory sensation or chemosensory ligand triggered signal transduction, e.g., via taste receptors or taste related receptors present in taste bud, gastrointestinal tract, etc.

Exemplary chemosensory receptors include T1R' s (e.g., T1R1, T1R2, T1R3), T2R' s, fat receptors, bile acid receptors, sweet receptors, salty receptors, variants, alleles, mutants, orthologs and chimeras thereof which specifically bind and/or respond to sweet, umami, bitter, bile acid, sour, salty, fat, or any other chemosensory related ligands including activators, inhibitors and enhancers. Chemosensory receptors also include taste receptors expressed in humans or other mammals (interspecies homologs), e.g., cells associated with taste and/or part of gastrointestinal system including without any limitation, esophagus, stomach, intestine (small and large), colon, liver, biliary tract, pancreas, gallbladder, etc. Also, T1R polypeptides include chimeric sequences derived from portions of a particular T1R polypeptide such as T1R1, T1R2 or T1R3 of different species or by combining portions of different T1Rs wherein such chimeric T1R sequences are combined to produce a functional sweet or umami taste receptor. For example, chimeric T1Rs may comprise the extracellular region of one T1R, i.e., T1R1 or T1R2 and the transmembrane region of another T1R, either T1R1 or T1R2.

Topologically, certain chemosensory GPCRs have an "N-terminal domain;" "extracellular domains," a "transmembrane domain" comprising seven transmembrane regions, and corresponding cytoplasmic and extracellular loops, "cytoplasmic regions," and a "C-terminal region" (see, e.g., Hoon et al., Cell 96:541-51 (1999); Buck et al., Cell 65:175-87 (1991)). These regions can be structurally identified using methods known to those of skill in the art, such as sequence analysis programs that identify hydrophobic and hydrophilic domains (see, e.g., Stryer, Biochemistry, (3rd ed. 1988); see also any of a number of Internet based sequence analysis programs, such as those found at dot.imgen.bcm.tmc.edu). These regions are useful for making chimeric proteins and for in vitro assays of the invention, e.g., ligand binding assays.

"Extracellular domains" therefore refers to the domains of chemosensory receptors, e.g., T1R polypeptides that protrude from the cellular membrane and are exposed to the extracellular face of the cell. Such regions would include the "N-terminal domain" that is exposed to the extracellular face of the cell, as well as the extracellular loops of the transmembrane domain that are exposed to the extracellular face of the cell, i.e., the extracellular loops between transmembrane regions 2 and 3, transmembrane regions 4 and 5, and transmembrane regions 6 and 7. The "N-terminal domain" starts at the N-terminus and extends to a region close to the start of the transmembrane region. These extracellular regions are useful for in vitro ligand binding assays, both soluble and solid phase. In addition, transmembrane regions, described below, can also be involved in ligand binding, either in combination with the extracellular region or alone, and are therefore also useful for in vitro ligand binding assays.

"Transmembrane domain," which comprises the seven transmembrane "regions," refers to the domains of certain chemosensory receptors, e.g., T1R or T2R polypeptides that lie within the plasma membrane, and may also include the corresponding cytoplasmic (intracellular) and extracellular loops, also referred to as transmembrane "regions."

"Cytoplasmic domains" refers to the domains of chemosensory receptors, e.g., T1R or T2R proteins that face the inside of the cell, e.g., the "C-terminal domain" and the intracellular loops of the transmembrane domain, e.g., the intracellular loops between transmembrane regions 1 and 2, transmembrane regions 3 and 4, and transmembrane regions 5 and 6. "C-terminal domain" refers to the region that spans from the end of the last transmembrane region to the C-terminus of the protein, and which is normally located within the cytoplasm.

The term "7-transmembrane receptor" includes polypeptides belonging to a superfamily of transmembrane proteins that have seven regions that span the plasma membrane seven times (thus, the seven regions are called "transmembrane" or "TM" domains TM I to TM VII).

The terms "gastrointestinal tract" "and "gut," as used herein, refer to the stomach and intestine. The "small" or "upper" intestine includes the duodenum, jejunum and ileum and the "large" or "lower" intestine includes the caecum, colon and rectum.

"Activity," or "functional effects" in the context of the disclosed ligands and assays for testing compounds that modulate a chemosensory receptor, e.g., enhance a chemosensory receptor family member mediated signal transduction such as sweet, umami, bitter, fat, bile acid, sour or salty receptor functional effects or activity, includes the determination of any parameter that is indirectly or directly under the influence of the particular chemosensory receptor. It includes, without any limitation, ligand binding, changes in ion flux, membrane potential, current flow, transcription, G protein binding, GPCR phosphorylation or dephosphorylation, signal transduction, receptor-ligand interactions, second messenger concentrations (e.g., cAMP, cGMP, IP3, or intracellular $Ca^{2+}$), in vitro, in vivo, and ex vivo and also includes other physiologic effects such as increases or decreases of neurotransmitter or hormone release and the measurement of the downstream physiological effects of such release.

The term "determining the functional effect" or receptor "activity" means assays for a compound that increases or decreases a parameter that is indirectly or directly under the influence of a chemosensory receptor, e.g., functional, physical and chemical effects. Such parameters also include secretion of hormones such as GIP, GLP-1, GLP-2, oxyntomodulin, insulin, glucagon, insulin peptide C, peptide YY, and CCK. Such functional effects can be measured by any means known to those skilled in the art, e.g., changes in spectroscopic characteristics (e.g., fluorescence, absorbance, refractive index), hydrodynamic (e.g., shape), chromatographic, or solubility properties, patch clamping, voltage-sensitive dyes, whole cell currents, radioisotope efflux, inducible markers, oocyte chemosensory receptor, e.g., T1R gene expression; tissue culture cell chemosensory receptor, e.g., T1R expression; transcriptional activation of chemosensory receptor, e.g., T1R genes; ligand binding assays; voltage, membrane potential and conductance changes; ion flux assays; changes in intracellular second messengers such as cAMP, cGMP, and inositol triphosphate (IP3); changes in intracellular calcium levels; neurotransmitter release, and the like. Also included are assays to determine increases or decreases in hormone or neurotransmitter secretion and/or activity. Changes in hormone or neurotransmitter secretion and/or activity can also be determined indirectly by the physiological effects caused by changes in the secretion of hormone or neurotransmitter. Functional and physical parameters that can be used to determine the functional effect or receptor activity include, but is not limited to, appetite suppression and weight loss.

Chemosensory receptor ligands include metabolized chemosensory receptor ligands that can be metabolized as an energy source, e.g. food or metabolites, as well as nonmetabolized chemosensory receptor ligands that are not metabolized as an energy source, e.g. tastants. The term nonmetabolized chemosensory receptor ligands, as used herein, includes chemosensory receptor ligands that are metabolized to a small degree but are not metabolized substantially. That is, nonmetabolized chemosensory receptor ligand includes ligands that have insignificant caloric value. Chemosensory receptor ligands include agonists, antagonists, modifiers, and enhancers as well as other compounds that modulate chemosensory receptors. Many chemosensory receptor ligands are known in the art and have been reported in the literature.

"Tastants" as used herein refers to any ligand that induces a flavor or taste in a subject, including sweet, sour, salty, bitter, umami and others. Tastants are also generally nonmetabolized in the sense that they have no significant caloric value.

"Metabolites" as used herein are metabolized chemosensory receptor ligands such as, for example, glucose, glutamate salts, fatty acids and bile acids. In certain aspects, metabolites can be derived from a food source. Metabolites can be administered as part of a chemosensory receptor ligand composition or separately.

Antagonists/inhibitors are compounds that, e.g., bind to, partially or totally block stimulation, decrease, prevent, delay activation, inactivate, desensitize, or down-regulate chemosensory receptor and/or taste transduction. Agonists/activators are compounds that, e.g., bind to, stimulate, increase, open, activate, facilitate, enhance activation, sensitize, or up regulate chemosensory receptor signal transduction.

Modifiers include compounds that, e.g., alter, directly or indirectly, the activity of a receptor or the interaction of a receptor with its ligands, e.g., receptor ligands, and optionally bind to or interact with activators or inhibitors; G Proteins; kinases (e.g., homologs of rhodopsin kinase and beta adrenergic receptor kinases that are involved in deactivation and desensitization of a receptor); and arresting, which also deactivate and desensitize receptors. Modifiers include genetically modified versions of chemosensory receptors, e.g., T1R family members, e.g., with altered activity, as well as naturally occurring and synthetic ligands, antagonists, agonists, small chemical molecules and the like. In the present invention this includes, without any limitation, sweet receptor ligands, umami receptor ligands, bitter receptor ligands, fatty acid ligands, bile receptor ligands, (agonists or antagonists). Modifiers also include compounds that allosterically bind to a receptor and change receptor activity. Modifiers also include enhancers. Depending on the structure, functional and activity properties, modifiers can enhance, potentiate, induce and/or block the physiological activity other chemosensory receptor ligands.

Enhancers as used herein are a type of modifier and refer to chemosensory receptor ligands that enhance, potentiate or multiply the effect of another chemosensory receptor ligand. For example, a sweet receptor enhancer can increase or multiply the sweetness of a chemosensory receptor ligand composition, when used in combination with a sweet receptor ligand (e.g., a sweetener, such as sucrose, fructose, glucose, saccharine, aspartame, sucralose, etc.). While a sweet receptor enhancer may or may not have sweet properties at some combinations when used in the absence of a sweet receptor ligand, sweet receptor enhancement occurs when the sweet receptor enhancer is used in combination with another sweet receptor ligand with the result that the resulting sweetness perceived in a subject is greater than the additive effects attributable to the sweet receptor enhancer's own sweet properties (if any), plus the sweetness attributable to the presence of the sweet receptor ligand.

"Treating" or "treatment" of any condition, disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers preventing or to delaying the onset of the disease or disorder.

"Therapeutically effective amount" or "effective amount" means the amount of a composition, compound, therapy, or course of treatment that, when administered to a patient for treating a disease, is sufficient to effect such treatment for the disease. The "therapeutically effective amount" will vary depending on the composition, the compound, the therapy, the course of treatment, the disease and its severity and the age, weight, etc., of the patient to be treated.

EXAMPLES

Example 1

Example 1a

Upper GI administration of one chemosensory receptor ligand in diabetic rats.

Numerous established and accepted diabetic rat models exist for the assessment of therapies for the treatment of diabetes. A single chemosensory receptor ligand (e.g., sweet) can be assayed for the treatment of diabetes in this established diabetic rat model as detailed in the example below.

Diabetic rats and Wistar rats are selected for administration of the chemosensory receptor ligand (e.g., sucralose) for the treatment of diabetes. Animals are grouped according to dosage, and increasing dosages (range of 0.01-100 mg/kg) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, PeptideYY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for five chemosensory receptor ligand types (Sweet, Umami, Fat, Bitter, and Bile Acid) according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 1b

Alternatively, the chemosensory receptor ligand, if not metabolized, is administered with a cognate metabolite in the experimental protocol above. For example in an alternative protocol, sucralose is administered along with glucose. The ligand may be administered in increasing doses with respect to a fixed dose of the cognate metabolite and vice versa.

Example 1c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 2

Example 2a

Lower GI administration of one chemosensory receptor ligand in diabetic rats.

Numerous established and accepted diabetic rat models exist for the assessment of therapies for the treatment of diabetes. A single chemosensory receptor ligand (e.g., sweet) can be assayed for the treatment of diabetes in this established diabetic rat model as detailed in the example below.

Diabetic rats and Wistar rats are selected for administration of the chemosensory receptor ligand (e.g., sucralose) for the treatment of diabetes. Animals are grouped according to dosage, and increasing dosages (sucralose range of 0.01-100 mg/kg) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, PeptideYY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for five chemosensory receptor ligand types (Sweet, Umami, Fat, Bitter, and Bile Acid) according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 2b

Alternatively, the chemosensory receptor ligand, if not metabolized, is administered with a cognate metabolite in the experimental protocol above. For example in an alternative protocol, sucralose is administered along with glucose. The ligand may be administered in increasing doses with respect to a fixed dose of the cognate metabolite and vice versa.

Example 2c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 3

Example 3a

Upper GI administration of two chemosensory receptor ligands in diabetic rats.

Numerous established and accepted diabetic rat models exist for the assessment of therapies for the treatment of diabetes. Two chemosensory receptor ligands can be assayed for the treatment of diabetes in this established diabetic rat model as detailed in the example below.

Diabetic rats and Wistar rats are selected for administration of the chemosensory receptor ligands for the treatment of diabetes and appropriate control perturbations (one ligand alone, saline alone). Animals are grouped according to dosage, and increasing dosages are utilized (increasing dose of one ligand with fixed doses of another ligand). Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, PeptideYY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for combinations of two chemosensory receptor ligands including chemosensory receptor ligand types Sweet, Umami, Fat, Bitter, and Bile Acid according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 3b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 3c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 4

Example 4a

Lower GI administration of two chemosensory receptor ligand in diabetic rats.

Numerous established and accepted diabetic rat models exist for the assessment of therapies for the treatment of diabetes. Two chemosensory receptor ligands can be assayed for the treatment of diabetes in this established diabetic rat model as detailed in the example below.

Diabetic rats and Wistar rats are selected for administration of two chemosensory receptor ligands for the treatment of diabetes. Animals are grouped according to dosage, and increasing dosages. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, PeptideYY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for combinations of two chemosensory receptor ligands including chemosensory receptor ligand types Sweet, Umami, Fat, Bitter, and Bile Acid according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 4b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 4c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 5

Example 5a

Upper GI administration of three chemosensory receptor ligands (sweet, umami, and Fat) in Diabetic Rats.

Numerous established and accepted diabetic rat models exist for the assessment of therapies for the treatment of diabetes. Three chemosensory receptor ligands (Sweet, umami, and fat) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the ligands sucralose, monosodium glutamate (MSG), and a fatty acid emulsion for the treatment of diabetes. Animals are grouped according to dosage, and increasing dosages (sucralose range of 0.01-100 mg/kg; MSG range of 0.01-100 mg/.kg; fatty acid emulsion (e.g., Intralipid®) of 10% solution at 0.5-10 ml/min over ranges of 10 sec.-to 5 min.) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, PeptideYY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 5b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 5c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 6

Example 6a

Lower GI administration of three chemosensory receptor ligands (sweet, umami, and fat) in diabetic rats.

Numerous established and accepted diabetic rat models exist for the assessment of therapies for the treatment of diabetes. Three chemosensory receptor ligands (Sweet, umami, and fat) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the chemosensory receptor ligands sucralose, monosodium glutamate (MSG), and a fatty acid emulsion. Animals are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min.) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 6b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 6c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 7

Example 7a

Upper GI administration of three chemosensory receptor ligands (Sweet, Umami, and Bitter) in diabetic rats.

Numerous established and accepted diabetic rat models exist for the assessment of therapies for the treatment of diabetes. Three chemosensory receptor ligands (Sweet, umami, and bitter) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the ligands sucralose, monosodium glutamate (MSG), and Quinine for the treatment of diabetes. Animals are grouped according to dosage, and increasing dosages (sucralose range of 0.01-100 mg/kg; MSG range of 0.01-100 mg/.kg; Quinine range of 0.01-100 mg/kg) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 7b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 7c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 8

Example 8a

Lower GI administration of three chemosensory receptor ligands (Sweet, Umami, and Bitter) in diabetic rats.

Numerous established and accepted diabetic rat models exist for the assessment of therapies for the treatment of diabetes. Three chemosensory receptor ligands (Sweet, umami, and bitter) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the chemosensory receptor ligands sucralose, monosodium glutamate (MSG), and Quinine for the treatment of diabetes. Animals are grouped according to dosage, and increasing dosages (sucralose range of 0.01-100 mg/kg; MSG range of 0.01-100 mg/kg; Quinine range of 0.01-100 mg/kg) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups, or all of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 8b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 8c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 9

Example 9a

Upper GI administration of three chemosensory receptor ligands (Sweet, Fat, and Bitter) in diabetic rats.

Numerous established and accepted diabetic rat models exist for the assessment of therapies for the treatment of diabetes. Three chemosensory receptor ligands (Sweet, fat, and bitter) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the ligands sucralose, fatty acid emulsion, and Quinine for the treatment of diabetes. Quinine and fat or fatty acid ligands do not require a cognate metabolite. Animals are grouped according to dosage, and increasing dosages (sucralose range of 0.01-100 mg/kg; fatty acid emulsion (e.g., Intralipid®) of 10% solution at 0.5-10 ml/min over ranges of 10 sec.-to 5 min; Quinine range of 0.01-100 mg/.kg) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 9b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 9c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 10

Example 10a

Lower GI administration of three chemosensory receptor ligands (Sweet, Fat, and Bitter) in diabetic rats.

Numerous established and accepted diabetic rat models exist for the assessment of therapies for the treatment of diabetes. Three chemosensory receptor ligands (Sweet, fat, and bitter) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the chemosensory receptor ligands sucralose, fatty acid emulsion, and Quinine for the treatment of diabetes. Animals are grouped according to dosage, and increasing dosages (sucralose range of 0.01-100 mg/kg; fatty acid emulsion (e.g., Intralipid®) of 10% solution at 0.5-10 ml/min over ranges of 10 sec.-to 5 min; Quinine range of 0.01-100 mg/kg) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups, or all of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 10b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 10c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 11

Example 11a

Upper GI administration of four chemosensory receptor Ligands (Sweet, Umami, Fat, and Bitter) in diabetic rats.

Numerous established and accepted diabetic rat models exist for the assessment of therapies for the treatment of diabetes. Four chemosensory receptor ligands (Sweet, MSG, fat, and bitter) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the ligands sucralose, Monosodium glutamate (MSG), fatty acid emulsion, and Quinine for the treatment of diabetes. Animals are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min; Quinine range of 0.01-100 mg/.kg) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 11b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 11c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 12

Example 12a

Lower GI administration of four chemosensory receptor ligands (Sweet, Umami, Fat, and Bitter) in diabetic rats.

Numerous established and accepted diabetic rat models exist for the assessment of therapies for the treatment of diabetes. Four chemosensory receptor ligands (Sweet, MSG, fat, and bitter) can be assayed for the treatment of diabetes (increased efficacy over single chemosensory receptor ligands, synergistic effects, etc.) in this established diabetic rat model as detailed in the example below.

Diabetic rats are and Wistar rats selected for administration of the chemosensory receptor ligands sucralose, Monosodium glutamate (MSG), fatty acid emulsion, and Quinine for the treatment of diabetes. Animals are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min; Quinine range of 0.01-100 mg/kg) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups or all of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 12b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 12c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 13

Example 13a

Upper GI administration of five chemosensory receptor ligands (Sweet, Umami, Fat, Bitter, and Bile Acid) in diabetic rats.

Numerous established and accepted diabetic rat models exist for the assessment of therapies for the treatment of diabetes. Five chemosensory receptor ligands (Sweet, MSG, fat, bitter, and Bile acid) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the ligands sucralose, Monosodium glutamate (MSG), fatty acid emulsion, Quinine and Chenodeoxycholic acid (CDC) for the treatment of diabetes. Animals are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-5 min; Quinine range of 0.01-100 mg/.kg; CDC range at 1-50 mMol solution at 1-10 ml/min over a range of 10 sec.-5 min.) are utilized. Chemosensory receptor ligands are instilled into the animals via silastic tubing inserted into the duodenum through the mouths of the lightly anesthetized animals.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 13b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 13c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 14

Example 14a

Lower GI administration of five chemosensory receptor ligands (Sweet, Umami, Fat, Bitter, and Bile Acid) in diabetic rats.

Numerous established and accepted diabetic rat models exist for the assessment of therapies for the treatment of diabetes. Five chemosensory receptor ligands (Sweet, MSG, fat, bitter, and Bile acid) can be assayed for the treatment of diabetes (increased efficacy over single chemosensory receptor ligands, synergistic effects, etc.) in this established diabetic rat model as detailed in the example below.

Diabetic rats and Wistar rats are selected for administration of the chemosensory receptor ligands sucralose, Monosodium glutamate (MSG), fatty acid emulsion, Quinine and Chenodeoxycholic acid (CDC) for the treatment of diabetes. Animals are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over a range of 10 sec.-5 min; Quinine range of 0.01-100 mg/kg; CDC range at 1-50 mMol solution at 1-10 ml/min over a range of 10 sec.-5 min.) are utilized. Chemosensory receptor ligands are instilled into the animals via silastic tubing inserted midway up the descending colon through the rectum of the lightly anesthetized animals.

Optionally, Dipeptidyl Peptidase IV (DPP IV) is inhibited in designated groups or all of the test animals to prevent degradation of the target hormones by endogenous peptidases. DPP IV inhibition is accomplished via co-administration of sitagliptin (10 mg/kg) at least one hour prior to chemosensory receptor ligand instillation.

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 14b

Alternatively, the chemosensory receptor ligands, if not metabolized, are administered with a cognate metabolite in the experimental protocol above. For example in an alternative protocol, sucralose is administered along with glucose. The ligands may be administered in increasing doses with respect to a fixed dose of the cognate metabolite and vice versa.

Example 14c

Alternatively, the experimental protocol above is performed with industry standard Diet Induced Obese rats and applicable controls (healthy rats). Parameters unique to the obesity systems are modified based on known standard assay conditions. Samples are collected and hormone assays performed as described above.

Example 15

Example 15a

Upper GI administration of one chemosensory receptor ligand in diabetic human subjects.

Diabetic human subjects can be assessed for the efficacy of therapies for the treatment of diabetes. A single chemosensory receptor ligand (e.g., sweet) can be assayed for the treatment of diabetes as detailed in the example below.

Diabetic human subjects are selected for administration of the chemosensory receptor ligand (e.g., sucralose) for the treatment of diabetes. Non-diabetic human subjects are included for controls. Subjects are grouped according to dosage, and increasing dosages (e.g., range of 0.01-100 mg/kg) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives. Samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for five chemosensory receptor ligand types (Sweet, Umami, Fat, Bitter, and Bile Acid) according the above protocol. Exemplary ligands and respective dose ranges are as follows:
Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 15b

Alternatively, the chemosensory receptor ligand, if not metabolized, is administered with a cognate metabolite in the experimental protocol above. For example in an alternative protocol, sucralose is administered along with glucose. The ligand may be administered in increasing doses with respect to a fixed dose of the cognate metabolite and vice versa.

Example 15c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 16

Example 15a

Lower GI administration of one chemosensory receptor ligand in diabetic human subjects.

Diabetic human subjects can be assessed for the efficacy of therapies for the treatment of diabetes. A single chemosensory receptor ligand (e.g., sweet) can be assayed for the treatment of diabetes as detailed in the example below.

Diabetic and non-diabetic human subjects are selected for administration of the chemosensory receptor ligand (e.g., sucralose) for the treatment of diabetes. Subjects are grouped according to dosage, and increasing dosages (e.g., range of 0.01-100 mg/kg) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives. Samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for five chemosensory receptor ligand types (Sweet, Umami, Fat, Bitter, and Bile Acid) according the above protocol. Exemplary ligands and respective dose ranges are as follows:
Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 16b

Alternatively, the chemosensory receptor ligand, if not metabolized, is administered with a cognate metabolite in the experimental protocol above. For example in an alternative protocol, sucralose is administered along with glucose. The ligand may be administered in increasing doses with respect to a fixed dose of the cognate metabolite and vice versa.

Example 16c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 17

Example 17a

Upper GI administration of two chemosensory receptor ligands in diabetic human subjects.

Diabetic human subjects can be assessed for the efficacy of therapies for the treatment of diabetes. Two chemosensory receptor ligands can be assayed for the treatment of diabetes as detailed in the example below.

Diabetic and nondiabetic human subjects are selected for administration of the chemosensory receptor ligands for the treatment of diabetes. Subjects are grouped according to dosage, and increasing dosages are utilized. Chemosensory receptor ligands and cognate metabolites are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives. Samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for combinations of two chemosensory receptor ligands including chemosensory receptor ligand types Sweet, Umami, Fat, Bitter, and Bile Acid according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 17b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 17c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 18

Example 18a

Lower GI administration of two chemosensory receptor ligands in diabetic human subjects.

Diabetic human subjects can be assessed for the efficacy of therapies for the treatment of diabetes. Two chemosensory receptor ligands can be assayed for the treatment of diabetes as detailed in the example below.

Diabetic and nondiabetic human subjects are selected for administration of the chemosensory receptor ligands for the treatment of diabetes. Subjects are grouped according to dosage, and increasing dosages (e.g., range of 0.01-100 mg/kg) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives. Samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

The experimental protocol is performed for combinations of two chemosensory receptor ligands including chemosensory receptor ligand types Sweet, Umami, Fat, Bitter, and Bile Acid according the above protocol. Exemplary ligands and respective dose ranges are as follows:

Sucralose: 0.01-100 mg/kg
MSG: 0.01-100 mg/kg
Fatty acid emulsion: 10% solution at 0.5-10 ml/min over ranges of 10 sec.-to 5 min.
Quinine: 0.01-100 mg/kg
Chenodeoxycholic acid (CDC): 1-50 mMol solution at 1-10 ml/min over a range of 10 sec.-5 min.

Example 18b

Alternatively, the chemosensory receptor ligands, if not metabolized, are administered with a cognate metabolite in the experimental protocol above. For example in an alternative protocol, sucralose is administered along with glucose.

The ligand may be administered in increasing doses with respect to a fixed dose of the cognate metabolite and vice versa.

Example 18c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 19

Example 19b

Upper GI administration of three chemosensory receptor ligands (Sweet, Umami, and Fat) in diabetic human subjects.

Diabetic human subjects can be assessed for the efficacy of therapies for the treatment of diabetes. Three chemosensory receptor ligands (Sweet, umami, and fat) can be assayed for the treatment of diabetes as detailed in the example below.

Diabetic and nondiabetic human subjects are selected for administration of the chemosensory receptor ligands sucralose, MSG and fatty acid emulsion for the treatment of diabetes. Subjects are grouped according to dosage, and increasing dosages (sucralose range of 0.01-100 mg/kg; MSG range of 0.01-100 mg/.kg; fatty acid emulsion (e.g., Intralipid®) of 10% solution at 0.5-10 ml/min over ranges of 10 sec.-to 5 min.) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-$\frac{1}{100}$ dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 19b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 19c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 20

Example 20a

Lower GI administration of three chemosensory receptor ligands (Sweet, Umami, and Fat) in diabetic human subjects.

Diabetic human subjects can be assessed for the efficacy of therapies for the treatment of diabetes. Three chemosensory receptor ligands (Sweet, umami, and fat) can be assayed for the treatment of diabetes as detailed in the example below.

Diabetic and nondiabetic human subjects are selected for administration of the chemosensory receptor ligands sucralose, MSG, and fatty acid emulsion for the treatment of diabetes. Subjects are grouped according to dosage, and increasing dosages (sucralose range of 0.01-100 mg/kg; MSG range of 0.01-100 mg/.kg; fatty acid emulsion (e.g., Intralipid®) of 10% solution at 0.5-10 ml/min over ranges of 10 sec.-to 5 min.) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test animals to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-$\frac{1}{100}$ dilution and valine pyrrolidine—100 µM final concentration) and preservatives. Samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 20b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 20c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 21

Example 21a

Upper GI administration of three chemosensory receptor ligands (Sweet, Umami, and Bitter) in diabetic human subjects.

Diabetic human subjects can be assessed for the efficacy of therapies for the treatment of diabetes. Three chemosensory receptor ligands (Sweet, umami, and bitter) can be assayed for the treatment of diabetes as detailed in the example below.

Diabetic and nondiabetic human subjects are selected for administration of the chemosensory receptor ligands sucralose, MSG, and Quinine for the treatment of diabetes. Subjects are grouped according to dosage, and increasing dosages (sucralose range of 0.01-100 mg/kg; MSG range of 0.01-100 mg/.kg; Quinine range of 0.01-100 mg/kg) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 21b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 21c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 22

Example 22a

Lower GI administration of three chemosensory receptor ligands (Sweet, Umami, and Bitter) in diabetic human subjects.

Diabetic human subjects can be assessed for the efficacy of therapies for the treatment of diabetes. Three chemosensory receptor ligands (Sweet, umami, and bitter) can be assayed for the treatment of diabetes as detailed in the example below.

Diabetic and nondiabetic human subjects are selected for administration of the chemosensory receptor ligands sucralose, MSG, and Quinine for the treatment of diabetes. Subjects are grouped according to dosage, and increasing dosages (sucralose range of 0.01-100 mg/kg; MSG range of 0.01-100 mg/.kg; Quinine range of 0.01-100 mg/kg) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 22b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 22c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 23

Example 23a

Upper GI administration of three chemosensory receptor ligands (Sweet, Fat, and Bitter) in diabetic human subjects.

Diabetic human subjects can be assessed for the efficacy of therapies for the treatment of diabetes. Three chemosensory receptor ligands (Sweet, fat, and bitter) can be assayed for the treatment of diabetes as detailed in the example below.

Diabetic and nondiabetic human subjects are selected for administration of the chemosensory receptor ligands sucralose, fatty acid emulsion, and Quinine for the treatment of diabetes. Subjects are grouped according to dosage, and increasing dosages (sucralose range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-$\frac{1}{100}$ dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 23b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 23c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 24

Example 24a

Lower GI administration of three chemosensory receptor ligands (Sweet, Fat, and Bitter) in diabetic human subjects.

Diabetic human subjects can be assessed for the efficacy of therapies for the treatment of diabetes. Three chemosensory receptor ligands (Sweet, fat, and bitter) can be assayed for the treatment of diabetes as detailed in the example below.

Diabetic and nondiabetic human subjects are selected for administration of the chemosensory receptor ligands sucralose, fatty acid emulsion, and quinine for the treatment of diabetes. Subjects are grouped according to dosage, and increasing dosages (sucralose range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-$\frac{1}{100}$ dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 24b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 24c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 25

Example 25a

Upper GI administration of four chemosensory receptor ligands (Sweet, Msg, Fat, and Bitter) in diabetic human subjects.

Diabetic human subjects can be assessed for the efficacy of therapies for the treatment of diabetes. Four chemosensory receptor ligands (Sweet, MSG, fat, and bitter) can be assayed for the treatment of diabetes as detailed in the example below.

Diabetic and nondiabetic human subjects are selected for administration of the chemosensory receptor ligand sucralose, MSG, fatty acid emulsion, and Quinine for the treatment of diabetes. Subjects are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 25b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 25c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 26

Example 26a

Lower GI administration of four chemosensory receptor ligands (Sweet, Msg, Fat, and Bitter) in diabetic human subjects.

Diabetic human subjects can be assessed for the efficacy of therapies for the treatment of diabetes. Four chemosensory receptor ligands (Sweet, MSG, fat, and bitter) can be assayed for the treatment of diabetes as detailed in the example below.

Diabetic and nondiabetic human subjects are selected for administration of the chemosensory receptor ligand sucralose, MSG, fatty acid emulsion, and Quinine for the treatment of diabetes. Subjects are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 26b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 26c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 27

Example 27a

Upper GI administration of five chemosensory receptor ligands (Sweet, Msg, Fat, Bitter, and Bile Acid) in diabetic human subjects.

Diabetic human subjects can be assessed for the efficacy of therapies for the treatment of diabetes. Five chemosensory receptor ligands (Sweet, MSG, fat, bitter, and bile acid) can be assayed for the treatment of diabetes as detailed in the example below.

Diabetic and nondiabetic human subjects are selected for administration of the chemosensory receptor ligands sucralose, MSG, Quinine, fatty acid emulsion, and Chenodeoxycholic acid (CDC) for the treatment of diabetes. Subjects are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg; CDC range at 1-50 mMol solution at 1-10 ml/min over a range of 10 sec.-5 min.) are utilized. Chemosensory receptor ligands are instilled into the subjects via specialized tubing (e.g., Ryle's tube) inserted into the duodenum/jejunal area. The tubes are introduced nasogastrically and allowed to advance by peristalsis into the final location.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 27b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 27c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 28

Example 28a

Lower GI administration of five chemosensory receptor ligands (Sweet, Msg, Fat, Bitter, and Bile Acid) in diabetic human subjects.

Diabetic human subjects can be assessed for the efficacy of therapies for the treatment of diabetes. Five chemosensory receptor ligands (Sweet, MSG, fat, bitter, and bile acid) can be assayed for the treatment of diabetes as detailed in the example below.

Diabetic and nondiabetic human subjects are selected for administration of the chemosensory receptor ligands sucralose, MSG, Quinine, fatty acid emulsion, and Chenodeoxycholic acid (CDC) for the treatment of diabetes. Subjects are grouped according to dosage, and increasing dosages (sucralose range of 0.01-100 mg/kg; MSG range of 0.01-100 mg/kg; fatty acid emulsion (e.g., Intralipid®) of 10% solution at 0.5-10 ml/min over ranges of 10 sec.-to 5 min.; Quinine range of 0.01-100 mg/kg; CDC range at 1-50 mMol solution at 1-10 ml/min over a range of 10 sec.-5 min.) are utilized. Chemosensory receptor ligands are instilled into the subjects via nasogastric tubing inserted midway up the descending colon through the rectum of the human subjects.

Optionally, Dipeptidyl Peptidase IV (DPP IV) is inhibited in designated groups, or all, of the test subjects to prevent degradation of the target hormones by endogenous peptidases. DPP IV inhibition is accomplished via co-administration of sitagliptin (100 mg/subject) at least one hour prior to chemosensory receptor ligand instillation.

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase.

Example 28b

Alternatively, the chemosensory receptor ligands, if not metabolized, are administered with a cognate metabolite in the experimental protocol above. For example in an alternative protocol, sucralose is administered along with glucose. The ligand may be administered in increasing doses with respect to a fixed dose of the cognate metabolite and vice versa.

Example 28c

Alternatively, the experimental protocol above is performed with obese human subjects or overweight human subjects and applicable controls (healthy human subjects). Parameters unique to the obesity systems are modified based on known standard assay conditions. Samples are collected and hormone assays performed as described above.

Example 29

Dose-response studies for individual and combinations of chemosensory receptor ligands.

Chemosensory receptor ligands corresponding to each of the chemosensory receptor (Sucralose, MSG, Quinine, fatty acid emulsion, and Chenodeoxycholic acid) and optionally cognate metabolites are individually administered in diabetic rat upper GI and lower GI systems as well as diabetic human upper GI and lower GI systems (see previous examples for administration protocols for the rat and human systems in both the upper GI and lower GI) to determine the optimum doses for each chemosensory receptor ligand as well as the optional cognate metabolite (e.g., glucose). Subjects are administered sitagliptin (DPP IV inhibitor) at 10 mg/kg or 100 mg/subject in rats and humans respectively at least 60 minutes prior to chemosensory receptor ligand and optional cognate metabolite infusion.

Chemosensory receptor ligands and optional cognate metabolites are administered individually at increasing amounts (mg/kg/min), where each subject is administered a set mg/kg/min dose and the dose is maintained at this set level for a 30 minute period. Blood samples are collected at frequent intervals (e.g., every 1, 2, or 5 minutes) throughout the 30 minute period and assayed for hormone levels. Hormones assayed include CCK, GIP, GLP-1, Oxyntomodulin, Peptide YY, Insulin, Glucagon, C-peptide, Ghrelin, and GLP-2. Assays for the hormones are performed using standard ELISA methodologies. Results are analyzed for efficacy of chemosensory receptor ligand and optional cognate metabolite administration for the treatment of diabetic rats and humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase and change according to the dosages given.

50% of maximal response dose and 50% of the maximum tolerated dose are determined for each chemosensory receptor ligand. Optionally, 25% of maximal response dose is determined for a cognate metabolite.

Alternatively, the experimental protocol above is performed with Diet Induced Obese rats, obese human subjects or overweight human subjects, and applicable controls (healthy rat or human subjects). Parameters unique to the obesity systems are modified based on known standard assay conditions. Samples are collected and hormone assays performed as described in Examples 1-28, above.

Example 30

Experiments to determine the effect of optional cognate metabolite co-administration with the chemosensory receptor ligands are performed using the human and rat systems described in example 29.

Subjects (rats and humans, in both upper GI and lower GI) are administered sitagliptin (DPP IV inhibitor) at 10 mg/kg or 100 mg/subject in rats and humans respectively at least 60 minutes prior to chemosensory receptor ligand and glucose co-infusion. The chemosensory receptor ligands are individually co-administered at the 50% of maximal response dose with glucose at the 25% of maximal response dose.

Blood samples are collected at frequent intervals (e.g., every 1, 2, or 5 minutes) throughout the 30 minute period and assayed for hormone levels via standard ELISA methodologies including CCK, GIP, GLP-1, Oxyntomodulin, Peptide YY, Insulin, Glucagon, C-peptide, Ghrelin and GLP-2. Assays for the hormones are performed using standard ELISA methodologies. Results are analyzed for efficacy of chemosensory receptor ligand and cognate metabolite administration for the treatment of diabetic rats and humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase and change according to the dosages given.

The effect of co-administration of a cognate metabolite (glucose) with each chemosensory receptor ligand, as well as 50% of maximal dose and 50% of maximum tolerated dose is thus determined.

Alternatively, the experimental protocol above is performed with Diet Induced Obese rats, obese human subjects or overweight human subjects, and applicable controls (healthy rat or human subjects). Parameters unique to the obesity systems are modified based on known standard assay conditions. Samples are collected and hormone assays performed as described in Examples 1-28, above.

Example 31

Experiments to determine the effect of the administration of combinations of chemosensory receptor ligands are performed in rat and human systems as described in examples 1-28.

Each chemosensory receptor ligand of the combinations found in Examples 1-28 is administered at the 50% of maximal response dose (determined as described in Examples 28 and 29). Duplicate experiments are performed where optional cognate metabolites (e.g., glucose) is co-administered at the 25% of maximal response (determined as described in Examples 29 and 30).

Rat Blood Sample Collection

Blood samples are collected via cannulation of the tail vein, and samples are withdrawn at baseline, 15, 30, 60 and 120 minutes post-instillation. Blood samples are collected in collection tubes containing standard cocktails of peptidase inhibitors and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin and GLP-2. Assays for the hormones are performed using standard ELISA methodologies. Results are analyzed for efficacy of chemosensory receptor ligand and cognate metabolite administration for the treatment of diabetic rats. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase and change according to the dosages given.

Human Blood Sample Collection

Blood samples are collected at baseline, at 15 minute intervals for the first hour post-instillation, and at 30 minute intervals for hours 2-4 post-instillation. Blood samples are collected in collection tubes containing standard cocktails of protease inhibitors (e.g., Sigma P8340-1/100 dilution and valine pyrrolidine—100 µM final concentration) and preservatives, and samples are stored at −25° C. until assayed. Blood samples are assayed for the presence of hormones related to insulin regulation, including CCK, GIP, GLP-1, Oxyntomodulin, Peptide YY, Insulin, Glucagon, C-peptide, Ghrelin and GLP-2. Assays for the hormones are performed using standard ELISA methodologies. Results are analyzed for efficacy of chemosensory receptor ligand and cognate metabolite administration for the treatment of diabetic humans. Metabolites and other analyte concentrations, including glucose, free fatty acids, triglycerides, calcium, potassium, sodium, magnesium, phosphate, are also assessed. Circulating concentrations of at least one of the measured GLP-1, GLP-2, GIP, oxyntomodulin, Peptide YY, CCK, glucagon and insulinogenic index are expected to increase and change according to the dosages given.

Example 32

Exemplary composition weighted to sweet receptor ligands and its administration.

| Composition A | | | |
|---|---|---|---|
| Chemosensory Receptor Ligand | Per oral solid dosage form (mg) | Dose (mg) | B.i.d. Daily Total |
| Rebaudioside A | 200 | 800 | 1600 |
| Stevioside | 100 | 400 | 800 |
| Sucralose | 100 | 400 | 800 |
| Quinine | 2 | 8 | 16 |
| L-Glutamine | 50 | 200 | 400 |
| Oleic Acid | 50 | 200 | 400 |

A single oral solid dosage form (e.g., tablet, pill, capsule, and the like) includes the listed chemosensory receptor ligand components. A single dose for administration is a set of 4 units of the oral solid dosage form (e.g., 4 tablets or 4 capsules). Each of the 4 units contains identical chemosensory receptor ligand components; however each individual unit is formulated for release 80% of the chemosensory receptor ligand components at a different pH: pH 5.5, pH 6.0, pH 6.5, and pH 7.0 respectively. 20% of the chemosensory receptor ligand components are released immediately. B.i.d. dosing occurs at 30 minutes to 1 hour prior to breakfast or the first meal of the day and 30 minutes to 1 hour prior to lunch or the second meal of the day. Alternatively, other dosing occurs, depending on the time of day during which food intake is desired to be reduced, for example, b.i.d. dosing 30 minutes to 1 hour prior to lunch or the second meal of the day and 30 minutes to 1 hour prior to dinner or the third meal of the day, or t.i.d. dosing 30 minutes—1 hour before each meal of the day.

Example 33

Exemplary composition weighted to sweet receptor ligands and its administration.

| Composition B | | | |
|---|---|---|---|
| Chemosensory Receptor Ligand | Per oral solid dosage form (mg) | Dose (mg) | B.i.d. Daily Total |
| Rebaudioside A | 200 | 800 | 1600 |
| Stevioside | 100 | 400 | 800 |
| Sucralose | 100 | 400 | 800 |
| Quinine | 2 | 8 | 16 |
| L-Glutamine | 50 | 200 | 400 |

A single oral solid dosage form (e.g., tablet, pill, capsule, and the like) includes the listed chemosensory receptor ligand components. A single dose for administration is a set of 4 units of the oral solid dosage form (e.g., 4 tablets or 4 capsules). Each of the 4 units contains identical chemosensory receptor ligand components; however each individual unit is formulated for release at a different pH: pH 5.5, pH 6.0 or pH 6.5. One unit releases approximately 20% of its components in about 15 to about 60 mins after encountering an intestinal pH of approximately 5.5, and releases the remaining 80% of its components in about 2 hrs. Another unit releases approximately 20% of its components in about 15 to about 60 mins after encountering an intestinal pH of approximately 6.0, and releases the remaining 80% of its components in about 4 hrs. A third unit releases approximately 20% of its components in about 15 to about 60 mins after encountering an intestinal pH of approximately 6.5, and releases the remaining 80% of its components in about 4 hrs. A fourth unit releases approximately 20% of its components in about 15 to about 60 mins after encountering an intestinal pH of approximately 6.0, and releases the remaining 80% of its components in about 7 hrs. B.i.d. dosing occurs at 30 minutes to 1 hour prior to breakfast or the first meal of the day and 30 minutes to 1 hour prior to lunch or the second meal of the day.

Example 34

Formulation of Composition B

The chemosensory receptor ligands of Composition B (Rebaudioside A, stevioside, sucralose, quinine and L-glutamine) are formulated into bilayer tablet cores with the excipients as indicated in the following table (expressed in proportional units).

| | IR | CR7 | CR4 | CR2 |
|---|---|---|---|---|
| Stevioside | 13.3 | 16.0 | 16.0 | 16.0 |
| Sucralose | 13.3 | 16.0 | 16.0 | 16.0 |
| Quinine sulfate dihydrate | 0.29 | 0.4 | 0.4 | 0.4 |
| L-Glutamine | 6.7 | 8.0 | 8.0 | 8.0 |

-continued

|  | IR | CR7 | CR4 | CR2 |
|---|---|---|---|---|
| Reb A | 26.7 | 32.0 | 32.0 | 32.0 |
| Prosol HD90 | 28.71 | 9.6 | 12.0 | 15.6 |
| Pruv | 3.0 | 3.0 | 3.0 | 3.0 |
| Croscarmelose Sodium | 4.0 | — | — | — |
| Methocel K4M | — | 11.0 | 8.6 | 5.0 |
| Klucel EXF | 4.0 | 4.0 | 4.0 | 4.0 |

The IR column of the above table refers to 20% of the mass of the bilayer tablet that releases its contents in about 15 to about 60 minutes. CR2, CR4, and CR7 refer to the remaining 80% of the components that release over approximately 2, 4 or 7 hrs. A bilayer tablet core has an IR compound and one of the CR, CR4 or CR7 components. With the exception of stevioside (>90 purity), the purity of all ingredients is >99.8% and the concentrations of all impurities for all ingredients are significantly below the limits set under International Conference on Harmonisation (ICH) guidance.

The bilayer tablet cores are coated with the following coating compositions for release at the indicated pH in the following table (expressed in proportional units).

| Composition | IR/CR 2 hr pH 5.5 | IR/CR 4 hr pH 6.0 | IR/CR 4 hr pH 6.5 | IR/CR 7 hr pH 6.0 |
|---|---|---|---|---|
| Eudragit L30 D55 | 833.4 | 750.06 | 625.05 | 750.06 |
| Eudragit FS 30D | 0 | 83.34 | 208.35 | 83.34 |
| Talc | | | 125.0 | |
| Triethylcitrate | | | 25.0 | |
| Water | | | 1016 | |

Example 35

Assessing efficacy of Composition B as described in Example 33 and 34 in obese human subjects.

The objective of this study is to assess the efficacy of a composition and administration as described in Example 33 on weight loss and gylcemic control in obese human subjects. The study design is a placebo-controlled, randomized, double blinded trial at three testing centers and a duration of 16 weeks.

Total patient population: N=300. Patients are selected based on a body mass index of greater than or equal to 30. 20% of the patient population can be diabetic (D&E, or stable metformin).

The dietary instruction is given at randomization only and excludes hypocaloric diets. Patients are assessed monthly with weight measurements and blood sampling along with a patient questionnaire. Blood samples are assayed for the presence of metabolic hormones including CCK, GIP, GLP-1, Oxyntomodulin, Peptide YY, insulin, glucagon, C-peptide, ghrelin and GLP-2 as well as plasma glucose via A1C (glycated hemoglobin) concentrations.

Example 36

Assessing the effects of Composition B as described in Example 33 and 34 in healthy human subjects.

The objective of this study is to assess the effect of a composition and administration as described in Example 33 on hormone excursions following two meals in healthy human subjects. The study design is a 8-day placebo-controlled, cross-over trial. Healthy patients are divided into two groups that receive either placebo or the composition described in Example 33 on Days 1-3 twice daily, 30 minutes to 1 hour prior to breakfast and lunch. On Day 4, blood samples are collected prior to administration of the composition and at 15 minute intervals post-meal for 2 hours. Blood samples are collected in collection tubes containing standard cocktails of protease inhibitors and preservatives, and samples are stored at −25° C. until assayed. The process is repeated for Days 5-8 with the placebo group receiving the composition and the composition group now receiving the placebo.

Blood samples are assayed for the presence of metabolic hormones including CCK, GIP, GLP-1, Oxyntomodulin, Peptide YY, insulin, glucagon, C-peptide, ghrelin and GLP-2 as well as plasma glucose via A1C (glycated hemoglobin) concentrations. Positive patient outcome and response to the study is defined as an increase in GLP-1, GIP, Peptide YY, or Oxyntomodulin plasma AUC with the composition as described in Example 33 over placebo and/or a decrease in glucose AUC with the composition as described in Example 33 over placebo. A 20% increase of the hormone, or a 20% decrease in glucose is defined as very significant.

Example 37

An 8-Day, Randomized, Cross-Over, Blinded, Placebo-Controlled, Single Center Study Assessing the Efficacy of Composition B as Described in Example 33 and 34 on Meal-Driven Hormone Levels in the Circulation of Obese Volunteers An 8 day clinical study as designed to examine the effect of Composition B on meal-driven, gut hormone profiles in overweight volunteers.

Indication

The effect of Composition B versus Placebo is compared on gut hormone release.

Rationale

Study: To examine Composition B's effect on gut hormone release and therapeutic possibility in the treatment of obesity.

Sitagliptin (Januvia): Because gut hormones GLP-1 and PYY as well as others are rapidly broken down by the peptidase DPP-IV, subjects were asked to ingest 100 mg of the DPP-IV inhibitor sitagliptin (Januvia) an approved medication for the treatment of diabetes on the morning of each meal test day (day 4 and 8).

Objectives

Primary: To assess the effects of Composition B on Glucagon-Like Peptide-1, Peptide YY and other gut hormone concentrations in the bloodstream before, and during, a standard breakfast and lunch after administration of Composition B or Placebo.

Secondary: To assess the effects of Composition B on plasma glucose, insulin, and triglycerides serum concentrations, before, and during, a standard breakfast and lunch after administration of Composition B or Placebo.

Trial Design

The trial was a double-blind, randomized, single center study using a cross-over design. Male and female subjects with obesity were included in this study. Approximately 10 eligible subjects who had given their informed consent to participate were randomized to one of the following treatments:

Composition B
Placebo

Subjects were randomized at visit 2 to equal groups of 5 on Placebo and 5 on Composition B. They were asked to take their assigned therapeutic product (Composition B or Placebo) by mouth 30-60 minutes prior to breakfast and lunch or the first and second meal of the day. The therapeutic product was composed of 4 tablets packaged together in a sealed pouch. After 3 days of therapy, subjects returned to the clinic early on the morning of the 4th day (visit 3) where they took the therapeutic product and ingested 100 mg of sitagliptin (Januvia), and subsequently received the test standard meals. During the meals, blood was drawn from an indwelling catheter for various hormone and analyte measurements. After the meal tests were administered on the 4th day, subjects on Placebo and Composition B were crossed over to the other therapy and asked to ingest the therapeutic product for days 5-7. On day 8 (visit 4), subjects returned to the clinic early on the morning of the 8th day where they took the therapeutic product and 100 mg of sitagliptin, and subsequently received the test standard meals, similarly to day 4.

Inclusion Criteria
- Male/female
- All races
- Impaired fasting glucose/Prediabetes (fasting blood glucose 100-125 mg/dl)
- Diabetes (fasting blood glucose >126 mg/dl) if fasting blood glucose is less or equal to 140 mg/dl on no current diabetes treatment
- Smokers allowed (but not smoking during the study period)
- BMI 27-40 inclusive
- Healthy with no health problems requiring medications
- Willingness to take 4 pills twice per day
- Willingness to adhere to protocol Exclusion Criteria
- Age <18 and >65 years
- BMI less than 27
- BMI over 40
- Any current drug treatment (prescription or over-the-counter medications, including any antacids such as Rolaids or Pepsid). Subjects may take acute intermittent over-the-counter medications (such as Tylenol), if needed.
- Any nutritional supplement for weight loss
- Any chronic disease requiring medication
- Surgery of any kind 6 months prior
- History of gastrointestinal surgery
- History of weight-loss within 3 months of screening
- History of major weight loss (>20% body weight)
- Current infections
- Inability to swallow 8 pills per day
- History of diabetes requiring drug therapy
- Blood pressure >160 mmHg systolic or 95 mmHg diastolic
- Resting heart rate >90 BPM
- Pregnancy or desire to become pregnant during the study
- Excessive alcohol intake (more than 14 drinks/week)

Trial Treatments

Subjects were randomized in a 1:1 ratio to one of the following treatment arms: Composition B or Placebo.

At screening (Visit 1), inclusion/exclusion was assessed.

At randomization (Visit 2), subjects were assigned to one of two treatment groups, Placebo or Composition B. The assigned treatment was taken for 4 days. At Visit 3 subjects originally assigned to Placebo at Visit 2 was switched to Composition B, and subjects originally assigned to Composition B at Visit 2 was switched to Placebo and subjects took their newly assigned treatment for an additional 4 days.

Activity Schedule

|  | Screening (Visit 1) | Randomization/Day 1 (Visit 2) | Day 2 | Day 3 | Day 4 (Visit 3) | Day 5 | Day 6 | Day 7 | Day 8 (Visit 4) |
|---|---|---|---|---|---|---|---|---|---|
| Clinic Visit | X | X |  |  | X |  |  |  | X |
| Informed Consent | X |  |  |  |  |  |  |  |  |
| Vital Signs | X | X |  |  | X |  |  |  | X |
| Height/Weight | X | X |  |  | X |  |  |  | X |
| Med/Surg Hx or changes | X | X |  |  | X |  |  |  | X |
| Con Meds | X | X |  |  | X |  |  |  | X |
| Demographics | X |  |  |  |  |  |  |  |  |
| AEs |  |  |  |  | X |  |  |  | X |
| Chemistry Panel | X |  |  |  |  |  |  |  |  |
| Pregnancy Test | X |  |  |  |  |  |  |  |  |
| Glucose |  | X |  |  | X |  |  |  | X |
| Insulin |  | X |  |  | X |  |  |  | X |
| Triglycerides |  | X |  |  | X |  |  |  | X |
| GLP-1 |  | X |  |  | X |  |  |  | X |
| PYY |  | X |  |  | X |  |  |  | X |
| Amylin (active and total) |  | X |  |  | X |  |  |  | X |
| Ghrelin (active and total) |  | X |  |  | X |  |  |  | X |
| C-Peptide |  | X |  |  | X |  |  |  | X |
| Oxyntomodulin |  | X |  |  | X |  |  |  | X |
| GIP (total) |  | X |  |  | X |  |  |  | X |
| CCK |  | X |  |  | X |  |  |  | X |
| Placebo/Composition B dosing |  | X | X | X | X | X | X | X | X |
| Januvia dosing |  |  |  |  | X |  |  |  | X |
| Meal Test |  |  |  |  | X |  |  |  | X |

Volunteer Instructions

During the period of study, volunteers were instructed to go about their usual daily lives. They were discouraged from engaging in strenuous exercise or changing their usual lifestyle. Volunteers were instructed not to smoke or drink coffee during the study period. They were to report any side effects, or changes in how they feel. If they had the need to take acute medication during the trial such as aspirin, acetaminophen, or allergy medications they were instructed to report it but they were told that it would not disqualify them from the study.

Study Procedures
Screening (Visit 1) assessed subjects for inclusion/exclusion.
Randomization—Day 1 (Visit 2)
Randomization occurred about 4 weeks of Visit 1.
Volunteers showed up to clinic fasting prior to 8:00 AM.
Vital signs, height, weight, baseline bloods (fasting and postprandial insulin, glucose, triglyceride, GLP-1 (active and total), PYY (active and total), GIP, ghrelin (active and total), amylin (active and total), C-Peptide, CCK and oxyntomodulin) were taken.
Assigned treatment arm (randomization)
Composition B or Placebo tablets was provided for 4 days of treatment (8 packets, each containing 4 tablets).
Volunteers took 4 tablets (one packet) approximately 30-60 minutes prior to breakfast and lunch or the first and second meal of the day.
First dose (4 tablets) was taken on visit 1
Volunteers were allowed to have breakfast after their fasting blood draws and after taking their first dose (4 tablets)
Volunteers were discharged from the clinic and instructed to take their tablets each day 30-60 minutes prior to breakfast and lunch on days 1, 2 and 3.
Volunteers were instructed to return to the clinic on day 4 fasting
Day 2
Volunteers took 4 tablets (one packet) approximately 30-60 minutes prior to breakfast and lunch or the first and second meal of the day.
Day 3
Volunteers took 4 tablets (one packet) approximately 30-60 minutes prior to breakfast and lunch or the first and second meal of the day.
Day 4 (Visit 3)—Meal Profiles
Volunteers showed up to clinic fasting prior to 8:00 AM.
Blood drawing access was established via an indwelling catheter.
Vital signs, height, weight were taken
At t=−90 minutes baseline1 bloods were drawn and processed as appropriate for each analyte (fasting and postprandial insulin, glucose, triglyceride, GLP-1 (active and total), PYY (active and total), GIP, ghrelin (active and total), amylin (active and total), C-Peptide, CCK and oxyntomodulin).
At t=−80 minutes one tablet of Januvia 100 mg (sitagliptin 100 mg) was administered by mouth with a 4 oz glass of water.
At t=−60 minutes one dose (4 tablets) of Composition B or Placebo was administered by mouth with 4 oz of water.
At t=−5 minutes baseline bloods were drawn and processed as appropriate for each analyte.
At t=0 breakfast was provided to be consumed over at most 20 minutes. Breakfast was 600 Kcal, composed with a caloric distribution of 60% carbohydrate, 15% protein and 25% fat.
At t=30 minutes bloods were drawn and processed as appropriate for each analyte.
At t=60 minutes bloods were drawn and processed as appropriate for each analyte.
At t=90 minutes bloods were drawn and processed as appropriate for each analyte.
At t−120 minutes bloods were drawn and processed as appropriate for each analyte.
At t=180 minutes bloods were drawn and processed as appropriate for each analyte.
At t=185 minutes, one dose (4 tablets) of Composition B or Placebo was administered by mouth with 4 oz of water.
At t=235 minutes bloods were drawn and processed as appropriate for each analyte.
At t=240 minutes lunch was provided to be ingested over at most 20 minutes
Lunch was provided to be consumed over at most 20 minutes. Lunch was 1000 Kcal, composed with a caloric distribution of 60% carbohydrate, 15% protein and 25% fat.
At t=270 minutes Bloods were drawn and processed as appropriate for each analyte.
At t=300 minutes bloods were drawn and processed as appropriate for each analyte.
At t=330 minutes bloods were drawn and processed as appropriate for each analyte.
At t=360 minutes bloods were drawn and processed as appropriate for each analyte.
At t=420 minutes bloods were drawn and processed as appropriate for each analyte.
At t=480 minutes bloods were drawn and processed as appropriate for each analyte.
After the 480 minute blood draw the volunteer was eligible for discharge.
Upon discharge the volunteer was provided with 4 days of drug (8 packets).
Volunteers were discharged from the clinic and instructed to take their tablets each day 30-60 minutes prior to breakfast and lunch on days 1, 2 and 3.
Volunteers were instructed to return to the clinic on day 8 fasting.
Day 5
Volunteers took 4 tablets (one packet) approximately 30-60 minutes prior to breakfast and lunch or the first and second meal of the day.
Day 6
Volunteers took 4 tablets (one packet) approximately 30-60 minutes prior to breakfast and lunch or the first and second meal of the day.
Day 7
Volunteers took 4 tablets (one packet) approximately 30-60 minutes prior to breakfast and lunch or the first and second meal of the day.
Day 8 (Visit 4)—Meal Profiles
Volunteers showed up to clinic fasting prior to 8:00 AM.
Blood drawing access was established via an indwelling catheter.
Vital signs, height, weight are taken.
At t=−90 minutes baseline1 bloods were drawn and processed as appropriate for each analyte.
At t=−80 minutes one tablet of Januvia 100 mg (sitagliptin 100 mg) was administered by mouth with a 4 oz glass of water
At t=−60 minutes one dose (4 tablets) of Composition B or Placebo was administered by mouth with 4 oz of water
At t=−5 minutes baseline2 bloods were drawn and processed as appropriate for each analyte.
At t=0 breakfast was provided to be consumed over at most 20 minutes. Breakfast was 600 Kcal, composed with a caloric distribution of 60% carbohydrate, 15% protein and 25% fat.
At t=30 minutes bloods were drawn and processed as appropriate for each analyte.
At t=60 minutes bloods were drawn and processed as appropriate for each analyte.
At t=90 minutes bloods were drawn and processed as appropriate for each analyte.

At t=120 minutes bloods were drawn and processed as appropriate for each analyte.

At t=180 minutes bloods were drawn and processed as appropriate for each analyte.

At t=185 minutes, one dose (4 tablets) of Composition B or Placebo was administered by mouth with 4 oz of water.

At t=235 minutes bloods were drawn and processed as appropriate for each analyte.

At t=240 lunch was provided to be consumed over at most 20 minutes. Lunch was 1000 Kcal, composed with a caloric distribution of 60% carbohydrate, 15% protein and 25% fat.

At t=270 minutes Bloods were drawn and processed as appropriate for each analyte.

At t=300 minutes bloods were drawn and processed as appropriate for each analyte.

At t=330 minutes bloods were drawn and processed as appropriate for each analyte.

At t=360 minutes bloods were drawn and processed as appropriate for each analyte.

At t=420 minutes bloods were drawn and processed as appropriate for each analyte.

At t=480 minutes bloods were drawn and processed as appropriate for each analyte.

After the 480 minutes blood draw the volunteer was eligible for discharge.

Results

It was observed that the circulating hormone levels and/or concentrations of at least GLP (total), GLP (active), insulin, PYY (total) and PYY 3-36 were increased with Composition B as compared to the circulating hormone levels and/or concentrations with a placebo composition.

Example 38

Satiety Study

Satiety and satiation studies are performed in the population of interest (e.g. healthy lean, overweight, obese, morbidly obese, patients with type 2 diabetes) in a controlled setting appropriate for such studies. Studies are conducted in a randomized, double-blind, placebo controlled fashion to evaluate the effect of compositions provided herein, including Composition B and/or B. Patients are asked to complete a satiety questionnaire and visual analog scales (VAS) to determine their level of hunger prior to food intake and satiation after food intake. Also they are probed regarding food preferences and cravings. Volunteers have access to a buffet and are free to access as much food as desired. The food is weighed or otherwise quantitated so as to determine the total caloric value of the food ingested. A satiety quotient is calculated (i.e. VAS for satiety divided by the amount of calories ingested. Subjects in active arms of the studies report an increase the satiety index, i.e., produce greater satiety at a lower caloric intake when compared to placebo.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A composition comprising a sweet receptor ligand, wherein the sweet receptor ligand is a non-nutritive agonist of the receptor and the composition is adapted to release the sweet receptor ligand to one or more of the duodenum, jejunum, ileum, caecum, colon and/or rectum of a subject.

2. A composition according to claim 1, wherein the composition further releases at least some of the sweet receptor ligand in the stomach.

3. A composition according to claim 1, wherein the composition is adapted to release the sweet receptor ligand distal to the duodenum.

4. A composition according to claim 3, wherein the composition is adapted to release the sweet receptor ligand to the jejunum, ileum, caecum, colon and/or rectum.

5. A composition according to claim 1, wherein the composition releases at an onset of about 5 to about 45 minutes, about 105 to about 135 minutes, about 165 to about 195 minutes, about 225 to about 255 minutes or a combination of times thereof following administration to a subject.

6. A composition according to claim 1, wherein the composition releases at an onset of about pH 5.0, about pH 5.5, about pH 6.0, about pH 6.5, about pH 7.0, or a combination thereof following administration to a subject.

7. A composition according to claim 1, wherein the composition further comprises a bitter receptor ligand, an umami receptor ligand, a fat receptor ligand, a bile acid receptor ligand or any combination thereof.

8. A composition according to claim 1, wherein the non-nutritive sweet receptor ligand is selected from the group consisting of sucralose, aspartame, Stevioside, Rebaudioside A, Rebaudioside B, Rebaudioside C , Rebaudioside D, Rebaudioside E, Rebaudioside F, Neotame, acesulfame-K and saccharin.

9. A composition according to claim 7, wherein the bitter receptor ligand is selected from the group consisting of a flavanone, a flavone, a flavonol, a flavan, a phenolic flavonoid, an isoflavone, a limonoid aglycone, a glucosinolate or hydrolysis product thereof and an organic isothiocyanate.

10. A composition according to claim 7, wherein the umami receptor ligand is selected from the group consisting of glutamate salt, glutamine, acetyl glycine and aspartame.

11. A composition according to claim 7, wherein the fat receptor ligand is selected from the group consisting of a linoleic acid, an oleic acid, an omega-3 fatty acid, a palmitate, an oleoylethanolamide, a mixed fatty acid emulsion and an N-acylphosphatidylethanolamine (NAPE).

12. A composition according to claim 7, wherein the bile acid receptor ligand is selected from the group consisting of deoxycholic acid, a taurocholic acid and a chenodeoxycholic acid.

13. A composition according to any one of claims 1-12, further comprising an enhancer.

14. A composition comprising a non-nutritive agonist to a sweet chemosensory receptor wherein the composition has a sweetness potency of at least about 100 times the sweetness potency of sucrose, and wherein the composition is adapted to release the agonist to one or more of the duodenum, jejunum, ileum, caecum, colon and/or rectum of a subject.

15. A composition according to claim 6, wherein the composition releases at more than one pH range.

16. A composition according to claim 14, wherein the composition has a sweetness potency of at least 500 times the sweetness potency of sucrose.

17. A composition according to claim 14, wherein the composition has a sweetness potency of at least 1000 times the sweetness potency of sucrose.

18. A composition according to claim 14 further comprising a bitter receptor ligand, an umami receptor ligand, a fat receptor ligand, a bile acid receptor ligand, or any combination thereof.

19. A composition comprising a non-nutritive agonist to a sweet chemosensory receptor wherein the composition has a sweetness potency equivalent to at least about 500 grams of sucrose, and wherein the composition is adapted to release the agonist to one or more of the duodenum, jejunum, ileum, caecum, colon and/or rectum of a subject.

20. A composition according to claim 19, wherein the composition has a sweetness potency equivalent to at least about 5000 grams of sucrose.

21. A composition according to claim 19, wherein the composition has a sweetness potency equivalent to at least about 10000 grams of sucrose.

22. A composition according to claim 19 further comprising a bitter receptor ligand, an umami receptor ligand, a fat receptor ligand, a bile acid receptor ligand or any combination thereof.

\* \* \* \* \*